(12) United States Patent
Oshima

(10) Patent No.: US 7,438,854 B2
(45) Date of Patent: Oct. 21, 2008

(54) BIOMOLECULE SUBSTRATE, AND TEST AND DIAGNOSIS METHODS AND APPARATUSES USING THE SAME

(75) Inventor: Mitsuaki Oshima, Kyoto (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 188 days.

(21) Appl. No.: 10/501,487

(22) PCT Filed: May 7, 2003

(86) PCT No.: PCT/JP03/05689

§ 371 (c)(1),
(2), (4) Date: Jul. 13, 2004

(87) PCT Pub. No.: WO03/096015

PCT Pub. Date: Nov. 20, 2003

(65) Prior Publication Data

US 2005/0169797 A1    Aug. 4, 2005

(30) Foreign Application Priority Data

May 8, 2002    (JP)    ............................. 2002-133284

(51) Int. Cl.
*C12Q 1/68* (2006.01)
*G01N 33/53* (2006.01)
*G01N 21/00* (2006.01)
*G01N 33/553* (2006.01)

(52) U.S. Cl. .................... 422/82.05; 435/6; 435/7.1; 422/50; 422/59; 422/82.09; 422/82.11; 436/523; 436/527; 436/164

(58) Field of Classification Search ................ 536/24.3, 536/24.31, 25.32; 435/6; 422/55
See application file for complete search history.

(56) References Cited

U.S. PATENT DOCUMENTS

| 5,789,167 | A | * | 8/1998 | Konrad ........................ 435/6 |
| 5,804,384 | A | * | 9/1998 | Muller et al. ................. 435/6 |
| 6,214,560 | B1 | * | 4/2001 | Yguerabide et al. ......... 435/7.1 |
| 6,288,220 | B1 |   | 9/2001 | Kambara et al. |
| 6,329,139 | B1 | * | 12/2001 | Nova et al. ................... 435/6 |
| 6,589,779 | B1 | * | 7/2003 | McDevitt et al. .......... 435/288.7 |

(Continued)

FOREIGN PATENT DOCUMENTS

JP    11-243997    9/1999

(Continued)

OTHER PUBLICATIONS

International Search Report corresponding to application No. PCT/JP03/05689 dated Aug. 26, 2003.

(Continued)

*Primary Examiner*—Jill Warden
*Assistant Examiner*—Neil Turk
(74) *Attorney, Agent, or Firm*—RatnerPrestia

(57) ABSTRACT

A test apparatus is for testing a DNA substrate on which a plurality of DNA fragments for testing are arranged, wherein absolute precision is not required. A substrate is provided on which a plurality of biomolecule spots containing a group of biomolecules (e.g., DNA, etc.) of a specific type are formed, where the pattern or position of the DNA spot is changed depending on specific data so that information of the specific data is recorded on the substrate.

5 Claims, 54 Drawing Sheets

U.S. PATENT DOCUMENTS 6,592,822 B1 * 7/2003 Chandler .................. 422/82.05
2001/0009763 A1 * 7/2001 Kambara et al. ................ 435/6

FOREIGN PATENT DOCUMENTS

| JP | 2000-346842 | 12/2000 |
| --- | --- | --- |
| WO | WO 99/60170 A | 11/1999 |
| WO | WO 00/61198 | 10/2000 |

OTHER PUBLICATIONS

Supplementary Partial European Search Report corresponding to Application No. EP 03 72 1047 dated Jul. 17, 2007.

* cited by examiner

FIG. 5
(1) DNA CHIP
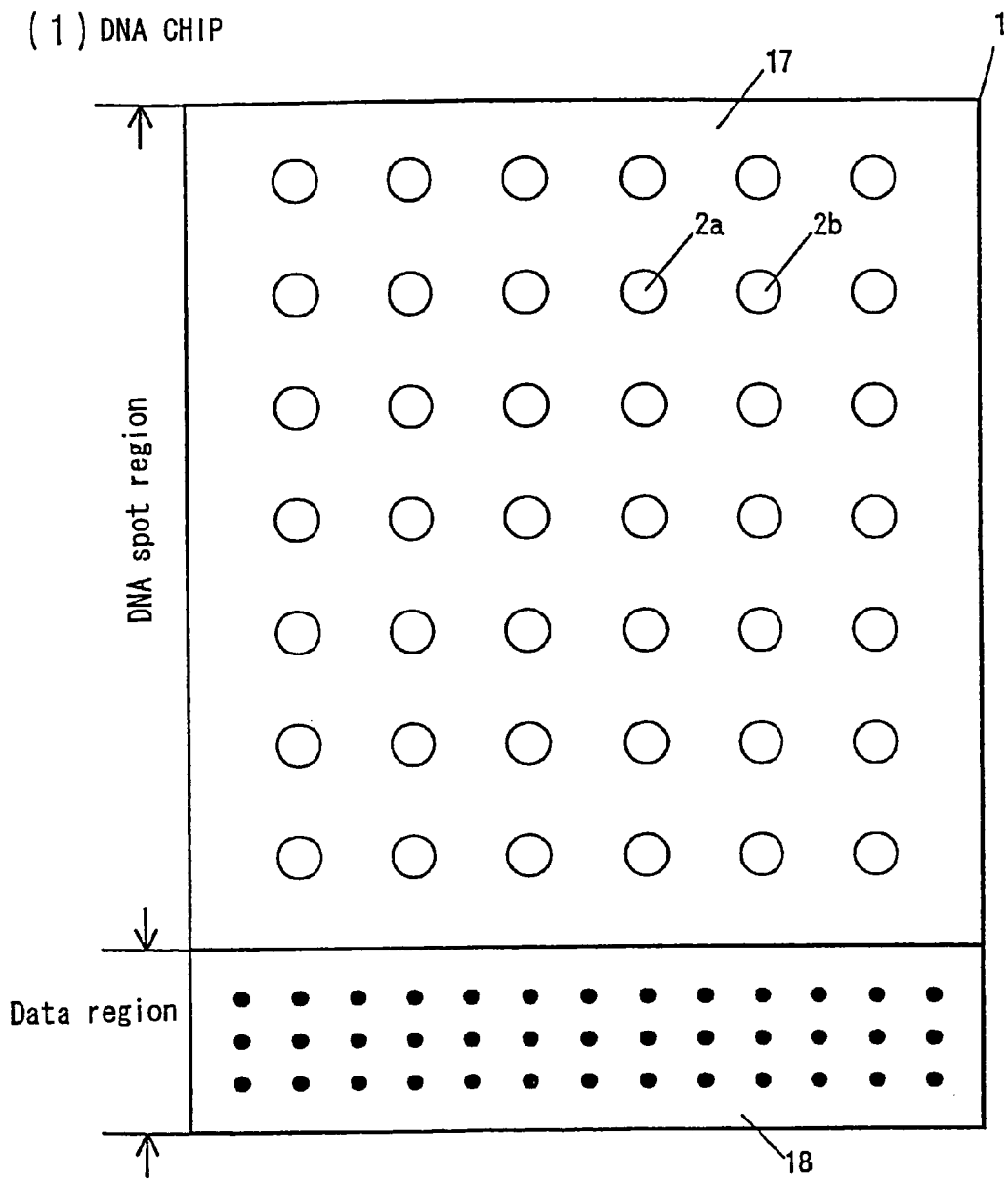
(2) Data structure
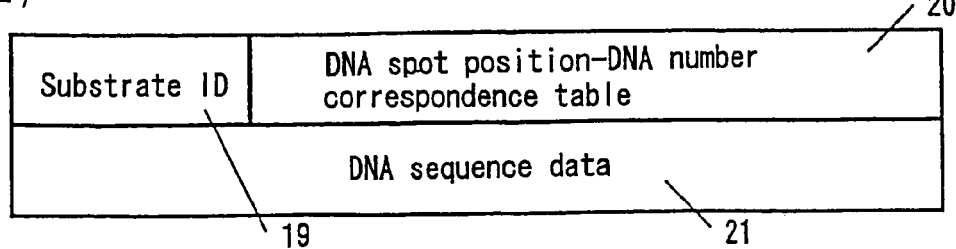

FIG. 6

DNA substrate attribute data

| | | | |
|---|---|---|---|
| | DNA substrate ID number | 0012-6426-2469-8792-2879-6237 | |
| Factory-shipped data | DNA number positional information | Track number=1 | Start number and end number of DNA number |
| | | | DNA number of first synchronization mark |
| | | | DNA number of second synchronization mark |
| | | | DNA number of third synchronization mark |
| | | | |
| | | Track number=2 | Start number and end number of DNA number |
| | | Track number=260 | Start number of DNA number=243142 |
| | | Final track number=n | |
| | Sequence information of DNA number (encrypted information) | DNA number=1 | (Ciphier of ATGCTGATA · · ·) |
| | | DNA number=2 | (Ciphier of ATGCTGATA · · ·) |
| | | | |
| | | DNA number=244270 | (Ciphier of ATGCTGATA · · ·) |
| Postscript data | First label attribute data | Excited light wavelength and light intensity | |
| | | Fluorescence wavelength and light intensity, half life | |
| | Second label attribute data | Excited light wavelength and light intensity | |
| | | Fluorescence wavelength and light intensity, half life | |

Labels: 19, 75, 20, 21, 76, 77, 78

FIG. 7
(1)
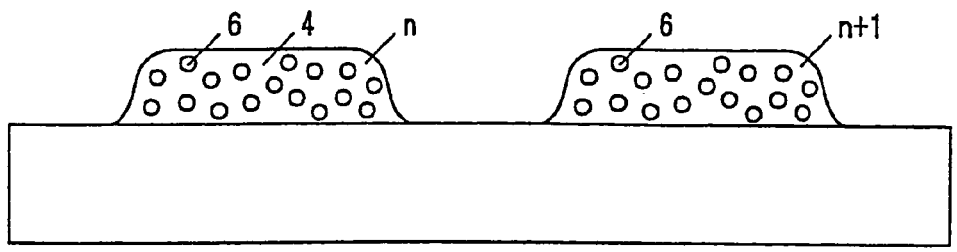
(2) Evaporation
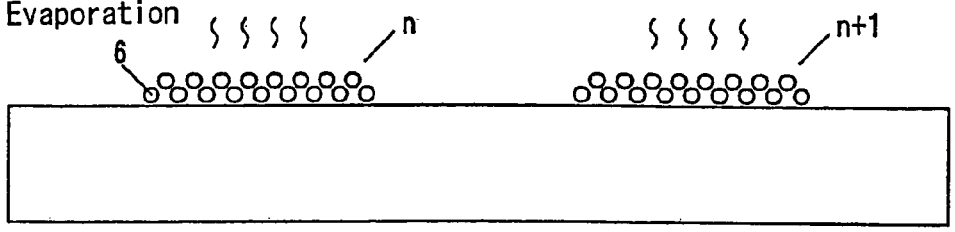
(3) Melting of microcapsule film
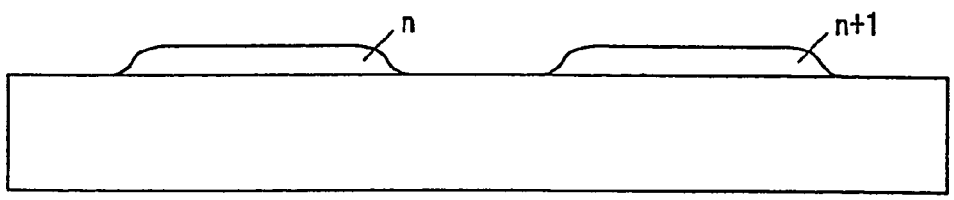
(4) Immobilization
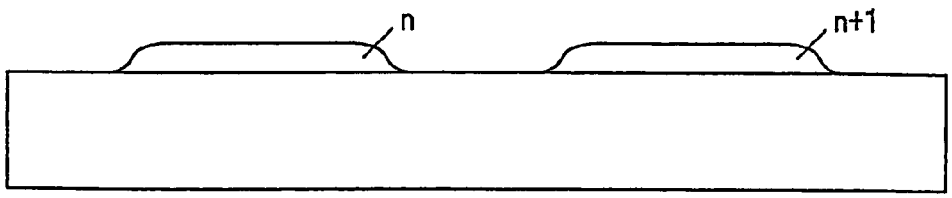
(5) Drying
(6) Washing

FIG.12
(1) DNA CHIP
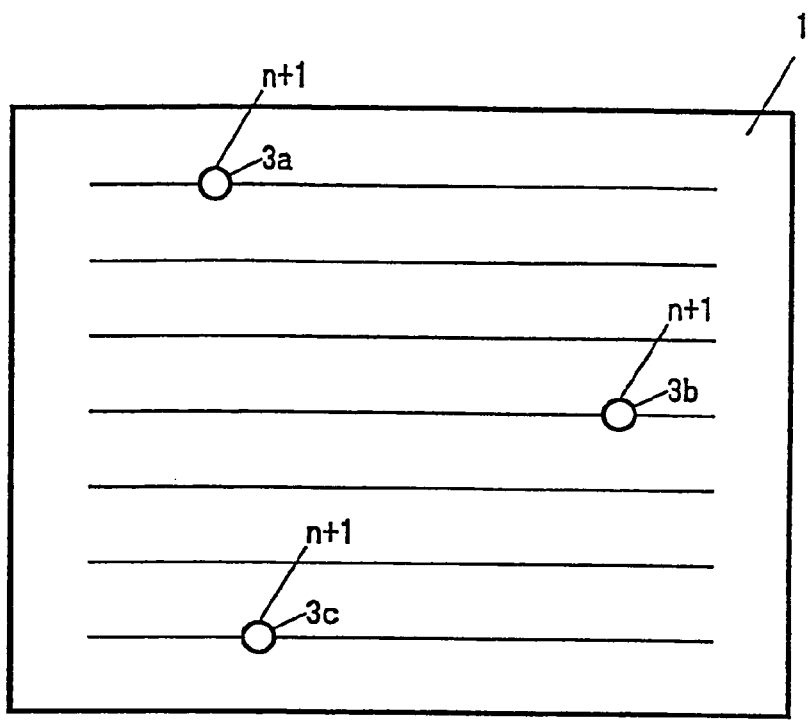
(2) DNA substrate
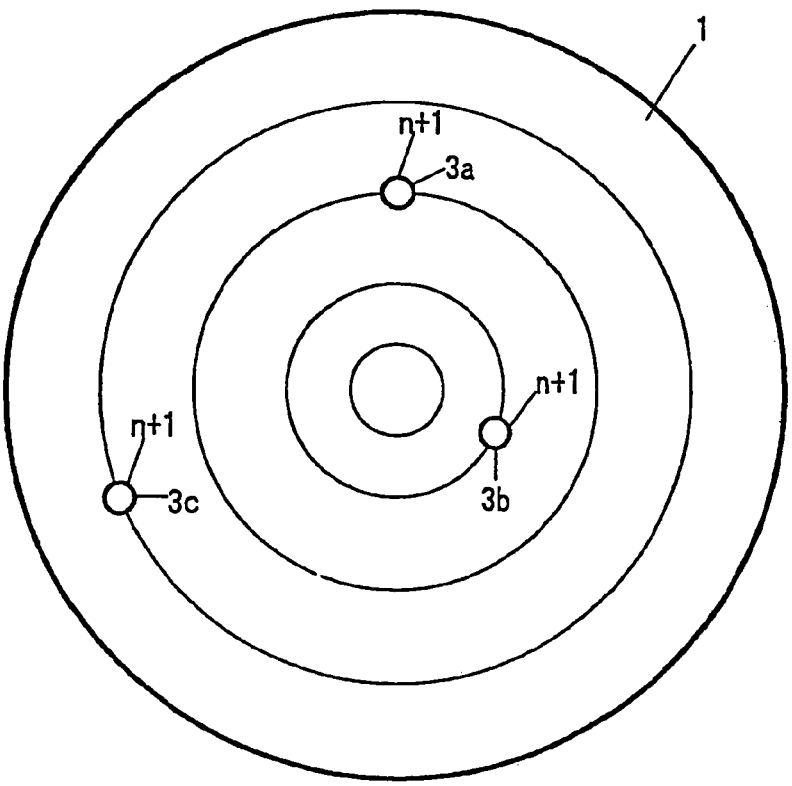

FIG.22

DNA number, and first and second label detection signals

| DNA number | Division number | First label detection signal | Second label detection signal |
|---|---|---|---|
| n+1 | 1 | 2 | 0 |
| | 2 | 5 | 0 |
| | 3 | 5 | 1 |
| | 4 | 2 | 0 |
| | 5 | 5 | 0 |
| | 6 | 5 | 0 |
| | 7 | 3 | 0 |
| | 8 | 3 | 0 |
| n+2 | 1 | 0 | 0 |
| | 2 | 0 | 0 |
| | 3 | 0 | 0 |
| | | | |
| n+6 | 1 | 0 | 2 |
| | 2 | 0 | 5 |
| | 3 | 0 | 5 |
| | 4 | 0 | 2 |
| | 5 | 0 | 5 |
| | 6 | 0 | 5 |
| | 7 | 0 | 5 |
| | 8 | 0 | 5 |

FIG.28
(1) Front side
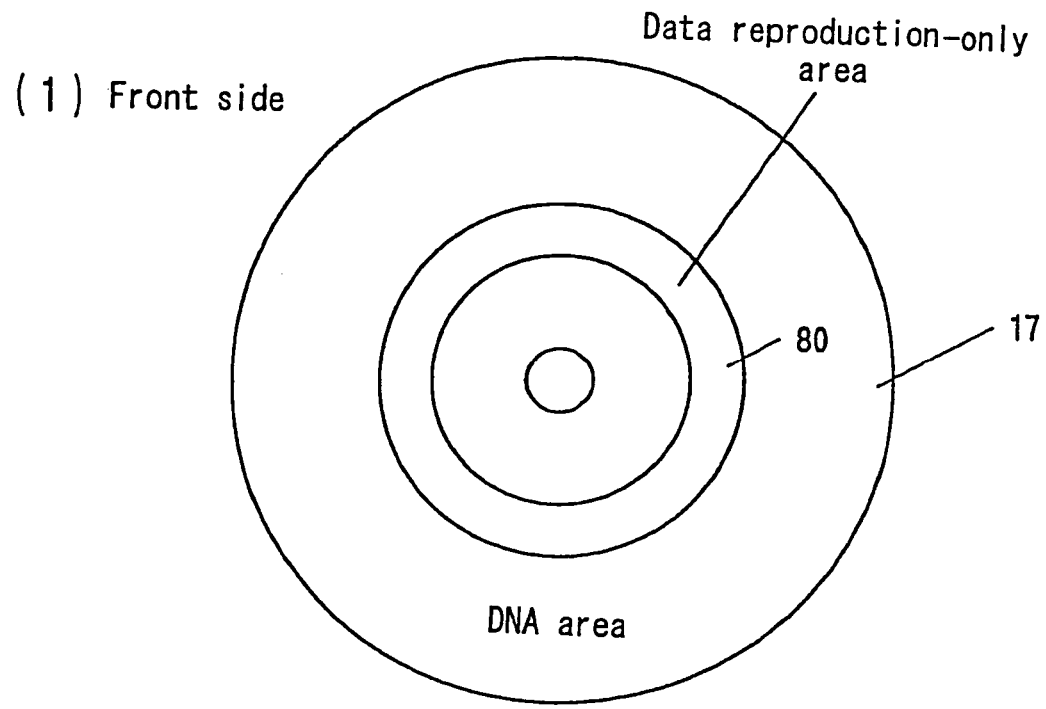
(2) Rear side
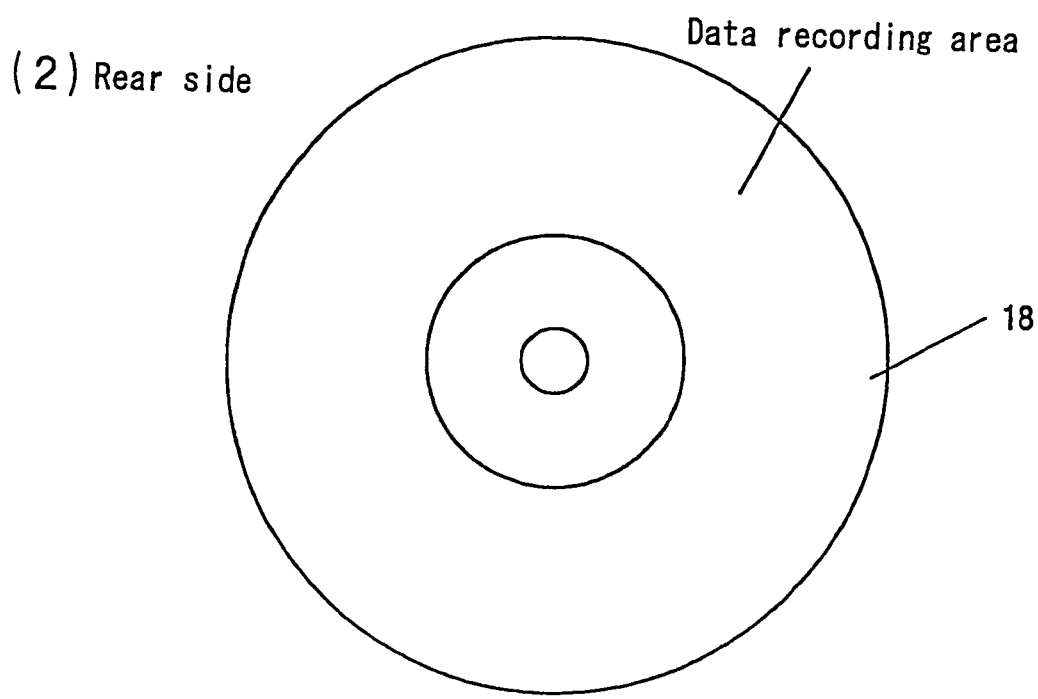

FIG.29
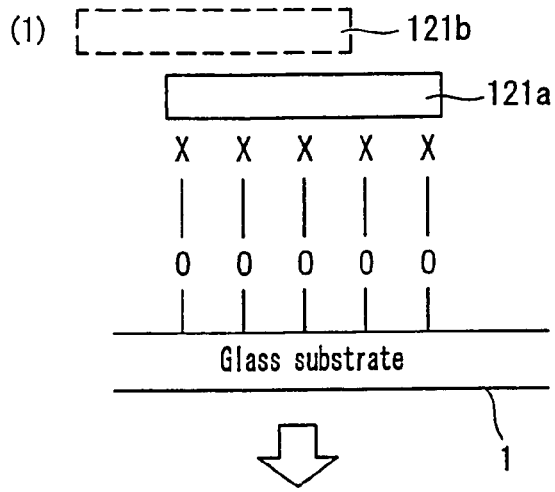
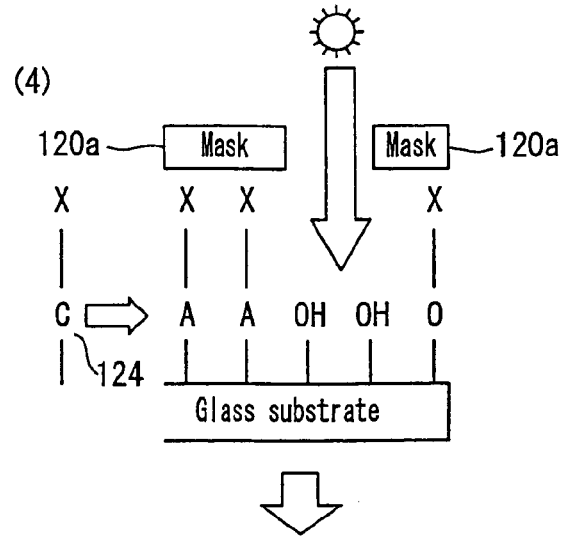
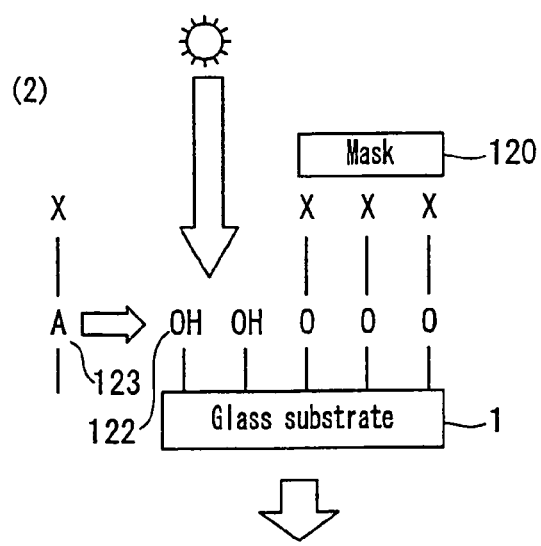
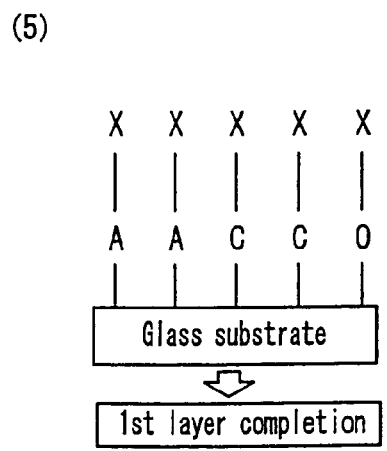
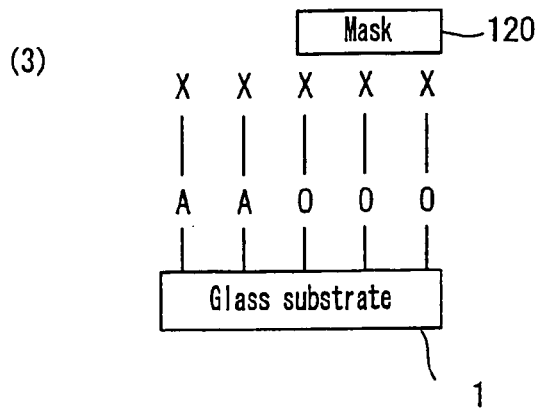
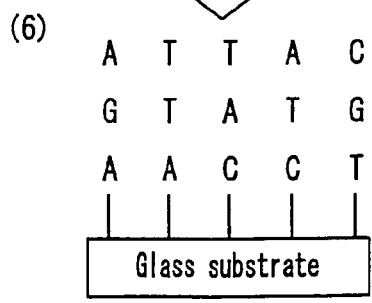

FIG. 40

| Identification number | | Probe attribute | | |
|---|---|---|---|---|
| Address | Number | (DNA) sequence | | 146 |
| 1011011011  23 | | ATGA...... | | |

Analysis result

| | Gene number (183) | Gene attribute (184) | Selected output (185) |
|---|---|---|---|
| 1 | Gene A | Information relating disease a | Output |
| 2 | Gene B | Information relating disease b | |
| 3 | Gene C | Information relating disease c | |
| 4 | Gene D | Information relating disease a | Output |
| 5 | Gene E | Information relating disease d | |
| 6 | Gene F | Information relating disease e | |
| 7 | Gene G | Information relating disease a | Output |
| 8 | Gene H | Information relating disease b | |

BIOMOLECULE SUBSTRATE, AND TEST AND DIAGNOSIS METHODS AND APPARATUSES USING THE SAME

THIS APPLICATION IS A U.S. NATIONAL PHASE APPLICATION OF PCT INTERNATIONAL APPLICATION PCT/JP03/05689.

TECHNICAL FIELD

The present invention relates to a substrate for use in a test for detecting a biomolecule (e.g., DNA, RNA, a protein, a low-weight organic molecule (ligand, etc.), sugar, lipid, etc.), a biomolecule chip, and a detection apparatus and test (including screening) and diagnosis methods using the same.

BACKGROUND ART

Recently, science and technologies related to genes have been developed more remarkably than expected. As a technique for detecting, analyzing and measuring genetic information, an apparatus called a biomolecule chip (including a DNA chip, a biochip, a microarray, a protein chip, etc.) and a test method using the same have recently received attention. A number of different nucleic acids (DNA such as cDNA and genomic DNA, RNA, PNA, etc.) or peptides are arranged and fixed in spotted pattern on a substrate made of glass or silicon. On this substrate, fragments of sample DNA to be tested are hybridized with a labeling substance, such as a fluorophore or an isotope or the like, and capture DNA, or alternatively, a sample polypeptide or ligand to be tested is conjugated with a labeling protein by means of their interaction. A detector is used to detect fluorescence from the labeled DNA or the labeling peptide in each spot, or a radiation detector is used to detect radioactivity therefrom, thereby obtaining information on arrangement of labeled DNA or labeling peptide spots. By analyzing this data, genetic information on the sample DNA can be obtained.

A gene detection method using a DNA chip or the like has the potential to be widely used in the analysis of genes for the diagnosis of a disease or analysis of an organism in the future. Examples of a chip application include screening of a compound library for combinatorial chemistry or the like. The versatility of the chips also has received attention.

To date, however, methods for fabricating biomolecule chips as described above require high-precision equipment, leading to high cost for a detection substrate. Moreover, an apparatus for detecting a labeled DNA requires high precision, and therefore, it is difficult for such an apparatus to come into widespread use in small business entities or practitioners. Biomolecule chips do not have sufficient ability to process a large amount of data. Therefore, a substrate or a chip capable of processing data in an easy and efficient manner is expected.

The above-described detection substrate or detection apparatus demands a method which does not require high precision. An object of the present invention is to provide a system which can be made even using a poor-precision test apparatus and in which system a test can be performed.

DISCLOSURE OF THE INVENTION

To solve the above-described problem, the present invention provides an apparatus comprising a substrate on which a plurality of biomolecule spots made of a specific type of biomolecule (e.g., DNA, etc.), in which a pattern or arrangement of the spot of the biomolecule (e.g., DNA) is changed depending on specific data so that the data is recorded on the substrate.

Therefore, the present invention provides the following.

In one aspect, the present invention provides a method for fabricating a biomolecule substrate, comprising the steps of: 1) providing a set of biomolecules and a substrate; 2) enclosing the set of biomolecules into microcapsules on the biomolecule-type-by-biomolecule-type basis; and 3) spraying the biomolecule microcapsules onto the substrate.

In one embodiment, the present invention further comprises the step of washing the biomolecule microcapsules after the enclosing step.

In another embodiment, the spraying step is performed by an ink jet method.

In another embodiment, the ink jet method is performed by a Bubble Jet® method.

In another embodiment, the present invention further comprises the step of setting the temperature of a solution used in the spraying step to be higher than the melting point of a shell of the biomolecule microcapsulate.

In another embodiment, the microcapsules of the set of biomolecules of different types are disposed at different positions.

In another embodiment, the spraying step is performed by a PIN method.

In another embodiment, the biomolecule contains at least one of DNA, RNA and a peptide.

In another embodiment, the biomolecule is DNA.

In another embodiment, the biomolecule is cDNA or genomic DNA.

In another embodiment, the present invention further comprises the step of perform labeling specific to each microcapsule.

In another aspect, the present invention provides a biomolecule chip, comprising: a substrate; and biomolecules and chip attribute data arranged on the substrate, wherein the chip attribute data is arranged in the same region as that of the biomolecules.

In one embodiment, the chip attribute data contains information relating to chip ID and the substrate.

In another embodiment, the present invention further comprises a recording region, wherein the recording region is placed on the same substrate as that of the biomolecule and the chip attribute data, and at least one of subject data and measurement data is recorded in the recording region.

In another embodiment, the chip attribute data is recorded in such a manner as to be read out by the same means as that for detecting the biomolecule.

In another embodiment, a specific mark is attached to the substrate.

In another embodiment, a specific mark is arranged based on the chip attribute data.

In another embodiment, the chip attribute data contains the biomolecule attribute data.

In another embodiment, information relating to an address of the biomolecule is further recorded.

In another embodiment, the address is a tracking address.

In another embodiment, the chip attribute data is encrypted.

In another embodiment, data relating to a label used to detect the biomolecule is recorded.

In another embodiment, the data relating to the label contains at least one of the wavelength of excited light and the wavelength of fluorescence.

In another embodiment, the biomolecule contains at least one of DNA, RNA and a peptide.

In another embodiment, the biomolecule is DNA.

In another embodiment, the biomolecule is cDNA or genomic DNA.

In another aspect, the present invention provides a biomolecule chip, comprising: 1) a substrate; and 2) biomolecules arranged on the substrate, wherein spots of the biomolecules are spaced by at least one non-equal interval, an address of the biomolecule spot can be identified from the non-equal interval.

In one embodiment, the non-equal interval is modulated.

In another embodiment, the non-equal interval is present in at least two directions.

In another aspect, the present invention provides a biomolecule chip. This biomolecule chip comprises: 1) a substrate; and 2) biomolecules arranged on the substrate, wherein the biomolecules include a distinguishable first biomolecule and a distinguishable second biomolecule, an address of the biomolecule can be identified based on an arrangement of spots of the first biomolecules and spots of the second biomolecule.

In one embodiment, a label distinguishable from the biomolecule is placed between the biomolecule spots.

In another embodiment, the distinguishable label can be detected by detection means.

In another embodiment, the label is arranged in a horizontal direction and a vertical direction on the substrate.

In another embodiment, a synchronization mark is arranged.

In another embodiment, the biomolecule contains at least one of DNA, RNA and a peptide.

In another embodiment, the biomolecule is DNA.

In another embodiment, the biomolecule is cDNA or genomic DNA.

In another aspect, the present invention provides a biomolecule chip, comprising: 1) a substrate; and 2) biomolecules arranged on the substrate, where in spots storing attribute data are arranged on a side of the substrate opposite to a side on which spots of the biomolecules are arranged.

In another embodiment, the attribute data is address information.

In another aspect, the present invention provides a biomolecule chip, comprising: 1) a substrate; 2) biomolecules arranged on the substrate; and 3) a data recording region.

In one embodiment, the data recording region is placed on the side opposite to the side on which the biomolecules are arranged.

In another aspect, the present invention provides a method for detecting a label of a biomolecule chip, comprising the steps of: 1) providing a biomolecule chip on which at least one labeled biomolecule is arranged; 2) switching detection elements sequentially for detecting the biomolecules on the biomolecule chip; and 3) identifying a signal detected by the detection element.

In one embodiment, the present invention further comprises: 4) adding up each detected signal.

In another embodiment, the signal is separated by a wavelength separation mirror.

In another embodiment, the biomolecule substrate further contains a synchronization mark, and the label is identified based on the synchronization mark.

In another embodiment, the biomolecule substrate contains address information on a rear side of the biomolecule, and the label is identified based on the address information.

In another aspect, the present invention provides a method for detecting information on an organism, comprising the steps of: 1) providing a biomolecule sample from the organism; 2) providing the biomolecule chip of the present invention; 3) contacting the biomolecule sample to the biomolecule chip, and placing the biomolecule chip under conditions which causes an interaction between the biomolecule sample and a biomolecule placed on the biomolecule chip; and 4) detecting a signal caused by the biomolecule and a signal caused by the interaction, wherein the signal is an indicator for at least one information parameter of the organism, and the signal is related to an address assigned to the non-equal interval or the spot arrangement.

In another embodiment, the biomolecule sample contains nucleic acid, and the biomolecule placed on the biomolecule chip is nucleic acid.

In another embodiment, the sample contains a protein and the biomolecule placed on the biomolecule chip is an antibody, or the sample contains an antibody and the biomolecule placed on the biomolecule chip is a protein.

In another embodiment, the present invention further comprises labeling the biomolecule sample with a label molecule.

In another embodiment, the label molecule can be distinguished from the biomolecule placed on the biomolecule chip.

In another embodiment, the label molecule contains a fluorescent molecule, a phosphorescent molecule, a chemoluminescent molecule, or a radioactive isotope.

In another embodiment, the signal detecting step is performed at a site different from where the interaction occurs.

In another embodiment, the signal detecting step is performed at the same site as where the interaction occurs.

In another embodiment, the present invention further comprises encrypting the signal.

In another embodiment, the present invention further comprises subjecting the signal to filtering so as to extract only signal relating to required information.

In another aspect, the present invention provides a method for diagnosing a subject, comprising the steps of: 1) providing a sample from the subject; 2) providing the biomolecule chip of the present invention; 3) contacting the biomolecule sample to the biomolecule chip, and placing the biomolecule chip under conditions which cause an interaction between the biomolecule sample and a biomolecule placed on the biomolecule chip; 4) detecting a signal caused by the biomolecule and a signal caused by the interaction, wherein the signal is at least one diagnostic indicator for the subject, and the signal is related to an address assigned to the non-equal interval or the spot arrangement; and 5) determining the diagnostic indicator from the signal.

In another embodiment, the sample is nucleic acid, and the biomolecule placed on the biomolecule chip is nucleic acid.

In another embodiment, the sample contains a protein and the biomolecule placed on the biomolecule chip is an antibody, or the sample contains an antibody and the biomolecule placed on the biomolecule chip is a protein.

In another embodiment, the present invention further comprises labeling the sample with a label molecule.

In another embodiment, the label molecule can be distinguished from the biomolecule placed on the biomolecule chip.

In another embodiment, the label molecule is a fluorescence molecule, a phosphorescent molecule, a chemoluminescent molecule, or a radioactive isotope.

In another embodiment, the diagnostic indicator is an indicator for a disease or a disorder.

In another embodiment, the diagnostic indicator is based on single nucleotide polymorphism (SNP).

In another embodiment, the diagnostic indicator is based on a genetic disease.

In another embodiment, the diagnostic indicator is based on the expression level of a protein.

In another embodiment, the diagnostic indicator is based on a test result of a biochemical test.

In another embodiment, the determining step is performed at a site different from where the interaction occurs.

In another embodiment, the signal detecting step is performed at the same site as where the interaction occurs.

In another embodiment, the present invention further comprises encrypting the signal.

In another embodiment, the present invention further comprises subjecting the signal to filtering so as to extract only signal relating to required information.

In another embodiment, in the detecting step biomolecule attribute data is hidden, and in the determining step personal information data is hidden.

In another aspect, the present invention provides a test apparatus for information on an organism, comprising: 1) the biomolecule chip of the present invention; 2) a sample applying section in fluid communication with the biomolecule chip; 3) a reaction control section for controlling a contact and an interaction between the biomolecule placed on the biomolecule chip and a biomolecule sample applied from the sample applying section; and 4) a detection section for detecting a signal caused by the interaction, wherein the signal is an indicator for at least one information parameter of the organism, and the signal is related to an address assigned to the non-equal interval or the spot arrangement.

In another embodiment, the present invention further comprises a section for receiving and sending the signal.

In another embodiment, the present invention further comprises a region for recording the signal.

In another aspect, the present invention provides a diagnosis apparatus for a subject. This diagnosis apparatus comprises: 1) the biomolecule chip of the present invention; 2) a sample applying section in fluid communication with the biomolecule chip; 3) a reaction control section for controlling a contact and an interaction between the biomolecule placed on the biomolecule chip and a biomolecule sample applied from the sample applying section; 4) a detection section for detecting a signal caused by the biomolecule and a signal caused by the interaction, wherein the signal is an indicator for at least one information parameter of the organism, and the signal is related to an address assigned to the non-equal interval or the spot arrangement; and 5) determining the diagnostic indicator from the signal.

In one embodiment, the present invention further comprises a section for receiving and sending the signal.

In another embodiment, the present invention further comprises a region for recording the signal.

In one aspect, the present invention provides a biological test system. This biological test system comprises: A) a main sub-system, comprising: 1) the biomolecule chip of the present invention; 2) a sample applying section in fluid communication with the biomolecule chip; 3) a reaction control section for controlling a contact and an interaction between the biomolecule placed on the biomolecule chip and a biomolecule sample applied from the sample applying section; 4) a detection section for detecting a signal caused by the biomolecule and a signal caused by the interaction, wherein the signal is an indicator for at least one information parameter of the organism, and the signal is related to an address assigned to the non-equal interval or the spot arrangement; and 5) a sending and receiving section for sending and receiving a signal, and B) a sub sub-system, comprising: 1) a sending and receiving section for sending and receiving a signal; and 2) a test section for calculating a test value from the signal received from the main sub-system. The main sub-system and the sub sub-system are connected together via a network.

In another embodiment, the signal received by the sub sub-system contains a signal relating to measurement data measured by the sub sub-system.

In another embodiment, the attribute data contains chip ID, personal information data, and biomolecule attribute data, the main sub-system contains the chip ID and the personal information data, but does not contain the biomolecule attribute data, and the sub sub-system contains the chip ID and the biomolecule attribute data, but does not contain the personal information data, and the sub sub-system sends the test value, determined in response to a request, to the main sub-system.

In another embodiment, the network is the Internet.

In another embodiment, the signal to be sent and received is encrypted.

In another aspect, the present invention provides a diagnosis system. This diagnosis system comprises: A) a main sub-system, comprising: 1) the biomolecule chip of the present invention; 2) a sample applying section in fluid communication with the biomolecule chip; 3) a reaction control section for controlling a contact and an interaction between the biomolecule placed on the biomolecule chip and a biomolecule sample applied from the sample applying section; 4) a detection section for detecting a signal caused by the biomolecule and a signal caused by the interaction, wherein the signal is an indicator for at least one information parameter of the organism, and the signal is related to an address assigned to the non-equal interval or the spot arrangement; and 5) a sending and receiving section for sending and receiving a signal, and B) a sub sub-system, comprising: 1) a sending and receiving section for sending and receiving a signal; and 2) a determination section for determining the diagnostic indicator from the signal received from the main sub-system. The main sub-system and the sub sub-system are connected together via a network.

In another embodiment, the signal received by the sub sub-system contains a signal relating to measurement data measured by the sub sub-system.

In another embodiment, the attribute data contains chip ID, personal information data, and biomolecule attribute data, the main sub-system contains the chip ID and the personal information data, but does not contain the biomolecule attribute data, and the sub sub-system contains the chip ID and the biomolecule attribute data, and data for determining a diagnostic indicator from biomolecule attribute data, but does not contain the personal information data, and the sub sub-system sends the diagnostic indicator, determined in response to a request, to the main sub-system.

In another embodiment, the network is the Internet.

In another embodiment, the signal to be sent and received is encrypted.

In another embodiment, the present invention provides a test apparatus for biological information. This test apparatus comprises: a substrate; a support for the substrate; a plurality of groups of biomolecules arranged on the substrate, each group containing the biomolecules of the same type; shifting means for shifting the substrate; a light source for exciting a fluorescence substance labeling a sample to be tested; and optical means for converging light from the light source. The light source is caused to emit light intermittently in response to an intermittent emission signal so as to excite the fluorescence substance, fluorescence from the fluorescence substance is detected by a photodetector during a period of time when the intermittent emission signal is paused, identification information is reproduced from an arrangement of the DNAs, and the biomolecules emitting fluorescence is identified.

In another embodiment, the present invention further comprises means for adding up detected detection signals.

In another embodiment, the present invention further comprises a wavelength separation mirror.

In another embodiment, the present invention provides use of the biomolecule chip of the present invention for fabricating an apparatus for testing biological information.

In another embodiment, the present invention provides use of the biomolecule chip of the present invention for fabricating an apparatus for diagnosing a subject.

In another aspect, the present invention provides a biomolecule bead-containing tube containing a biomolecule bead array in which biomolecule beads consisting of a spherical bead and a specific biomolecule species immobilized thereon are arranged in a tubular container made of a material transmitting a light having a specific wavelength, wherein a spherical mark bead made of a material optically distinguishable from the material constituting the spherical bead of said biomolecule bead is inserted in a predetermined order between specific biomolecule beads in the biomolecule bead array.

In one embodiment, the mark beads are arranged corresponding to an identification code indicating identification data.

In another embodiment, the biomolecule bead-containing tube has a first region where a number of the biomolecule beads is larger than a number of the mark beads, and a second region where a number of the mark beads is larger than a number of the biomolecule beads.

In another embodiment, at least the mark beads are arranged in the second region corresponding to an identification code indicating identification data.

In another embodiment, the identification data comprise an identification number for the biomolecule beads-containing tube.

In another embodiment, the mark beads are arranged in the first region corresponding to an identification code indicating identification data.

In a further aspect, the present invention provides a reproducer reading out data recorded in a biomolecule bead-containing tube by irradiating the biomolecule bead-containing tube with a light and detecting a transmitted light or a reflected light from at least a mark bead.

In one embodiment, the reproducer reads out the data; and obtains information of a DNA or a protein immobilized on the biomolecule beads in the biomolecule bead-containing tube by irradiating the biomolecule beads with a light and observing fluorescence from the biomolecule beads.

In another embodiment, the reproducer obtains identification information as the data.

In another embodiment, the reproducer obtains arrangement information for the biomolecule beads in the biomolecule bead-containing tube based on the identification information obtained from the biomolecule bead-containing tube.

In another embodiment, the reproducer obtains information of a DNA or a protein immobilized on the biomolecule beads in the biomolecule bead-containing tube based on the arrangement information for the biomolecule beads obtained based on the identification information.

In another embodiment, the reproducer diagnoses a disease from the information of a DNA or a protein obtained based on the identification information.

BRIEF DESCRIPTION OF THE DRAWINGS

The present invention will be herein described with reference to the drawings briefly described below. The drawings are provided for the purpose of illustrating preferable embodiments of the present invention, but not for the purpose of restricting the scope of the present invention. The scope of the present invention is specified only by the claims attached thereto. Each figure will be described below.

Figure 1:
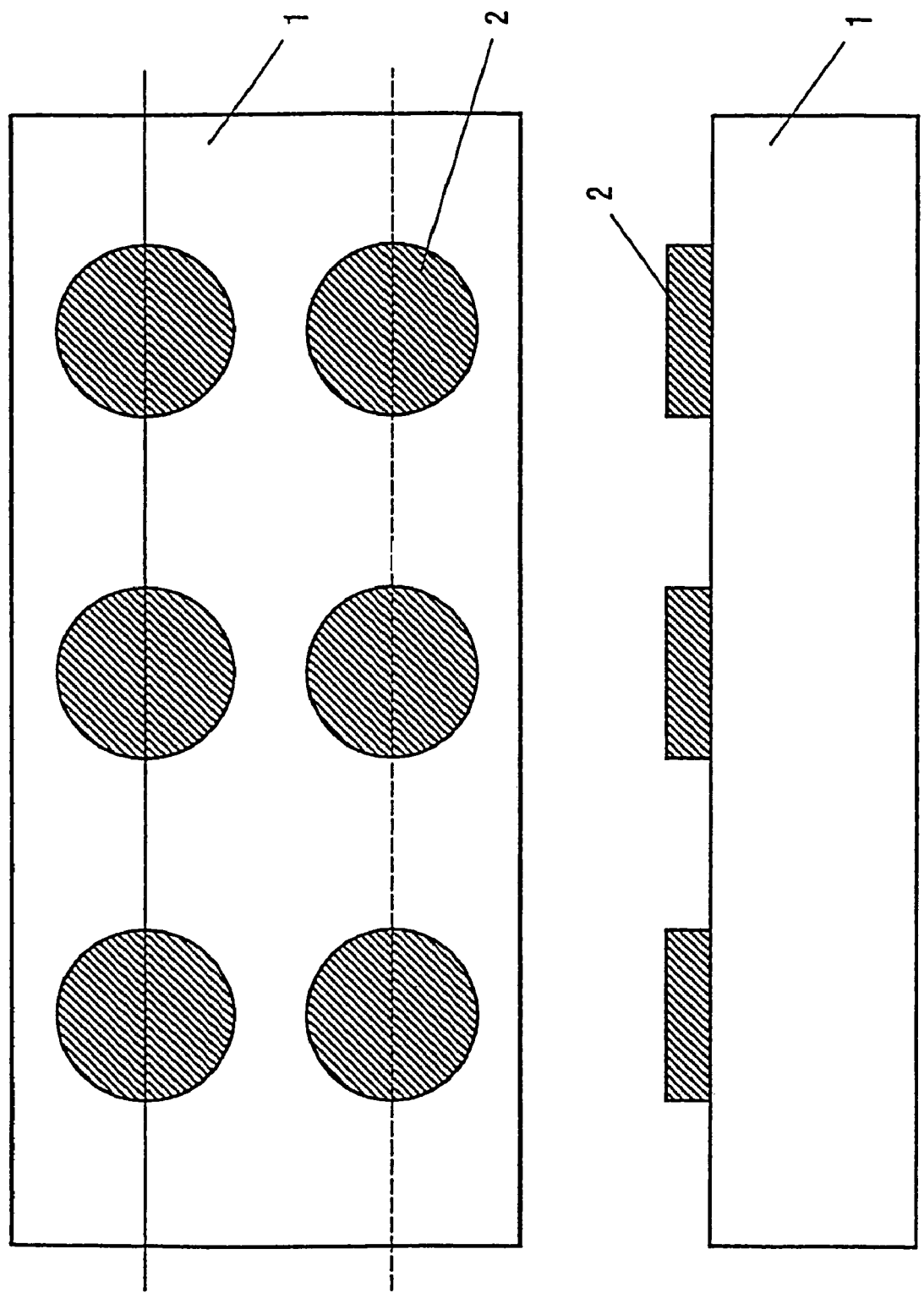
FIG. 1.

(a) A top view showing a substrate on which DNA is placed, according to an embodiment of the present invention.

(b) A cross-sectional view showing a substrate on which DNA is placed, according to an embodiment of the present invention.

FIG. 2:

A diagram showing a method for fabricating a DNA microcapsule according to an embodiment of the present invention.

FIG. 3:

A diagram shown in a method for attaching DNA by a pin method according to an embodiment of the present invention.

FIG. 4:

A diagram showing a method for shifting DNA to a pin according to an embodiment of the present invention.

FIG. 5:

A top view showing a DNA chip according to an embodiment of the present invention, and a data structure diagram.

FIG. 6:

A diagram showing a structure of DNA substrate attribute data according to an embodiment of the present invention.

FIG. 7:

A diagram showing a method for fixing DNA according to an embodiment of the present invention.

FIG. 8:

A schematic diagram showing a method for fixing DNA according to an embodiment of the present invention.

FIG. 9:

A block diagram showing a method for ejecting DNA by an ink jet method according to an embodiment of the present invention.

FIG. 10:

A diagram showing an arrangement of DNA on a substrate according to an embodiment of the present invention.

FIG. 11:

A diagram showing ejection in an inkjet method according to an embodiment of the present invention.

FIG. 12:

A diagram showing an arrangement of DNA spots on a substrate according to an embodiment of the present invention.

FIG. 13:

A diagram showing hybridization of labeled DNA according to an embodiment of the present invention.

FIG. 14:

A block diagram showing a test apparatus according to an embodiment of the present invention.

FIG. 15:

A flowchart showing ejection of a microcapsule according to an embodiment of the present invention.

FIG. 16:

A diagram showing an operation of a mirror according to an embodiment of the present invention.

FIG. 17:

A diagram showing a relationship between excited light and fluorescence according to an embodiment of the present invention.

FIG. 18:

A diagram showing scanning of DNA spots according to an embodiment of the present invention.

FIG. 19:

A diagram showing a relationship between a light receiving array and fluorescence according to an embodiment of the present invention.

FIG. 20:

A timing chart showing detection of fluorescence according to an embodiment of the present invention.

FIG. 21:

A block diagram showing a photodetector comprising a light receiving array according to an embodiment of the present invention.

FIG. 22:

A diagram showing exemplary data of a label detection signal according to an embodiment of the present invention.

FIG. 23:

A diagram showing a principle of a detection apparatus according to an embodiment of the present invention.

FIG. 24:

A diagram showing a principle of a detection apparatus according to an embodiment of the present invention.

FIG. 25:

A top view showing a relationship between a DNA spot and a track according to an embodiment of the present invention.

FIG. 26:

A diagram showing an arrangement of DNA spots according to an embodiment of the present invention.

FIG. 27:

A top view showing a circular substrate according to an embodiment of the present invention.

FIG. 28:

A diagram showing a DNA area of a circular substrate according to an embodiment of the present invention.

FIG. 29:

A diagram showing a procedure for fabricating a DNA substrate using a semiconductor process method according to an embodiment of the present invention.

FIG. 30:

A diagram showing a principle of an ink jet method according to an embodiment of the present invention.

FIG. 31:

A flowchart showing a method for detecting fluorescence by scanning a plurality of times according to an embodiment of the present invention.

FIG. 32:

A timing chart showing excited light and detected light in a method for scanning a plurality of times according to an embodiment of the present invention.

FIG. 33:

A diagram showing a method for fabricating a biomolecule chip by a tube method according to an embodiment of the present invention.

FIG. 34:

A diagram showing another method for fabricating a biomolecule chip by a tube method according to an embodiment of the present invention.

FIG. 35:

A diagram showing an arrangement of biomolecule spots by a tube method according to an embodiment of the present invention and a diagram showing buried data.

FIG. 36:

A diagram showing an arrangement of biomolecule spots by a tube method according to an embodiment of the present invention and a diagram showing buried data.

FIG. 37:

A diagram showing an arrangement of biomolecule spots by a tube method according to an embodiment of the present invention.

FIG. 38:

A diagram showing a method for arranging a biomolecule spot by a pin method according to an embodiment of the present invention.

FIG. 39:

A diagram showing a method for arranging a biomolecule spot by an inkjet method according to an embodiment of the present invention.

FIG. 40:

A diagram showing a table of an identification number and a biomolecule attribute data according to an embodiment of the present invention.

FIG. 41:

A flowchart showing a detection procedure using a pin method according to an embodiment of the present invention.

FIG. 42:

A diagram showing a data structure of data containing ECC buried by a tube method according to an embodiment of the present invention.

FIG. 43:

A block diagram showing a network type test system according to an embodiment of the present invention.

FIG. 44:

A block diagram showing a stand-alone type test system according to an embodiment of the present invention.

FIG. 45:

A diagram showing a table of analysis results according to an embodiment of the present invention.

FIG. 46:

A diagram showing a structure of a biomolecule chip according to an embodiment of the present invention.

FIG. 47:

A diagram showing a structure according to an embodiment of the present invention, in which an address can be identified by a specific arrangement.

FIG. 48:

A diagram showing a structure of a biomolecule chip according to an embodiment of the present invention, in which an address can be identified by a specific pattern.

FIG. 49:

(a) A cross-sectional view showing a DNA bead according to an embodiment of the present invention.

(b) A cross-sectional view showing a mark bead according to an embodiment of the present invention.

FIG. 50:

A diagram showing a principle of bead supplying according to an embodiment of the present invention.

FIG. 51:

A diagram showing a step for arranging DNA beads, according to an embodiment of the present invention.

FIG. 52:

A diagram showing a step for arranging mark beads, according to an embodiment of the present invention.

FIG. 53:

A diagram showing a step for arranging DNA beads by using a microcapsule according to an embodiment of the present invention.

FIG. 54:

A diagram showing a method for burying information by using mark beads according to the present invention.

FIG. 55:

A diagram showing a method for arranging DNA beads by using an enlarged DNA bead according to an embodiment of the present invention.

DESCRIPTION OF REFERENCE NUMERALS 1 substrate
2 DNA spot
3 DNA
4 main solution
5 main film
6 DNA microcapsule
7 sub-film
8 sub-solution
9 microcapsule
10 main container
11 container
12 tray
13 pin
14 moving pin
15 washing section
16 pin drum
17 DNA spot region
18 data region
19 substrate ID
20 DNA number-position correspondence table
21 DNA sequence data
22 labeled DNA
23 empty microcapsule
24 nozzle
25 supply section
26 eject section (heater)
27 eject control circuit
28 master control section
29 eject signal generation section
30 removal signal generation section
31 photodetector
32 unnecessary liquid removing section
33 deviation section
34 arrow
35 shift amount detector
36 shift control circuit
37 synchronization mark
38 fluorescence dye
39 detection apparatus
40 light source (for excitation)
41 mirror
42 lens
43 detection section
44 focus error signal detection section
45 tracking error signal detection section
46 focus control circuit
47 tracking control circuit
48 actuator
49 focus offset signal generation section
50 track offset signal generation section
51 spot number output section
52 track number output section
53 ECC decoder
54 DNA substrate attribute data reading portion
55 data processing section
56 synchronization signal generation section
57 substrate shift section
58 capture DNA number
59 second label signal detection section
60 first label signal detection section
61 first label signal output section
62 second label signal output section
63 data output section
64 positional information detection section
65 mirror
66 mirror
67 label signal detection section
68 step
69 main signal reproduction section
70 detection cell
71 excitation beam
72 scanning track
73 encryption key
74 cipher decoder
75 factory-shipped data region
76 postscript data region
77 first label attribute data
78 second label attribute data
79 synchronization data
80 data reproduction area
85 label detection signal
86 shift amount detector
87 pulsed light emission control section
88 pulsed light emission signal
89 sub-pulsed light emission signal
90 light detection section
91 array
92 switching section
93 addition section
94 label detection signal list
95 recording layer
96 address
97 start address
98 end address
99 innermost circumferential track number
100 outermost circumferential track number
111 counter
112 address counter
113 address block counter
114 sub-eject section
115 sub-solution supply section
116 sub-nozzle
118 step
120 mask
121 mask (for DNA spots)
122 hydroxy group
123 A (adenine)
124 C (cytosine)
125 G (guanine)
126 T (thymine)
130 tube
131 probe
132 container
133 sheet
134 mark tube
135 solution
136 mark tube
137 block
138 chip
139 fix plate
140 fix plate ID
141 biomolecule spot
142 mark spot
143 identification mark
144 synchronization mark
145 identification number
146 attribute table
147 test database
148 step (flowchart)
149 test apparatus
150 network
151 memory 152 error correction code
153 mark solution
154 mark biomolecule spot
155 analysis program
156 mark microcapsule
157 synchronization mark
158 synchronization mark
159 original data
160 flat tube
161 rectangular biomolecule spot
162 synchronization mark
170 subject
171 sample
172 biomolecule extraction section
173 specimen
174 main test system
175 test section
176 communication section
177 the Internet
178 sub-test system
179 communication section
180 analysis system
181 analysis section
182 selection section
183 output section
184 (biomolecule spot identification number) attribute database
185 selective output
186 request output
187 diagnosis system
188 diagnosis section
189 treatment policy production section
190 treatment policy output section
191 chip ID-subject correspondence database
192 diagnosis result output section
193 test system
194 black box section
195 input/output section
197 cipher decoding section
198 IC chip
199 electrode
200 substrate
201 non-volatile memory
300 biomolecule chip
301 biomolecule spot
302 equal interval
303 non-equal interval
310 biomolecule chip
311 first biomolecule spot
312 second biomolecule spot
320 DNA bead
321 DNA layer
322 mark bead
323 space bead
324
325 light source
326 arrow
327 glass tube
328 cap
329 DNA array
330 information recording region
331 start mark
332 end mark
333 (light-transmissive) mark bead
334 (light-absorbing) mark bead
335 bead supply section
336 terminal section
337 data row
338 first shell
339 second shell
340 first region
341 second region
342 third region
343 reflector

BEST MODE FOR CARRYING OUT THE INVENTION

It should be understood throughout the present specification that articles for singular forms (e.g., "a", "an", "the", etc. in English; "ein", "der", "das", "die", etc. and their inflections in German; "un", "une", "le", "la", etc. in French; "un", "una", "el", "la", etc. in Spanish; and articles, adjectives, etc. in other languages) include the concept of their plurality unless otherwise mentioned. It should be also understood that terms as used herein have definitions ordinarily used in the art unless otherwise mentioned.

Hereinafter, the meanings of terms as particularly used herein will be described.

The terms "substrate" and "support" as used herein have the same meaning, i.e., a material for an array construction of the present invention (preferably, in a solid form). Examples of a material for the substrate include any solid material having a property of binding to a biomolecule used in the present invention either by covalent bond or noncovalent bond, or which can be derived in such a manner as to have such a property.

Such a material for the substrate may be any material capable of forming a solid surface, for example, including, but being not limited to, glass, silica, silicon, ceramics, silica dioxide, plastics, metals (including alloys), naturally-occurring and synthetic polymer (e.g., polystyrene, cellulose, chitosan, dextran, and nylon). The substrate may be formed of a plurality of layers made of different materials. For example, an inorganic insulating material, such as glass, silica glass, alumina, sapphire, forsterite, silicon carbide, silicon oxide, silicon nitride, or the like, can be used. Moreover, an organic material, such as polyethylene, ethylene, polypropylene, polyisobutylene, polyethylene terephthalate, unsaturated polyester, fluorine-containing resin, polyvinyl chloride, polyvinylidene chloride, polyvinyl acetate, polyvinyl alcohol, polyvinyl acetal, acrylic resin, polyacrylonitrile, polystyrene, acetal resin, polycarbonate, polyamide, phenol resin, urea resin, epoxy resin, melamine resin, styrene acrylonitrile copolymer, acrylonitrilebutadienestyrene copolymer, silicone resin, polyphenylene oxide, or polysulfone, can be used. In the present invention, a film used for nucleic acid blotting, such as a nitrocellulose film, a PVDF film, or the like, can also be used.

In one embodiment of the present invention, an electrode material can be used for a substrate electrode which serves as both a substrate and an electrode. In the case of such a substrate electrode, a surface of the substrate electrode is separated into electrode regions by an insulating layer region. Preferably, different biomolecules are fixed to the respective isolated electrode regions. The electrode material is not particularly limited. Examples of the electrode material include a metal alone, such as gold, gold alloy, silver, platinum, mercury, nickel, palladium, silicon, germanium, gallium, tungsten, and the like, and alloys thereof, or carbon, such as graphite, glassy carbon, and the like, or oxides or compounds thereof. Further, a semiconductor compound, such as silicon oxide and the like, or various semiconductor devices, such as CCD, FET, CMOS, and the like, can be used. When a substrate electrode in which an electrode film is formed on an insulating substrate so that the substrate is integrated with the electrode, the electrode film can be produced by plating, printing, sputtering, deposition or the like. In the case of deposition, an electrode film can be formed by a resistance heating method, a high-frequency heating method, an electron-beam heating method, or the like. In the case of sputtering, an electrode film can be produced by direct current sputtering, bias sputtering, asymmetric AC sputtering, getter sputtering, high-frequency sputtering, or the like. Furthermore, electropolymerized film, such as polypyrrole, polyaniline, and the like, or a conductive polymer can be used. An insulating material used for separating the electrode surface in the present invention is not particularly limited, but is preferably a photopolymer or a photoresist material. Examples of the resist material include a photoresist for light exposure, a photoresist for ultraviolet radiation, a photoresist for X ray, and a photoresist for electron beam. Examples of a photoresist for light exposure include photoresists including cyclized rubber, polycinnamic acid, and novolac resin as major ingredients. As a photoresist for ultraviolet radiation, cyclized rubber, phenol resin, polymethylisopropenylketone (PMIPK), polymethylmethacrylate (PMMA), or the like is used. As a photoresist for x ray, COP, methacrylate, or the like can be used. As a photoresist for electron beam, the above-described substances, such as PMMA or the like, can be used.

"Chip" as used herein refers to an ultramicro-integrated circuit having various functions, which constitutes a part of a system. "Biomolecule chip" as used herein refers to a chip comprising a substrate and a biomolecule, in which at least one biomolecule as set forth herein is disposed on the substrate.

The term "address" as used herein refers to a unique position on a substrate which can be distinguished from other unique positions. An address is suitably used to access to a biomolecule associated with the address. Any entity present at each address can have an arbitrary shape which allows the entity to be distinguished from entities present at other addresses (e.g., in an optical manner). The shape of an address maybe, for example, a circle, an ellipse, a square, or a rectangle, or alternatively an irregular shape.

The size of each address varies depending on, particularly, the size of a substrate, the number of addresses on the specific substrate, the amount of samples to be analyzed and/or an available reagent, the size of a biomolecule, and the magnitude of a resolution required for any method in which the array is used. The size of an address may range from 1-2 nm to several centimeters (e.g., 1-2 mm to several centimeters, etc., 125×80 mm, 10×10 mm, etc.). Any size of an address is possible as long as it matches the array to which it is applied. In such a case, a substrate material is formed into a size and a shape suitable for a specific production process and application of an array. For example, in the case of analysis where a large amount of samples to be measured are available, an array may be more economically constructed on a relatively large substrate (e.g., 1 cm×1 cm or more) . Here, a detection system which does not require sensitivity much and is therefore economical may be further advantageously used. On the other hand, when the amount of an available sample to be analyzed and/or reagent is limited, an array may be designed so that consumption of the sample and reagent is minimized.

The spatial arrangement and forms of addresses are designed in such a manner as to match a specific application in which the microarray is used. Addresses maybe densely loaded, widely distributed, or divided into subgroups in a pattern suitable for a specific type of sample to be analyzed. "Array" as used herein refers to a pattern of solid substances fixed on a solid phase surface or a film, or a group of molecules having such a pattern. Typically, an array comprises biomolecules (e.g., DNA, RNA, protein-RNA fusion molecules, proteins, low-weight organic molecules, etc.) conjugated to nucleic acid sequences fixed on a solid phase surface or a film as if the biomolecule captured the nucleic sequence. "Spots" of biomolecules may be arranged on an array. "Spot" as used herein refers to a predetermined set of biomolecules.

Any number of addresses may be arranged on a substrate, typically up to $10^8$ addresses, in other embodiments up to $10^7$ addresses, up to $10^6$ addresses, up to $10^5$ addresses, up to $10^4$ addresses, up to $10^3$ addresses, or up to $10^2$ addresses. Therefore, when one biomolecule is placed on one address, up to $10^8$ biomolecules can be placed on a substrate, and in other embodiment up to $10^7$ biomolecules, up to $10^6$ biomolecules, up to $10^5$ biomolecules, up to $10^4$ biomolecules, up to $10^3$ biomolecules, or up to $10^2$ biomolecules can be placed on a substrate. In these cases, a smaller size of substrate and a smaller size of address are suitable. In particular, the size of an address may be as small as the size of a single biomolecule (i.e., this size may be of the order of 1-2 nm). In some cases, the minimum area of a substrate is determined based on the number of addresses on the substrate.

The term "biomolecule" as used herein refers to a molecule related to, an organism. An "organism" as used herein refers to a biological organic body, including, but being limited to, an animal, a plant, a fungus, a virus, and the like. A biomolecule includes a molecule extracted from an organism, but is not so limited. A biomolecule is any molecule capable of having an influence on an organism. Therefore, a biomolecule also includes a molecule synthesized by combinatorial chemistry, and a low weight molecule capable of being used as a medicament (e.g., a low molecular weight ligand, etc.) as long as they are intended to have an influence on an organism. Examples of such a biomolecule include, but are not limited to, proteins, polypeptides, oligopeptides, peptides, polynucleotides, oligonucleotides, nucleotides, nucleic acids (e.g., including DNA (such as cDNA and genomic DNA) and RNA (such as mRNA)), polysaccharides, oligosaccharides, lipids, low weight molecules (e.g., hormones, ligands, signal transduction substances, low-weight organic molecules, etc.), and complex molecules thereof, and the like. A biomolecule also includes a cell itself, and a part or the whole of tissue, and the like as long as they can be coupled to a substrate of the present invention. Preferably, a biomolecule includes a nucleic acid or a protein. In a preferable embodiment, a biomolecule is a nucleic acid (e.g., genomic DNA or cDNA, or DNA synthesized by PCR or the like). In another preferable embodiment, a biomolecule may be a protein. Preferably, one type of biomolecule may be provided for each address on a substrate of the present invention. In another embodiment, a sample containing two or more types of biomolecules may be provided for each address.

The term "protein", "polypeptide", "oligopeptide" and "peptide" as used herein have the same meaning and refer to an amino acid polymer having any length. This polymer may be a straight, branched or cyclic chain. An amino acid may be a naturally-occurring or non-naturally-occurring amino acid, or a variant amino acid. The term may be assembled into a complex of a plurality of polypeptide chains. The term also includes a naturally-occurring or artificially modified amino acid polymer. Such modification includes, for example, disulfide bond formation, glycosylation, lipidation, acetylation, phosphorylation, or any other manipulation or modification (e.g., conjugation with a labeling component). This definition encompasses a polypeptide containing at least one amino acid analog (e.g., non-naturally-occurring amino acid, etc.), a peptide-like compound (e.g., peptoid), and other variants known in the art, for example.

The terms "polynucleotide", "oligonucleotide", and "nucleic acid" as used herein have the same meaning and refer to a nucleotide polymer having any length. This term also includes an "oligonucleotide derivative" or a "polynucleotide derivative". An "oligonucleotide derivative" or a "polynucleotide derivative" includes a nucleotide derivative, or refers to an oligonucleotide or a polynucleotide having different linkages between nucleotides from typical linkages, which are interchangeably used. Examples of such an oligonucleotide specifically include 2'-O-methyl-ribonucleotide, an oligonucleotide derivative in which a phosphodiester bond in an oligonucleotide is converted to a phosphorothioate bond, an oligonucleotide derivative in which a phosphodiester bond in an oligonucleotide is converted to a N3'-P5' phosphoroamidate bond, an oligonucleotide derivative in which a ribose and a phosphodiester bond in an oligonucleotide are converted to a peptide-nucleic acid bond, an oligonucleotide derivative in which uracil in an oligonucleotide is substituted with C-5 propynyl uracil, an oligonucleotide derivative in which uracil in an oligonucleotide is substituted with C-5 thiazole uracil, an oligonucleotide derivative in which cytosine in an oligonucleotide is substituted with C-5 propynyl cytosine, an oligonucleotide derivative in which cytosine in an oligonucleotide is substituted with phenoxazine-modified cytosine, an oligonucleotide derivative in which ribose in DNA is substituted with 2'-O-propyl ribose, and an oligonucleotide derivative in which ribose in an oligonucleotide is substituted with 2'-methoxyethoxy ribose.

"Gene" as used herein refers to a factor defining a genetic trait. A gene is typically arranged in a certain sequence on a chromosome. A gene which defines the first-order structure of a protein is called a structural gene. A gene which regulates the expression of a structural gene is called a regulatory gene. A "gene" as used herein may refer to a "polynucleotide", an "oligonucleotide" and a "nucleic acid", and/or a "protein", a "polypeptide", an "oligopeptide" and a "peptide". As used herein, "homology" of a gene refers to the magnitude of identity between two or more gene sequences. Therefore, the greater the homology between two certain genes, the greater the identity or similarity between their sequences. Whether or not two genes have homology is determined by comparing their sequences directly or by a hybridization method under stringent conditions. When two gene sequences are directly compared with each other, the genes have representatively at least 50% homology, preferably at least 70% homology, more preferably at least 80%, 90%, 95%, 96%, 97%, 98%, or 99% homology with the DNA sequence of the genes are identical.

The term "polysaccharide", "complex carbohydrate", "oligosaccharide", "sugar", and "carbohydrate" have the same meaning and refer to a polymer compound in which monosaccharides are dehydrocondensed by glycoside bonds. "Simple sugar" or "monosaccharide" refers to a substance represented by the general formula $C_nH_{2n}O_n$, which cannot be decomposed by hydrolysis to a simpler molecule. $C_nH_{2n}O_n$ where n=2, 3, 4, 5, 6, 7, 8, 9 and 10, represent diose, triose, tetrose, pentose, hexose, heptose, octose, nonose, and decose, respectively. Monosaccharide generally corresponds to an aldehyde or ketone of chain polyhydric alcohol, the former being called aldose and the latter being called ketose.

A biomolecule of the present invention may be collected from an organism or may be chemically synthesized by a method known to those skilled in the art. For example, a synthesis method using an automated solid phase peptide synthesizer is described in the following: Stewart, J. M. et al. (1984). Solid Phase Peptide Synthesis, Pierce Chemical Co.; Grant, G. A. (1992) Synthetic Peptides: A User's Guide, W. H. Freeman; Bodanszky, M. (1993). Principles of Peptide Synthesis, Springer-Verlag; Bodanszky, M. et al. (1994). The Practice of Peptide Synthesis, Springer-Verlag; Fields, G. B. (1997). Phase Peptide Synthesis, Academic Press; Pennington, M. W. et al. (1994). Peptide Synthesis Protocols, Humana Press; Fields, G. B. (1997). Solid-Phase Peptide Synthesis, Academic Press. An oligonucleotide may be prepared by automated chemical synthesis using any DNA synthesizer commercially available from Applied Biosystems or the like. A composition and a method for automated oligonucleotide synthesis are disclosed in, for example, U.S. Pat. No. 4,415,732, Caruthers et al. (1983); U.S. Pat. No. 4,500,707, Caruthers (1985); and U.S. Pat. No. 4,668,777, Caruthers et al. (1987).

In one embodiment of the present invention, a library of biomolecules (e.g., low-weight organic molecules, combinatorial chemistry products) may be coupled to a substrate, and a resultant substrate can be used to produce a microarray for screening of molecules. A compound library used in the present invention can be prepared or obtained by any means including, but not limited to, a combinatorial chemistry technique, a fermentation method, extraction procedures from plants and cells, or the like. A method for producing a combinatorial library is well known in the art. See, for example, E. R. Felder, Chimica 1994, 48, 512-541; Gallop et al., J. Med. Chem. 1994, 37, 1233-1251; R. A. Houghten, Trends Genet. 1993, 9, 235-239; Houghten et al., Nature 1991, 354, 84-86; Lam et al., Nature 1991, 354, 82-84; Carell et al., Chem. Biol. 1995, 3, 171-183; Madden et al., Perspectives in Drug Discovery and Design2, 269-282; Cwirla et al., Biochemistry 1990, 87, 6378-6382; Brenner et al., Proc. Natl. Acad. Sci. USA 1992, 89, 5381-5383; Gordon et al., J. Med. Chem. 1994, 37, 1385-1401; Lebl et al., Biopolymers 1995, 37 177-198; and literature cited therein. These publications are herein incorporated by reference in their entirety.

"Stringent conditions" as used herein refers to widely used and well known conditions in the art concerning hybridization. Such conditions are, for example, the following: hybridization is conducted in the presence of 0.7 to 1.0 M NaCl at 65° C., and thereafter, 0.1 to 2-fold concentration SSC (saline-sodium citrate) solution (1-fold concentration SSC solution has a composition of 150 mM sodium Chloride, 15 mM sodium citrate) is used to wash a filter at 65° C. Hybridization can be conducted in accordance with a method described in an experimental manual, such as Molecular Cloning. 2nd ed., Current Protocols in Molecular Biology, Supplement 1-38, DNA Cloning 1: Core Techniques, A Practical Approach, Second Edition, Oxford University Press (1995), or the like.

Comparison in identity between base sequences is herein calculated by a sequence analyzing tool, BLAST, using default parameters.

A method, biomolecule chip and apparatus of the present invention may be used in, for example, diagnosis, forensic medicine, drug search (medicament screening) and development, molecular biological analysis (e.g., array-base nucleotide sequence analysis and array-base gene sequence analysis), analysis of protein properties and functions, pharmacogenomics, proteomics, environmental assessment, and other biological and chemical analysis.

A method, biomolecule chip and apparatus of the present invention may be used in the detection of various genes. A gene to be detected is not particularly limited. Examples of such a gene to be detected include genes of viral pathogens (including, but not limited to, hepatitis viruses (type A, B, C, D, E, F, and G), HIV, influenza viruses, herpes viruses, adenovirus, human polyoma virus, human Papilloma virus, human Parvovirus, mumps virus, human rotavirus, Enterovirus, Japanese encephalitis virus, denguevirus, rubella virus, and HTLV); genes of bacterial pathogens (including, but not limited to, *Staphylococcus aurens, Hemolytic streptococcus*, virulent *Escherichia coli, enteritis vibrio, Helicobacter pylori, Campylobacter, Vibrio cholerae, dysentery bacillus, Salmonella, Yersinia, gunococcus, Listeria monocytogenes, Leptospira, Legionella, Spirochaeta, Mycoplasma pneumoniae, Rickettsia*, and *Chlamydia*), and genes of *Entamoeba histolytica*, pathogenic fungi, parasites, and fungi.

A method, biomolecule chip and apparatus of the present invention may be used in detection and diagnosis for neoplastic diseases, such as hereditary diseases, retinoblastoma, Wilms' tumor, familial colonic polyposis, neurofibromatosis, familial breast cancer, xeroderma pigmentosum, brain tumor, cancer of the oral cavity, esophageal cancer, stomach cancer, colon cancer, liver cancer, pancreas cancer, lung cancer, thyroid tumor, tumor of the mammary gland, tumor of urinary organs, tumor of male organs, tumor of female organs, skin tumor, tumor of bones and soft parts, leukemia, lymphoma, solid tumor, and the like.

The present invention can also be applied to polymorphism analysis, such as RFLP analysis, single nucleotide polymorphism (SNP) analysis, or the like, analysis of base sequences, and the like. The present invention can also be used for screening of a medicament.

The present invention can be applied to any situation requiring a biomolecule test other than medical applications, such as food testing, quarantine, medicament testing, forensic medicine, agriculture, husbandry, fishery, forestry, and the like. The present invention is also intended to be used particularly for the purposes of safety of foods (BSE test).

The present invention may be used to obtain biochemical test data. Examples of items of biochemical tests include, but are not limited to, total protein, albumin, thymol reaction, Kunkel's zinc sulfate testing, plasma ammonia, urea nitrogen, creatinine, uric acid, total bilirubin, direct reacting bilirubin, GOT, GPT, cholinesterase, alkaline phosphatase, leucine aminopeptidase, γ-glutamyl transpeptidase, creatinine phosphakinase, lactic dehydrogenase, amylase, sodium, potassium, chloride ion (chlor), total calcium, inorganic phosphor, serum iron, unsaturated iron-binding capability, serum osmotic pressure, total cholesterol, free cholesterol, HDL-cholesterol, triglyceride, phospholipid, free fatty acid, plasma glucose, insulin, BSP retention ratio, ICG disappearance ratio, ICG retention ratio, spinal fluid total protein, spinal fluid sugar, spinal fluid chlorine, urine total protein, urine glucose, urine amylase, urine ureic acid, urine urea nitrogen, urine creatinine, urine calcium, urine osmotic pressure, urine inorganic phosphor, urine sodium, urine potassium, urine chlor, N-acetylglucosaminidase in urine, 1-hour creatinine clearance, 24-hour creatinine clearance, phenolsulfonephthalein, C-reactive protein, and the like. A method and principle for measuring these test items are well known and commonly used in the art.

The present invention can also be used for detection of a gene amplified by PCR, SDA, NASBA, or the like, other than a sample directly collected from an organism. In the present invention, a target gene can be labeled in advance with an electrochemically active substance, a fluorescent substance (e.g., FITC, rhodamine, acridine, Texas Red, fluorecein, etc.), an enzyme (e.g., alkaline phosphatase, peroxidase, glucose oxidase, etc.), a colloid particle (e.g., a hapten, a light-emitting substance, an antibody, an antigen, gold colloid, etc.), a metal, a metalion, a metal chelate (e.g., trisbipyridine, trisphenanthroline, hexamine, etc.), or the like.

In the present invention, a sample to be tested or diagnosed is not particularly limited and includes, for example, blood, serum, leukocytes, urine, stool, semen, saliva, tissue, cultured cells, sputum, and the like.

In one embodiment, a nucleic acid component is extracted from these samples in order to test nucleic acid. The extraction is not limited to a particular method. A liquid-liquid extraction method, such as phenol-chloroform method and the like, or a liquid-solid extraction method using a carrier can be used. Alternatively, a commercially available nucleic acid extraction method QIAamp (QIAGEN, Germany) or the like can be used. Next, a sample containing an extracted nucleic acid component is subjected to a hybridization reaction on a biomolecule chip of the present invention. The reaction is conducted in a buffer solution having an ionic strength of 0.01 to 5 and a pH of 5 to 10. To this solution may be added dextran sulfate (hybridization accelerating agent), salmon sperm DNA, bovine thymus DNA, EDTA, a surfactant, or the like. The extracted nucleic acid component is added to the solution, followed by heat denaturation at 90° C. or more. Insertion of a biomolecule chip can be carried out immediately after denaturation or after rapid cooling to 0° C. Alternatively, a hybridization reaction can be conducted by dropping a solution on a substrate. The rate of a reaction can be increased by stirring or shaking during the reaction. The temperature of a reaction is in the range of 10° C. to 90° C. The time of a reaction is in the range of one minute to about one night. After a hybridization reaction, an electrode is removed and then washed. For washing, a buffer solution having an ionic strength of 0.01 to 5 and a pH of 5 to 10 can be used.

"Microcapsule" as used herein refers to a microparticle enveloping a substance with a molecular membrane or the like, or its container-like substance. A microcapsule usually has a spherical shape and a size of several micrometers to several hundred micrometers. In general, a microcapsule can be prepared as follows. A water droplet-in-water type emulsion is produced, and a polymer thin film is produced by interfacial polycondensation at an interface between the micro-emulsion particle and a medium so that the particle is covered with the thin film. The capsule is isolated from the oil by centrifugation, followed by dialysis for purification. When an emulsion is prepared, an intended biomolecule is dissolved and dispersed into a water phase, so that the biomolecule can be enveloped in a capsule. The thickness of the thin film is 10 to 20 μm. The thin film can be provided with semipermeability or surface charge. In the present invention, a microcapsule protects and isolates content, such as a biomolecule. Such content can be optionally dissolved, mixed or allowed to react. In a method for producing a biomolecule substrate according to the present invention, a microcapsule is sprayed onto a substrate by an ink jet method (e.g., Bubble Jet®, etc.), a PIN method, or the like. The sprayed microcapsule is heated to a temperature higher than the melting point of its shell so that content, such as a biomolecule, can be immobilized on the substrate. In this case, the substrate is preferably coated with a substance having an affinity for the biomolecule.

"Label" and "mark" as used herein have the same meaning and refer to an entity which distinguishes an intended molecule or substance from other substances (e.g., a substance, energy, electromagnetic wave, etc.). Examples of such a labeling method include an RI (radioisotope) method, a fluorescence method, a biotin method, a chemiluminescence method, and the like. When both a nucleic acid fragment and its complementary oligonucleotide are labeled by a fluorescence method, they are labeled with fluorescence substances having different maximum wavelengths of fluorescence. The difference in the maximum wavelength of fluorescence is preferably at least 10 nm. Any fluorescence substance which can bind to a base portion of nucleic acid can be used. Preferable fluorescence substances include cyanine dye (e.g., Cy3, Cy5, etc. in Cy Dye™ series), a rhodamine 6G reagent, N-acetoxy-N-2-acetylaminofluorene. (AAF), AAIF (an iodine derivative of AAF), and the like. Examples of a combination of fluorescence substances having a difference in the maximum wavelength of fluorescence of at least 10 nm include a combination of Cy5 and a rhodamine 6G reagent, a combination of Cy3 and fluorescein, a combination of a rhodamine 6G reagent and fluorescein, and the like.

"Chip attribute data" as used herein refers to data associated with some information relating to a biomolecule chip of the present invention. Chip attribute data includes information associated with a biomolecule chip, such as a chip ID, substrate data, and biomolecule attribute data. "Chip ID" as used herein refers to a code for identification of each chip. "Substrate data" or "substrate attribute data" as used herein refers to data relating to a substrate used in a biomolecule chip of the present invention. Substrate data may contain information relating to an arrangement or pattern of a biomolecule. "Biomolecule attribute data" refers to information relating to a biomolecule, including, for example, the gene sequence of the biomolecule (a nucleotide sequence in the case of nucleic acid, and an amino acid sequence in the case of protein), information relating to a gene sequence (e.g., a relationship between the gene and a specific disease or condition), a function in the case of a low weight molecule or a hormone, library information in the case of a combinatorial library, molecular information relating to affinity for a low weight molecule, and the like. "Personal information data" as used herein refers to data associated with information for identifying an organism or subject to be measured by a method, chip or apparatus of the present invention. When the organism or subject is a human, personal information data includes, but is not limited to, age, sex, health condition, medical history (e.g., drug history), educational background, the company of your insurance, personal genome information, address, name, and the like. When personal information data is of a domestic animal, the information may include data about the production company of the animal. "Measurement data" as used herein refers to raw data as a result of measurement by a biomolecule substrate, apparatus and system of the present invention and specific processed data derived therefrom. Such raw data may be represented by the intensity of an electric signal. Such processed data may be specific biochemical data, such as a blood sugar level and a gene expression level.

"Recording region" as used herein refers to a region in which data may be recorded. In a recording region, measurement data as well as the above-described chip attribute data can be recorded.

In a preferable embodiment of the present invention, personal information data and biomolecule attribute data or measurement data may be separately managed. By managing these data separately, the secrecy of health-related information, i.e., personal privacy, can be protected. Moreover, in the case of medicament screening, even if screening is farmed out to an outside company, data can be obtained without leaking to secret information to the outside company. Therefore, the present invention can be applied to outsourcing in which secret information is protected.

General Techniques

Techniques as used herein are well known techniques commonly used in microfluidics, micromachining, organic chemistry, biochemistry, genetic engineering, molecular biology, genetics, and their related fields with in the technical scope of the art, unless otherwise specified. These techniques are sufficiently described in, for example, literature listed below and described elsewhere herein.

Micromachining is described in, for example, Campbell, S. A. (1996). The Science and Engineering of Microelectronic Fabrication, Oxford University Press; Zaut, P. V. (1996). Micromicroarray Fabrication: a Practical Guide to Semiconductor Processing, Semiconductor Services; Madou, M. J. (1997). Fundamentals of Microfabrication, CRC1 5 Press; Rai-Choudhury, P. (1997). Handbook of Microlithography, Micromachining, & Microfabrication: Microlithography; and the like, related portions of which are herein incorporated by reference.

Molecular biology and recombinant DNA techniques are described in, for example, Maniatis, T. et al. (1982). Molecular Cloning: A Laboratory Manual, Cold Spring Harbor; Ausubel, F. M. (1987). Current Protocols in Molecular Biology, Greene Pub. Associates and Wiley-Interscience; Ausubel, F. M. (1989). Short Protocols in Molecular Biology: A Compendium of Methods from Current Protocols in Molecular Biology, Greene Pub. Associates and Wiley-Interscience; Sambrook, J. et al. (1989). Molecular Cloning: A Laboratory Manual, Cold Spring Harbor; Innis, M. A. (1990). PCR Protocols: A Guide to Methods and Applications, Academic Press; Ausubel, F. M. (1992). Short Protocols in Molecular Biology: A Compendium of Methods from Current Protocols in Molecular Biology, Greene Pub. Associates; Ausubel, F. M. (1995). Short Protocols in Molecular Biology: A Compendium of Methods from Current Protocols in Molecular Biology, Greene Pub. Associates; Innis; M. A. et al. (1995). PCR Strategies, Academic Press; Ausubel, F. M. (1999). Short Protocols in Molecular Biology: A Compendium of Methods from Current Protocols in Molecular Biology, Wiley, and annual updates; Sninsky, J. J. et al. (1999). PCR Applications: Protocols for Functional Genomics, Academic Press; and the like, related portions of which are herein incorporated by reference.

Nucleic acid chemistry, such as DNA synthesis techniques and the like, is described in, for example, Gait, M. J. (1985). Oligonucleotide Synthesis: A Practical Approach, IRL Press; Gait, M. J. (1990). Oligonucleotide Synthesis: A Practical Approach, IRL Press; Eckstein, F. (1991). Oligonucleotides and Analogues: A Practical Approach, IRL Press; Adams, R. L. et al. (1992). The Biochemistry of the Nucleic Acids, Chapman & Hall; Shabarova, Z. et al. (1994). Advanced Organic Chemistry of Nucleic Acids, Weinheim; Blackburn, G. M. et al. (1996). Nucleic Acids in Chemistry and Biology, Oxford University Press; Hermanson, G. T. (1996). Bioconjugate Techniques, Academic Press; and the like, related portions of which are herein incorporated by reference.

Photolithography is a technique developed by Fodor et al., in which a photoreactive protecting group is utilized (see Science, 251, 767 (1991)). A protecting group for a base inhibits a base monomer of the same or different type from binding to that base. Thus, a base terminus to which a protecting group is bound has no new base-binding reaction. A protecting group can be easily removed by irradiation. Initially, amino groups having a protecting group are immobilized throughout a substrate. Thereafter, only spots to which a desired base is to be bound are selectively irradiated by a method similar to a photolithography technique usually used in a semiconductor process, so that another base can be introduced by subsequent binding into only the bases in the irradiated portion. Now, desired bases having the same protecting group at a terminus thereof are bound to such bases. Thereafter, the pattern of a photomask is changed, and other spots are selectively irradiated. Thereafter, bases having a protecting group are similarly bound to the spots. This process is repeated until a desired base sequence is obtained in each spot, thereby preparing a DNA array. Photolithography techniques may be herein used.

An ink jet method (technique) is a technique of projecting considerably small droplets onto a predetermined position on a two-dimensional plane using heat or a piezoelectric effect. This technique is widely used mainly in printers. In production of a DNA array, an ink jet apparatus is used, which has a configuration in which a piezoelectric device is combined with a glass capillary. A voltage is applied to the piezoelectric device which is connected to a liquid chamber, so that the volume of the piezoelectric device is changed and the liquid within the chamber is expelled as a droplet from the capillary connected to the chamber. The size of the expelled droplet is determined by the diameter of the capillary, the volume variation of the piezoelectric device, and the physical property of the liquid. The diameter of the droplet is generally 30 µm. An ink jet apparatus using such a piezoelectric device can expel droplets at a frequency of about 10 kHz. In a DNA array fabricating apparatus using such an ink jet apparatus, the ink jet apparatus and a DNA array substrate are relatively moved so that droplets can be dropped onto desired spots on the DNA array. DNA array fabricating apparatuses using an ink jet apparatus are roughly divided into two categories. One category includes a DNA array fabricating apparatus using a single ink jet apparatus, and the other includes a DNA array fabricating apparatus using a multi-head ink jet apparatus. The DNA array fabricating apparatus with a single ink jet apparatus has a configuration in which a reagent for removing a protecting group at a terminus of an oligomer is dropped onto desired spots. A protecting group is removed from a spot, to which a desired base is to be introduced, by using the ink jet apparatus so that the spot is activated. Thereafter, the desired base is subjected to a binding reaction throughout a DNA array. In this case, the desired base is bound to only spots having an oligomer whose terminus is activated by the reagent dropped from the ink jet apparatus. Thereafter, the terminus of a newly added base is protected. Thereafter, a spot from which a protecting group is removed is changed and the procedures are repeated until desired nucleotide sequences are obtained. On the other hand, in a DNA array fabricating apparatus using a multi-head ink jet apparatus, an ink jet apparatus is provided for each reagent containing a different base, so that a desired base can be bound directly to each spot. A DNA array fabricating apparatus using a multi-head ink jet apparatus can have a higher throughput than that of a DNA array fabricating apparatus using a single ink jet apparatus. Among methods for fixing a presynthesized oligonucleotide to a substrate is a mechanical microspotting technique in which liquid containing an oligonucleotide, which is attached to the tip of a stainless pin, is mechanically pressed against a substrate so that the oligonucleotide is immobilized on the substrate. The size of a spot obtained by this method is 50 to 300 µm. After microspotting, subsequent processes, such as immobilization using UV light, are carried out.

BEST MODE FOR CARRYING OUT THE INVENTION

In one aspect, the present invention provides a method for fabricating a biomolecule substrate. This method comprises the steps of: 1) providing a set of biomolecules and a substrate; 2) enclosing the set of biomolecules into microcapsules on the biomolecule-type-by-biomolecule-type basis; and 3) spraying the biomolecule microcapsules onto the substrate. Preferably, the set of biomolecules are uniform. In a preferred embodiment, the method provides a plurality of sets of biomolecules. Preferably, the microcapsules of the set of biomolecules of different types are disposed at different positions. In one embodiment, the present invention may further comprise the step of washing the biomolecule microcapsules after the enclosing step.

The spraying step used in the method of the present invention is performed by an ink jet method (including a Bubble Jet® method), a PIN method, or the like. Preferably, the spraying step may be performed by a Bubble Jet® method. This is because the microcapsules may be efficiently immobilized.

In a preferred embodiment, the method may further comprise the step of setting the temperature of a solution used in the spraying step to be higher than the melting point of a shell of the biomolecule microcapsulate. Such an increased temperature of the solution can lead to efficient immobilization of the biomolecules.

In this biomolecule substrate fabrication method, the biomolecule may be a naturally-occurring or synthetic biomolecule. Examples of such a biomolecule include, but are not limited to, a protein, a polypeptide, an oligopeptide, a peptide, a polynucleotide, an oligonucleotide, a nucleotide, nucleic acid (e.g., including DNA, such as cDNA or genomic DNA, and RNA, such as mRNA), a polysaccharide, an oligosaccharide, lipid, a low weight molecule (e.g., a hormone, a ligand, a signal transduction substance, a low-weight organic molecule, etc.), and composite molecules thereof.

Preferably, the biomolecule substrate fabrication method of the present invention may further comprise the step of perform labeling specific to each microcapsule.

In another aspect, the present invention provides a biomolecule chip. This biomolecule chip comprises: a substrate; and biomolecules and chip attribute data arranged on the substrate. The chip attribute data is arranged in the same region as that of the biomolecules. By placing the biomolecules and the chip attribute data in the same region, an efficient testing can be performed.

In one embodiment, the above-described chip attribute data may contain information relating to chip ID and the substrate. In another embodiment, the biomolecule chip of the present invention may further comprise a recording region, wherein the recording region is placed on the same substrate as that of the biomolecule and the chip attribute data, and at least one of the subject data and measurement data is recorded in the recording region. Preferably, both the subject data and measurement data may be recorded in the above-described recording region. Note that when it is intended to protect privacy depending on the purpose, only a part of these pieces of information may be recorded in the recording region. In this case, such data may be encrypted and then recorded.

Preferably, the above-described chip attribute data may be recorded in such a manner that the data can be read out by the same means as that for detecting the above-described biomolecule. Examples of such detection means include, but are not limited to, any means capable of detecting the biomolecule, such as a fluorescence analysis apparatus, a spectrophotometer, a scintillation counter, and a luminometer. Since both the chip attribute data and the biomolecule can be read out by the same detection means, both testing of raw data and reading of measurement conditions can be performed by a single readout operation, thereby making it possible to significantly reduce an operation time and simplifying signal sending and receiving equipment.

In a preferred embodiment, a specific mark may be attached to the above-described substrate. By attaching the specific mark to the substrate, identification of the substrate can be double-checked, thereby making it possible to reduce diagnosis and testing errors. In another preferred embodiment, the specific mark is arranged based on the chip attribute data. By providing such a specific mark, it is possible to easily read out chip attribute data.

In another embodiment, the above-described chip attribute data may contain the above-described biomolecule attribute data. By adding the biomolecule attribute data to the biomolecule chip, various tests and diagnoses can be performed by using only the chip. In another embodiment, this chip attribute data can be maintained in another site. By maintaining the data in another site, personal information can be prevented from being unintentionally leaked even when the biomolecule chip is unintentionally passed to a third party.

In another embodiment, information relating to an address of the above-described biomolecule may be further recorded. Examples of such address information include geometric information of an arrangement or a pattern defined in the present invention. By adding address-related information to the biomolecule chip, a stand-alone test can be performed. The address-related information can also be maintained in another site. By maintaining the information in another site, personal information can be prevented from being unintentionally leaked even when the biomolecule chip is unintentionally passed to a third party. In a preferred embodiment, the address may be a tracking address.

In a further preferred embodiment, the above-described chip attribute data may be encrypted. The whole or a part of the data may be encrypted. Preferably, personal information data, biomolecule attribute data, and measurement data may be encrypted. These data may be encrypted by separate encryption means. Such an encryption means is well known in the art, including, for example, a means using a public key. The present invention is not so limited.

In another embodiment, data relating to a label used to detect the biomolecule may be recorded. Examples of such a label include, but are not limited to, any substance for labeling a biomolecule, such as, for example, a fluorescent molecule, a chemoluminescent molecule, a radioactive isotope, and the like. By providing such label-related data, a test or diagnosis can be performed by using only a biomolecule chip. Preferably, the label-related data contains at least one of the wavelength of excited light and the wavelength of fluorescence, and more preferably both of them.

The biomolecule used in the biomolecule chip of the present invention may be a naturally occurring or synthetic biomolecule. Examples of such a biomolecule include, but are not limited to, a protein, a polypeptide, an oligopeptide, a peptide, a polynucleotide, an oligonucleotide, a nucleotide, nucleic acid (e.g., including DNA, such as cDNA or genomic DNA, and RNA, such as mRNA), a polysaccharide, an oligosaccharide, lipid, a low weight molecule (e.g., a hormone, a ligand, a signal transduction substance, a low-weight organic molecule, etc.), and composite molecules thereof. Preferably, the biomolecule may be a nucleic acid or a protein, and more preferably DNA (e.g., cDNA or genomic DNA). In another preferred embodiment, the biomolecule may be DNA amplified by an amplification means, such as PCR or the like. In another preferred embodiment, the biomolecule may be a synthesized protein.

Figure 47:
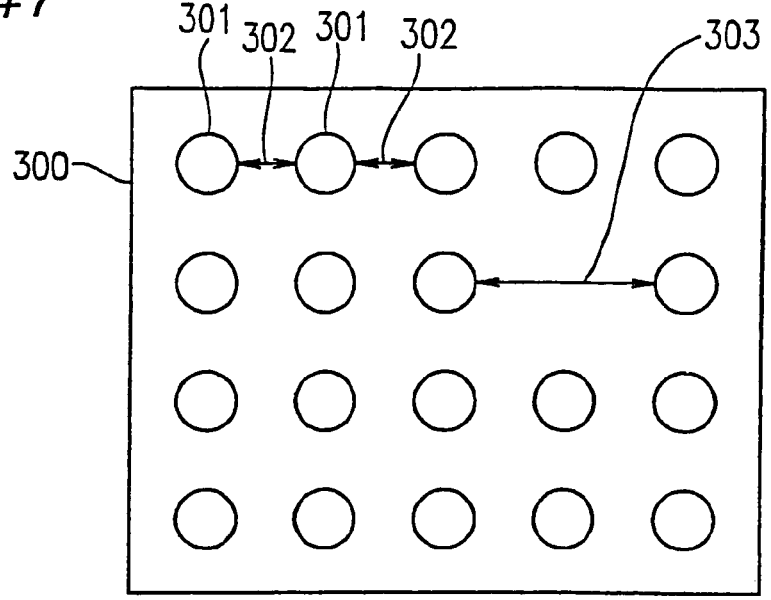

In another aspect, the present invention provides a biomolecule chip comprising: 1) a substrate; and 2) biomolecules arranged on the substrate, wherein spots of the biomolecules are spaced by at least one non-equal interval, an address of the biomolecule spot can be identified from the non-equal interval. By providing at least one non-equal interval, the interval can be used as a reference to identify the relative positions of other spots. With this structure, it is possible to identify the address of a spot having interaction only by the steps of detecting all biomolecules and detecting a spot after contacting a sample, without a step of identifying the position of the spot. Such an address identifying method is also herein called address identification using specific "arrangement". FIG. 47 shows an example of address identification using specific arrangement. In FIG. 47, biomolecules are spaced at equal intervals as indicated by 302, except that at least one interval between biomolecules is a non-equal interval as indicated by 303. When this non-equal interval is used as a starting point, the address of any spot can be identified.

Preferably, the non-equal interval is modulated. Modulation as used herein refers to variations in spot interval. Modulation may be either regular or irregular. An example of such modulation is a sequence of 00, 01, 10, 00, 01, 01, 01 in the binary number system. The present invention is not so limited. By changing modulation, more efficient address identification can be made possible.

In a certain embodiment, the above-described non-equal intervals may be present in at least two directions. Preferably, the non-equal intervals in the two directions may be distinguished from each other. By using the non-equal intervals in at least two directions, address can be reliably identified even if data is read out in the case when the substrate is turned upside down. Preferably, a plurality of such non-equal intervals may be present. Moreover, such non-equal intervals can be scattered on a substrate.

Figure 48:
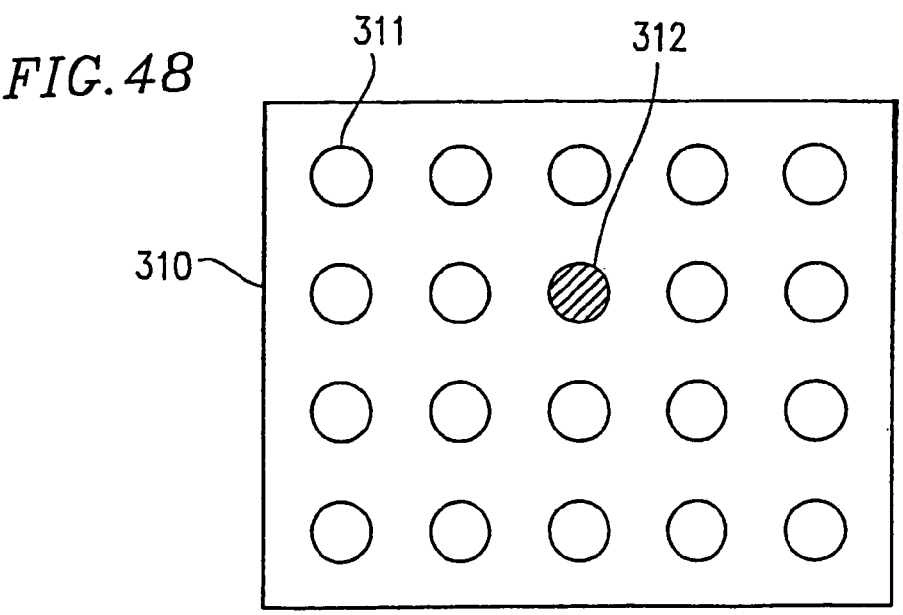

In another embodiment, the present invention provides a biomolecule chip comprising: 1) a substrate; and 2) biomolecules arranged on the substrate, wherein the biomolecules include a distinguishable first biomolecule and a distinguishable second biomolecule, an address of the biomolecule can be identified based on an arrangement of spots of the first biomolecules and spots of the second biomolecule. By providing at least two types of distinguishable biomolecules, it is possible to identify the address of a spot having interaction only by the steps of detecting all biomolecules and detecting a spot after contacting a sample, without a step of identifying the position of the spot. Such an address identifying method is also called address identification using a specific "pattern". FIG. 48 shows an example of address identification using a specific pattern. In FIG. 48, a first biomolecule 311 can be distinguished from a second biomolecule 312. In this example, by using the second biomolecule 312 as a starting point, the address of any spot can be identified.

"Distinguishable" as used herein indicates that identification can be carried out by at least one detection means (including, not limited to, the naked eye, a fluorescence measurement apparatus, a spectrophotometer, a radiation measurement apparatus, etc.). Therefore, a distinguishable biomolecule may be, for example, a molecule which can be identified by the naked eye, or a molecule which emits different fluorescence when it is excited. "Distinguishable" also indicates that identification can be carried out by the same label having a different level (e.g. a difference in the amount of dye, etc.).

In one embodiment of the biomolecule chip of the present invention in which an address is identified by a specific arrangement or a specific pattern, a label distinguishable from the biomolecule may be placed between the biomolecule spots. Such a label may be any label as defined herein, and preferably a label which can be detected by the same detection means as the above-described means for detecting a biomolecule.

In one embodiment of the biomolecule chip of the present invention in which an address is identified by a specific arrangement or a specific pattern, the above-described distinguishable label can be detected by a detection means. Examples of such detection means include, but are not limited to, any means capable of detecting the biomolecule, such as a fluorescence analysis apparatus, a spectrophotometer, a scintillation counter, and a luminometer.

In one embodiment of the biomolecule chip of the present invention in which an address is identified by a specific arrangement or a specific pattern, the label may be arranged in a horizontal direction and a vertical direction on the substrate.

In one embodiment of the biomolecule chip of the present invention in which an address is identified by a specific arrangement or a specific pattern, a synchronization mark may be arranged. By providing a synchronization mark, address identification is made easier.

A biomolecule used in one embodiment of the biomolecule chip of the present invention in which an address is identified by a specific arrangement or a specific pattern may be a naturally-occurring or synthetic biomolecule. Examples of such a biomolecule include, but are not limited to, a protein, a polypeptide, an oligopeptide, a peptide, a polynucleotide, an oligonucleotide, a nucleotide, nucleic acid (e.g., including DNA, such as cDNA or genomic DNA, and RNA, such as mRNA), a polysaccharide, an oligosaccharide, lipid, a low weight molecule (e.g., a hormone, a ligand, a signal transduction substance, a low-weight organic molecule, etc.), and composite molecules thereof. Preferably, the biomolecule may be a nucleic acid or a protein, and more preferably DNA (e.g., cDNA or genomic DNA). In another preferred embodiment, the biomolecule may be DNA amplified by an amplification means, such as PCR or the like.

In another aspect, the present invention provides a biomolecule chip. This biomolecule chip comprises: 1) a substrate; and 2) biomolecules arranged on the substrate, wherein spots storing attribute data are arranged on a side of the substrate opposite to a side on which spots of the biomolecules are arranged. By arranging the spots storing attribute data on the rear side of the biomolecule chip, both data can be detected by a single read-out operation so that testing and/or diagnosis can be performed. Preferably, this attribute data may contain address information. The attribute data may contain biomolecule attribute data and the like.

In another aspect, the present invention provides a biomolecule chip comprising: 1) a substrate; 2) biomolecules arranged on the substrate; and 3) a data recording region. By providing such a data recording region, it is possible to perform testing and/or diagnosis using only a biomolecule chip. Preferably, the data recording region may be placed on a side of the substrate opposite to a side on which spots of the biomolecules are arranged.

In one aspect, the present invention provides a method for detecting a label of a biomolecule chip. This method comprises the steps of: 1) providing a biomolecule chip on which at least one labeled biomolecule is arranged; 2) switching detection elements sequentially for detecting the biomolecules on the biomolecule chip; and 3) identifying a signal detected by the detection element. With this method, a signal can be detected efficiently and in real time in a biomolecule chip. Preferably, this method further comprise: 4) adding up each detected signal. In one embodiment, this signal may be separated using a wavelength separation mirror. In another embodiment, the above-described biomolecule substrate may further comprise a synchronization mark, and the label may be identified based on the synchronization mark. By providing the synchronization mark, an address can be smoothly identified. In another embodiment, the biomolecule substrate contains address information on a rear side of the biomolecule, and the label is identified based on the address information.

In another aspect, the present invention provides a method for testing information from an organism. This method comprises the steps of: 1) providing a biomolecule sample from the organism; 2) providing a biomolecule chip of the present invention; 3) contacting the biomolecule sample to the biomolecule chip, and placing the biomolecule chip under conditions which causes an interaction between the biomolecule sample and a biomolecule placed on the biomolecule chip; and 4) detecting a signal caused by the biomolecule and a signal caused by the interaction, wherein the signal is an indicator for at least one information parameter of the organism, and the signal is related to an address assigned to the non-equal interval or the spot arrangement.

In a preferred embodiment of the method of the present invention for testing information on an organism, the sample contains a protein and the biomolecule placed on the biomolecule chip is an antibody, or the sample contains an antibody and the biomolecule placed on the biomolecule chip is a protein. In this detection method, hybridization between nucleic acids is detected. This hybridization may be performed under various stringency conditions. When SNP is detected, stringent hybridization conditions may be used. When a gene having a relationship but being far with respect to species is searched for, moderate hybridization conditions may be used. Such hybridization conditions can be determined by those skilled in the art from the well-known routine techniques, depending on the situation.

In a preferred embodiment of the method of the present invention for testing information on an organism, the sample contains a protein and the biomolecule placed on the biomolecule chip is an antibody, or the sample contains an antibody and the biomolecule placed on the biomolecule chip is a protein. In this detection method, an antigen-antibody reaction is detected. An antigen-antibody reaction may be detected under various stringency conditions. The antibody may be either a monoclonal antibody or polyclonal antibody. Preferably, the antibody may be a monoclonal antibody. The antibody may be a chimera antibody, a humanized antibody, or the like.

In a preferred embodiment, the method of the present invention further comprises labeling the biomolecule sample with a label molecule. By labeling a sample with a desired label molecule, a desired detection means can be used.

In a preferred embodiment of the method of the present invention for testing information on an organism, the label molecule may be distinguished from the biomolecule placed on the biomolecule chip. By providing a label which can be distinguished from a biomolecule, it is easy to detect a spot in which an interaction occurs. The label which can be distinguished from a biomolecule refers to a label which can be distinguished from a biomolecule by at least one detection means as described above.

In a preferred embodiment of the method of the present invention for testing information on an organism, the above-described label molecule contains a fluorescent molecule, a phosphorescent molecule, a chemoluminescent molecule, or a radioactive isotope. In this case, a detection means corresponding to the type of label molecule may be used.

In a preferred embodiment of the method of the present invention for testing information on an organism, the signal detecting step may be performed either at a site different from where the interaction occurs or at the same site as where the interaction occurs. When the signal detecting step is performed at a different site, the signal may be encrypted. Such encryption is well known in the art. For example, encryption using a public key may be used. By performing detection at a different site, it may be possible to outsource diagnosis or testing.

In a preferred embodiment of the method of the present invention for testing information on an organism, the method may further comprise subjecting the signal to filtering so as to extract only signals relating to required information. This step may be required for protecting personal information when outsourcing testing.

In another aspect, the present invention provides a method for diagnosing a subject. The method comprises the steps of: 1) providing a sample from the subject; 2) providing a biomolecule chip of the present invention; 3) contacting the biomolecule sample to the biomolecule chip, and placing the biomolecule chip under conditions which causes an interaction between the biomolecule sample and a biomolecule placed on the biomolecule chip; 4) detecting a signal caused by the biomolecule and a signal caused by the interaction, wherein the signal is at least one diagnostic indicator for the subject, and the signal is related to an address assigned to the non-equal interval or the spot arrangement; and 5) determining the diagnostic indicator from the signal.

In a preferred embodiment of the method of the present invention for testing information on an organism, the sample is nucleic acid, and the biomolecule placed on the biomolecule chip is nucleic acid. In this detection method, hybridization between nucleic acids is detected. This hybridization may be performed under various stringency conditions. When SNP is detected, stringent hybridization conditions may be used. By placing nucleic acid relating to a specific disease on a biomolecule chip, a signal caused by hybridization may be an indicator for the specific disease.

In a preferred embodiment of the method of the present invention for testing information on an organism, the sample contains a protein and the biomolecule placed on the biomolecule chip is an antibody, or the sample contains an antibody and the biomolecule placed on the biomolecule chip is a protein. In this test method, an antigen-antibody reaction is detected. The antigen-antibody reaction may be detected under various stringency conditions. By placing a protein or an antibody relating to a specific disease or condition on a biomolecule chip, a detected signal may be an indicator relating to the specific disease or condition.

In a preferred embodiment of the method of the present invention for testing information on an organism, the method further comprises labeling the sample with a label molecule. By labeling a sample with a desired label, a desired detection means can be used. The label molecule may be distinguishable from a biomolecule placed on the above-described biomolecule chip. By providing a label which can be distinguished from a biomolecule, it is easy to detect a spot having an interaction.

In a preferred embodiment of the method of the present invention for testing information on an organism, the above-described label molecule may contain a fluorescent molecule, a phosphorescent molecule, a chemoluminescent molecule, or a radioactive isotope. In this case, a detection means corresponding to the type of the label molecule may be used.

In a preferred embodiment of the method of the present invention for testing information on an organism, the diagnostic indicator may be an indicator for a disease or a disorder. In another embodiment, the diagnostic indicator may be based on single nucleotide polymorphism (SNP). This diagnostic indicator may be related to a genetic disease. In another embodiment, the diagnostic indicator may be based on the expression level of a protein. The diagnostic indicator may be based on a test result of a biochemical test. A plurality of test values based on the biochemical tests may be used.

In a preferred embodiment of the method of the present invention for testing information on an organism, the determining step may be performed either at a site different from where the interaction occurs or at the same site as where the interaction occurs. When the determining step is performed at a different site, the present invention may further comprise encrypting the signal. By performing detection at a different site, it may be possible to out source diagnosis or testing. Such out sourcing corresponds to industrially applicable work.

In a preferred embodiment of the method of the present invention for testing information on an organism, the method may further comprise subjecting the signal to filtering so as to extract only signals relating to required information. This step may be required for avoiding excessive leakage of personal information to protect the personal information when outsourcing testing.

In a preferred embodiment of the method of the present invention for testing information on an organism, in the detecting step biomolecule attribute data is hidden, and in the determining step personal information data is hidden. Thereby, the whole information required for diagnosis is prevented from being concentrated into a person or entity, whereby personal information can be protected.

In another aspect, the present invention provides a test apparatus information on an organism. This apparatus comprises: 1) a biomolecule chip of the present invention; 2) a sample applying section in fluid communication with the biomolecule chip; 3) a reaction control section for controlling a contact and an interaction between the biomolecule placed on the biomolecule chip and a biomolecule sample applied from the sample applying section; and 4) a detection section for detecting a signal caused by the interaction, wherein the signal is an indicator for at least one information parameter of the organism, and the signal is related to an address assigned to the non-equal interval or the spot arrangement. This apparatus can perform testing of biological information without additional address identification.

In a preferred embodiment, the test apparatus of the present invention further comprises a section for receiving and sending the signal. By providing the section for receiving and sending the signal, it is possible to send or receive information to or from the outside. This sending and receiving section may be connected to a recording apparatus drive, such as a flexible disk drive, an MO drive, a CD-R drive, a DVD-R drive, or a DVD-RAM drive; or a network, such as the Internet or an intranet.

In a preferred embodiment, the test apparatus of the present invention further comprises a region for recording the signal. By providing the recording region, it is possible to store a result of a test. When the test apparatus is used a plurality of times, stored test results can be compared with each other.

In another aspect, the present invention provides a diagnosis apparatus for a subject. The apparatus comprises: 1) a biomolecule chip of the present invention; 2) a sample applying section in fluid communication with the biomolecule chip; 3) a reaction control section for controlling a contact and an interaction between the biomolecule placed on the biomolecule chip and a biomolecule sample applied from the sample applying section; 4) a detection section for detecting a signal caused by the biomolecule and a signal caused by the interaction, wherein the signal is an indicator for at least one information parameter of the organism, and the signal is related to an address assigned to the non-equal interval or the spot arrangement; and 5) determining the diagnostic indicator from the signal. This apparatus can perform testing of subject information without additional address identification.

In a preferred embodiment, the test apparatus of the present invention further comprises a section for receiving and sending the signal. By providing the section for receiving and sending the signal, it is possible to send or receive information to or from the outside. This sending and receiving section may be connected to a recording apparatus drive, such as a flexible disk drive, an MO drive, a CD-R drive, a DVD-R drive, or a DVD-RAM drive; or a network, such as the Internet or an intranet.

In a preferred embodiment, the test apparatus of the present invention further comprises a region for recording the signal. By providing the recording region, it is possible to store a result of diagnosis. When the test apparatus is used a plurality of times, stored diagnosis results can be compared with each other.

In another aspect, the present invention provides a biological test system, comprising: A) a main sub-system, comprising: 1) a biomolecule chip of the present invention; 2) a sample applying section in fluid communication with the biomolecule chip; 3) a reaction control section for controlling a contact and an interaction between the biomolecule placed on the biomolecule chip and a biomolecule sample applied from the sample applying section; 4) a detection section for detecting a signal caused by the biomolecule and a signal caused by the interaction, wherein the signal is an indicator for at least one information parameter of the organism, and the signal is related to an address assigned to the non-equal interval or the spot arrangement; and 5) a sending and receiving section for sending and receiving a signal, and B) a sub sub-system, comprising: 1) a sending and receiving section for sending and receiving a signal; and 2) a test section for calculating a test value from the signal received from the main sub-system, wherein the main sub-system and the sub sub-system are connected together via a network.

Preferably, the main sub-system and the sub sub-system are connected together via a network.

In another preferred embodiment, the signal received by the sub sub-system contains a signal relating to measurement data measured by the sub sub-system.

More preferably, the attribute data contains chip ID, personal information data, and biomolecule attribute data; the main sub-system contains the chip ID and the personal information data, but does not contain the biomolecule attribute data; and the sub sub-system contains the chip ID and the biomolecule attribute data; but does not contain the personal information data, and the sub sub-system sends the test value, determined in response to a request, to the main sub-system. Therefore, the biological test system of the present invention prevents leakage of information to a third party. If information is leaked, privacy can be protected in testing an organism. In a preferred embodiment, the signal to be sent and received is encrypted.

Preferably, the above-described network may be the Internet or other networks (e.g., an intranet, etc.).

In another aspect, the present invention provides a diagnosis system comprising: A) a main sub-system, comprising: 1) the biomolecule chip of the present invention; 2) a sample applying section in fluid communication with the biomolecule chip; 3) a reaction control section for controlling a contact and an interaction between the biomolecule placed on the biomolecule chip and a biomolecule sample applied from the sample applying section; 4) a detection section for detecting a signal caused by the biomolecule and a signal caused by the interaction, wherein the signal is an indicator for at least one information parameter of the organism, and the signal is related to an address assigned to the non-equal interval or the spot arrangement; and 5) a sending and receiving section for sending and receiving a signal, and B) a sub sub-system, comprising: 1) a sending and receiving section for sending and receiving a signal; and 2) a determination section for determining the diagnostic indicator from the signal received from the main sub-system. The main sub-system and the sub sub-system are connected together via a network. In a preferred embodiment, the signal to be sent and received is encrypted.

Preferably, the signal received by the sub sub-system contains a signal relating to measurement data measured by the sub sub-system. More preferably, the attribute data contains chip ID, personal information data, and biomolecule attribute data, the main sub-system contains the chip ID and the personal information data, but does not contain the biomolecule attribute data, and the sub sub-system contains the chip ID and the biomolecule attribute data, and data for determining a diagnostic indicator from biomolecule attribute data, but does not contain the personal information data, and the sub sub-system sends the diagnostic indicator, determined in response to a request, to the main sub-system. Therefore, the diagnosis system of the present invention prevents leakage of information to a third party. If information is leaked, privacy can be protected in diagnosis.

Preferably, the above-described network may be the Internet or other networks (e.g., an intranet, etc.).

In another aspect, the present invention provides a test apparatus for biological information comprising: a substrate; a support for the substrate; a plurality of groups of biomolecules arranged on the substrate, each group containing the biomolecules of the same type; shifting means for shifting the substrate; a light source for exciting a fluorescence substance labeling a sample to be tested; and optical means for converging light from the light source. The light source is caused to emit light intermittently in response to an intermittent emission signal so as to excite the fluorescence substance, fluorescence from the fluorescence substance is detected by a photodetector during a period of time when the intermittent emission signal is paused, identification information is reproduced from an arrangement of the DNAs, and the biomolecules emitting fluorescence is identified.

Preferably, the test apparatus further comprises means for adding up detected detection signals. In another preferred embodiment, the test apparatus further comprises a wavelength separation mirror.

In another aspect, the present invention provides use of a biomolecule chip of the present invention for fabricating an apparatus for testing biological information.

In another aspect, the present invention provides use of a biomolecule chip of the present invention for fabricating an apparatus for diagnosing a subject.

In still another aspect, the present invention provides use of a biomolecule of the present invention for screening for a medicament and fabricating an apparatus for screening for a medicament. The present invention also provides a biomolecule chip for medicament screening. The present invention also provides a screening apparatus for medicament screening. The present invention also provides a method for screening for a medicament using a biomolecule chip of the present invention. These method, apparatus, and biomolecule chip have a fundamental structure constructed by the same principle as that of testing and diagnosis for a biomolecule, which can be implemented by those skilled in the art with reference to the present specification.

Hereinafter, the present invention will be described by way of examples illustrating best mode embodiments. Examples described be low are only for illustrative purposes. Therefore, the scope of the present invention is limited only by the scope of the claims, but not to the examples.

EXAMPLES

Hereinafter, best mode embodiments of the present invention will be described by way of examples with reference to FIGS. 1 to 46.

Example 1

Fabrication Example of Biomolecule Chip (1)

In this example, a method for arranging and immobilizing capture DNAs 2 having different sequences on a substrate 1 will be described.

FIG. 1(a) is a top view of DNA spots 2 in which a group of DNA fragments having a specific sequence are fixed on the substrate 1 in the shape of a dot according to the present invention. FIG. 1(b) is a cross-sectional view thereof. The substrate 1 is usually made of glass and may be made of a plastic. The shape of the substrate 1 may be a square like a DNA chip, or a circle. DNA dots 2 each contain a different capture DNA which is immobilized on the substrate 1. The size of the DNA dot is 100 to 200 µm in diameter in the case of a microarray, and 10 to 30 µm in the case of a DNA chip.

Figure 2:
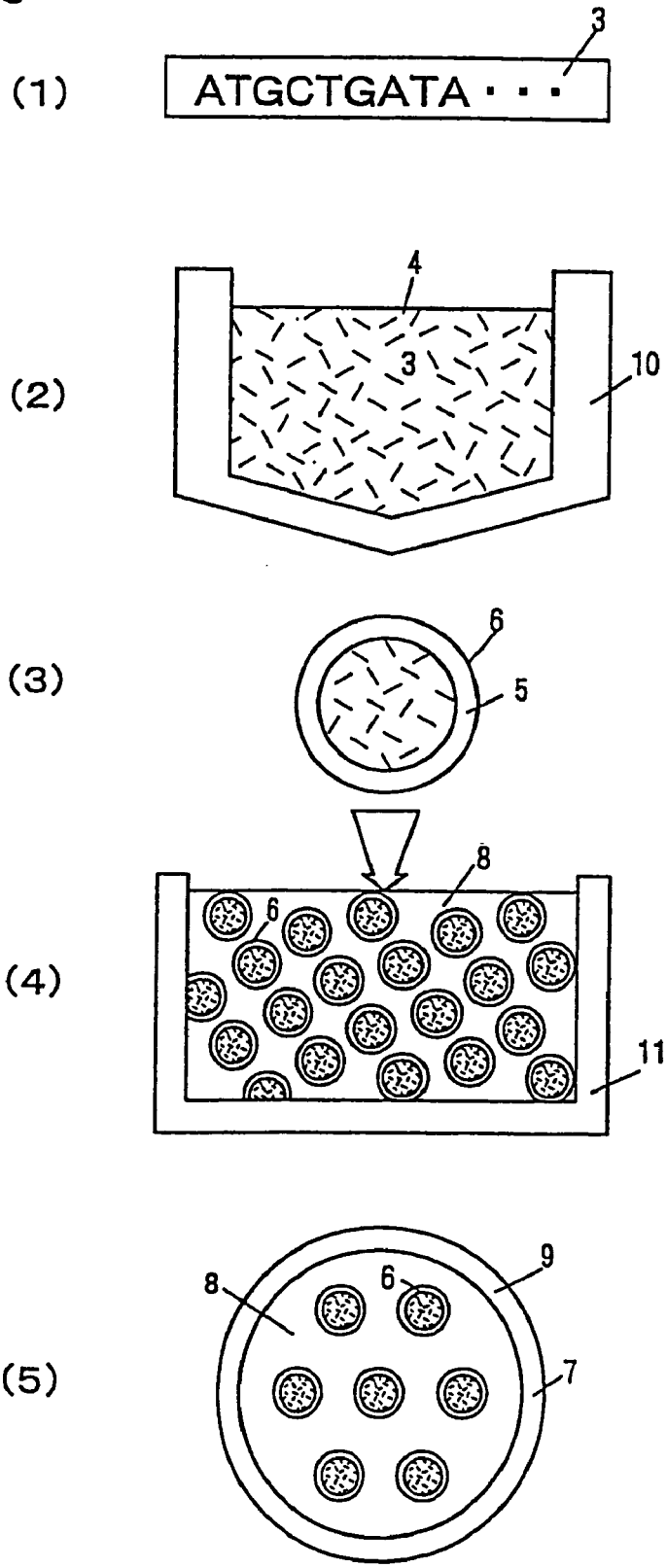

A method for forming DNA spots will be described with reference to FIGS. 2 and 3. As shown in FIG. 2, (1) shows a capture DNA 3. A method of preparing capture DNA is omitted. The capture DNA and labeled DNA with a subject label are subjected to hybridization so as to predict the sequence of subject DNA. (2) shows a DNA solution 4 containing the capture DNA 3. (3) shows a DNA microcapsule 6 in which the DNA solution Discovered with a covering 5. (4) shows a container 11 in which the DNA microcapsule 6 is dispersed in a solution 8. (5) shows a microcapsule 9 in which the DNA microcapsules 6 shown in (4) are collected and enveloped together with the solution 8 with a sub-membrane.

This microcapsulation makes it possible to select separately two solutions, i.e., the main solution 4 of DNA and the sub-solution 8 of the DNA microcapsule. As the DNA solution 4, a solution optimal to DNA or a solution required to immobilize the DNA 3 to the substrate 1 can be selected. As the sub-solution 8, a solution having an optimal viscosity or washing attachability when DNA is arranged on the substrate 1 in a PIN method or an ink jet method can be selected.

Figure 3:
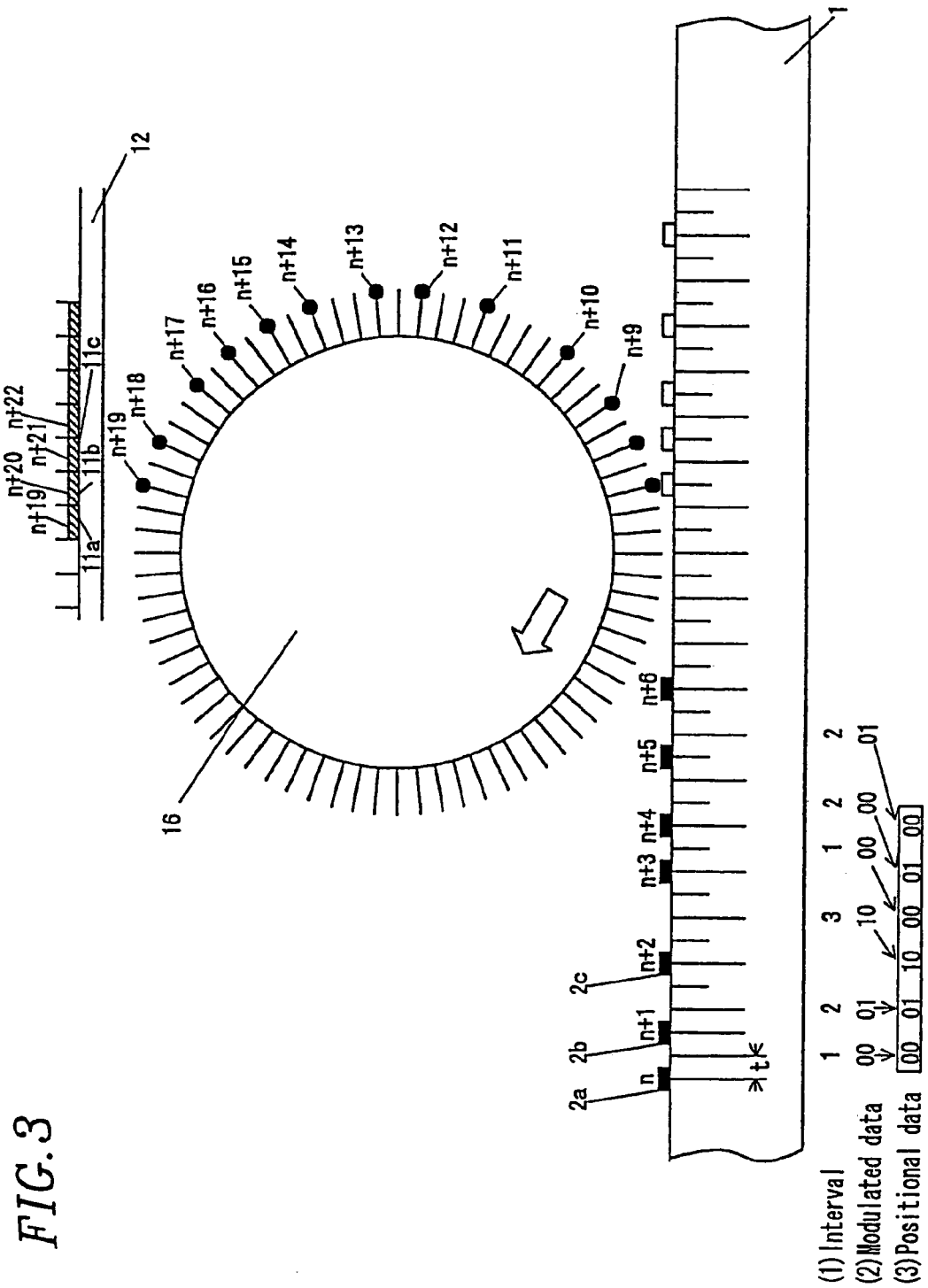
Figure 4:
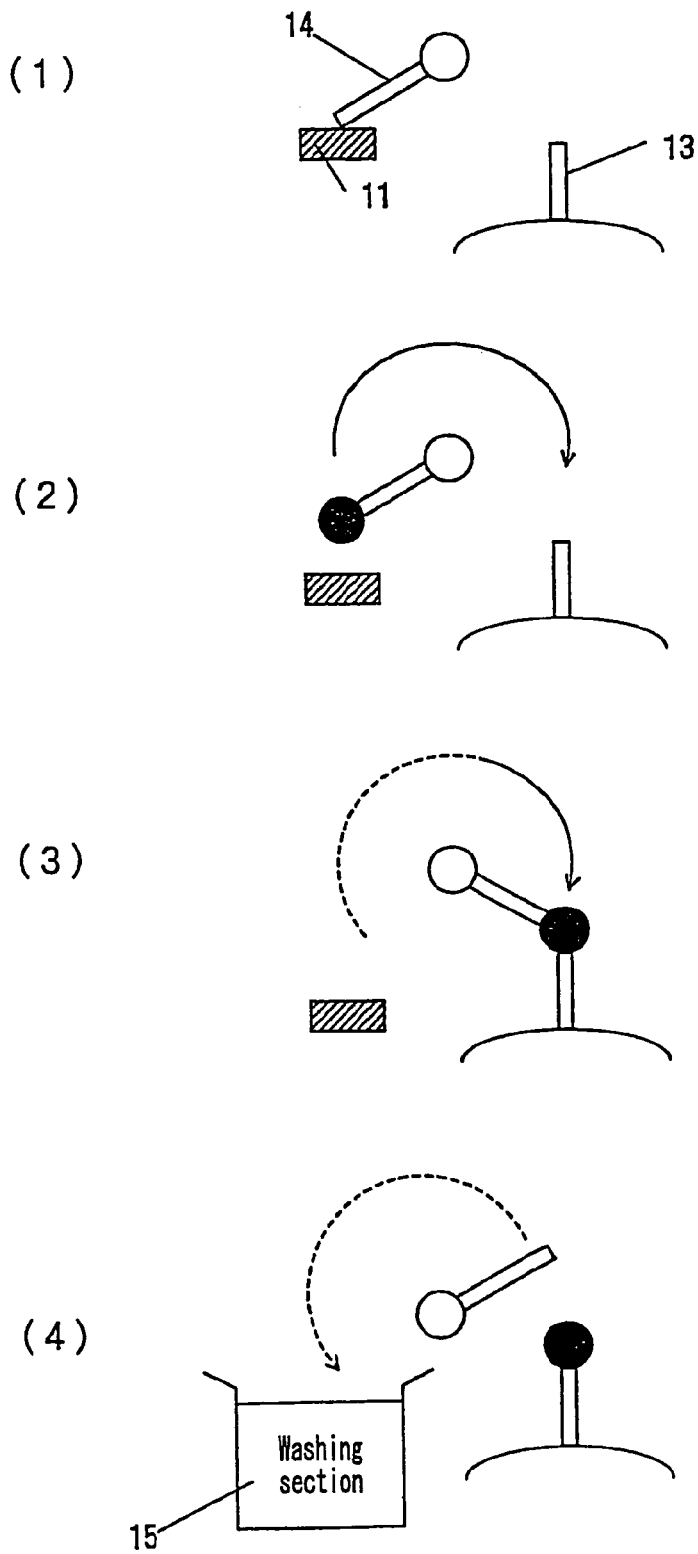

FIG. 3 shows a method for arranging $1^{st}$ to $K^{th}$ DNA spots on the substrate 1 by a pinning spot method. Initially, on a tray 12, several hundreds to several thousands of containers 11 (FIG. 2(4)) containing capture DNA having a different sequence are arranged in the order of DNA numbers. As shown in FIGS. 4(1), (2), (3) and (4), at (1) a moving pin 14 is moved so that the DNA microcapsule can be attached to the moving pin 14 from the DNA container 11; at (2) and (3) the DNA microcapsule solution is attached to a tip of a pin 13; at (4) the moving pin 14 is washed in a washing section 15, $n^{th}$ DNA is removed, and thereafter, $(n+1)^{th}$ DNA is attached to the moving pin 14. Returning to FIG. 3, $1^{st}$ to $K^{th}$ DNAs are attached one after another to the pins 13 on a pin drum 16, being spaced at specific intervals.

The attached DNAs are then attached to the substrate 1 one after another as the pin drum 16 is rotated. The DNAs 3 are thus placed on the substrate 1. Assuming that a half of the minimum DNA interval is defined as t, FIG. 3 illustrates that DNAs are spaced by intervals 1t, 2t, 3t, and 5t.

Figure 8:
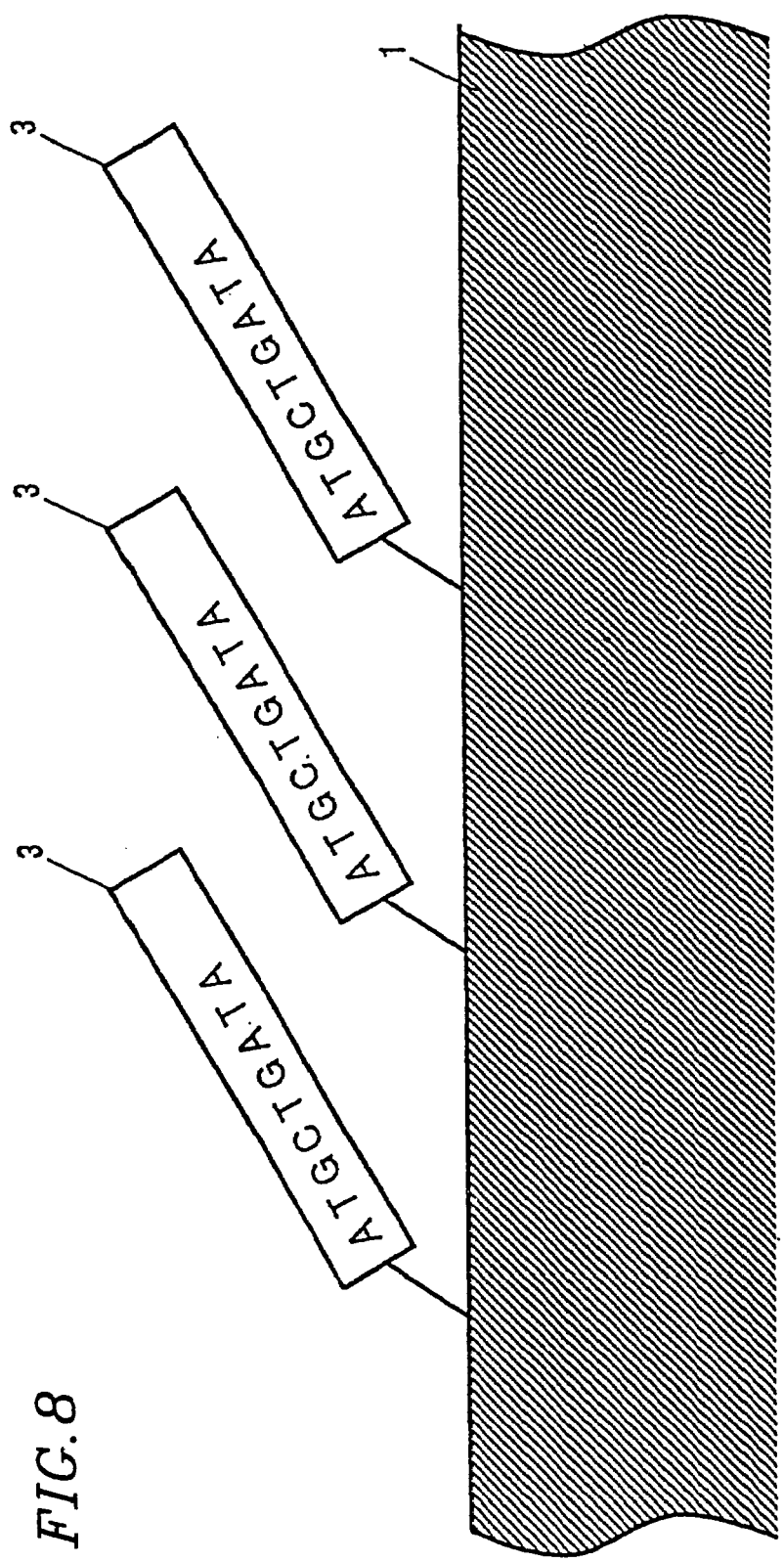

Immobilization of DNA in the attached DNA microcapsule 6 and the sub-solution 8, i.e., immobilization of capture DNA onto the substrate 1, will be described with reference to FIG. 7. As shown in FIG. 7(1), the DNA microcapsule 6 and the sub-solution 4 are attached onto the substrate 1. The vaporization temperature of sub-solution 4 is lower than the melting point of a membrane 6. Therefore, when the temperature is slightly increased at (2), the sub-solution 4 is evaporated, leaving only the microcapsule 6. When the temperature is further increased at (3) to the melting point of the membrane 6, the membrane 6 is melted so that the fluid of the melted membrane 6, the main solution 4, and the capture DNA 3 are mixed to a solution. In this case, the membrane 6 may be made of a material whose vaporization temperature is lower than the vaporization temperature of the main solution and the membrane 6 may be evaporated. A surface of the substrate 1 has been subjected to surface treatment so that DNA is easily immobilized on the surface. Therefore, at (4) the capture DNA 3 is immobilized on the substrate 1 as shown in FIG. 8. A part or the whole of the main solution 4 is dried at (5) and washed at (6), thereby completing the DNA spot 2.

In the present invention, arrangement of DNA spots 2a, 2b, and 2c is modulated so as to incorporate positional information thereinto. According to this positional information, the positional orders of the respective DNA spots 2 can be determined. At the same time, as shown in FIG. 5, a DNA spot region 17 and a data region 18 are separated from each other. In the data region, a substrate ID 19, a DNA number correspondence table 20 for the position of a DNA spot and a DNA spot ID, and the sequence data 21 of DNA itself (biomolecule attribute data) (data structure shown in FIG. 5(2)) are modulated and recorded in a dot pattern. The dot pattern can be read by an XY scanner. Therefore, the arrangement data of DNA spots can be read by an XY scanner. Alternatively, data in the data region can be read out using an excitation laser for allowing a sample to generate fluorescence. FIG. 6 shows a specific example of DNA substrate attribute data. DNA substrate ID 19, a DNA number-position correspondence table 20 indicating the correspondence between DNA numbers and positional information, and DNA sequence data 21 indicating the DNA sequence of each DNA, has been recorded as data in the data region before shipment from the factory. Note that the DNA sequence data of a DNA number is encrypted using an encryption key and then recorded. Personal DNA data is information of a high level of personal privacy which has to be stringently protected, and therefore, is encrypted using a public key, such as RSA, ellipse code, or the like, or a high-bit encryption key. Therefore, even if a DNA chip or a DNA substrate containing subject information is run off, the DNA sequence of a specific DNA spot cannot be read without an encryption key. Therefore, personal DNA information can be prevented from leaking. It is also conceivable to accumulate DNA sequence data 21 in a DNA management center without recording the data in DNA chips in order to improve security. The user informs a DNA management center of a DNA substrate ID 19 and a reaction between labeled DNA 22 and a DNA spot 2, i.e., fluorescence level data. Next, the center searches a DNA substrate database for the DNA sequence of each DNA spot using the. DNA substrate ID 19. The center further analyzes a reaction result of a DNA spot and labeled DNA 22, DNA sequence-disease correspondence data to diagnose and predict a disease (in the case of a human), and sends only necessary information to laboratory medical technologist or a doctor in encrypted form. With this system, privacy information is prevented from improperly leaking.

Example 2

Fabrication Example of Biomolecule Chip (2): Ink Jet Method

Figure 9:
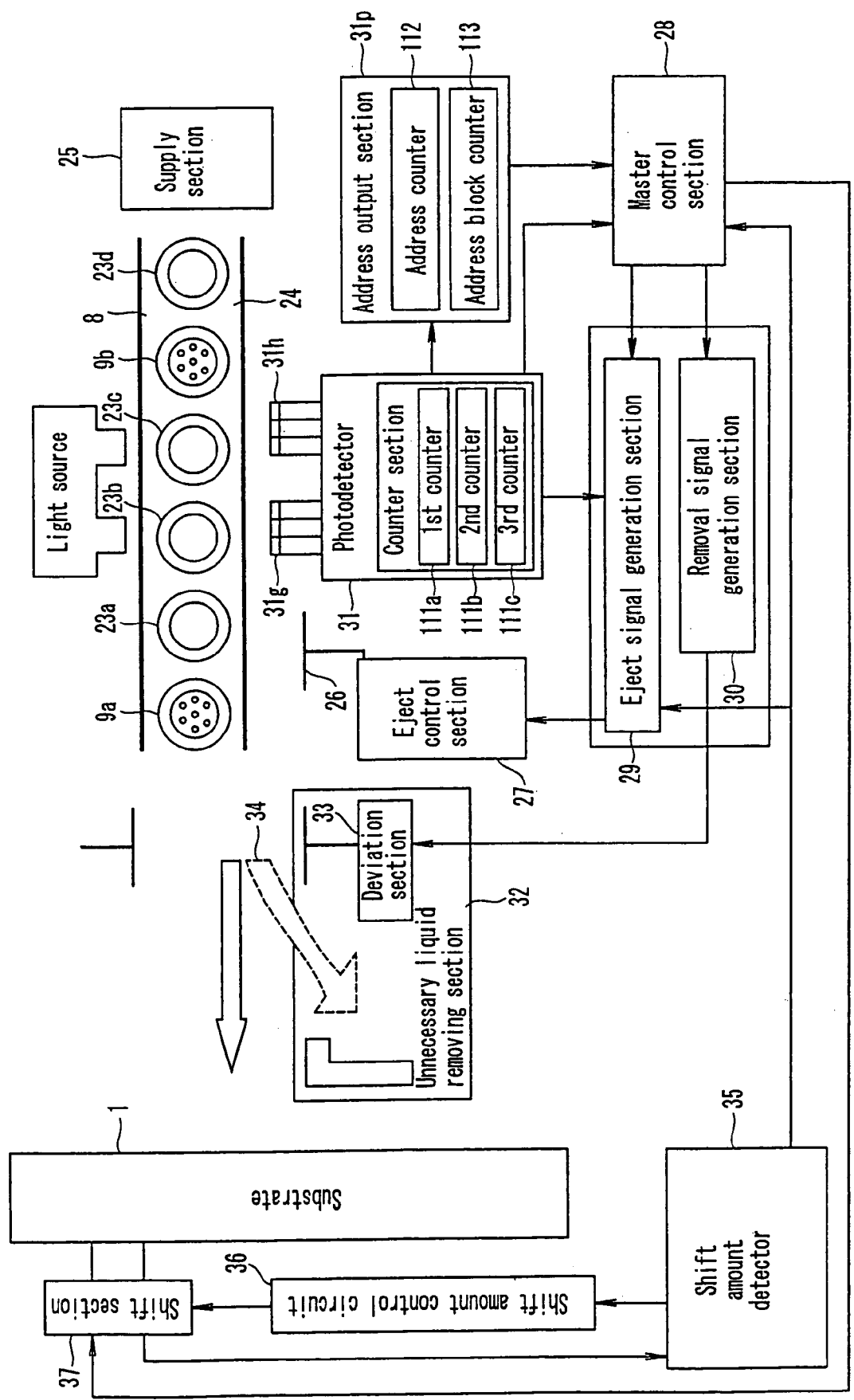

The pin spot method has been described above. Next, a method of attaching DNA to a substrate using ink jet will be described. FIG. 9 is a block diagram showing an inkjet (Bubble Jet®) attaching apparatus. An ink jet nozzle 24 contains microcapsules 9a, 9b containing DNA and empty microcapsules 23a, 23b, 23c, 23d containing only main solution 4, which are supplied from an ink supplying section 25. A specific empty capsule contains a specific dye for indicating address information. A master control section 28 sends an eject command to an eject signal generation section 29 and then an eject control circuit 27. As a result, an eject section 26 generates heat so that bubbles occur. The bubbles cause the microcapsule 9a to be ejected toward a substrate. The empty microcapsules 23b, 23c are ejected. However, the empty microcapsules 23b, 23c are unnecessary. When a photodetector 31 detects an empty microcapsule, a removal signal generation section 30 sends a removal signal to an unnecessary liquid removing section 32. In the unnecessary liquid removing section 32, a deviation field is applied to a deviation section 33 so that unnecessary liquid in the empty microcapsule 23 is removed as indicated by dashed-line arrow 34 and does not reach a substrate.

The photodetector 31 has color filters 31g, 31h, 31i (R, G, B, etc.), and therefore, can detect the color information of an empty microcapsule. The photodetector 31 also has a counter section 111. A first counter 111a counts the number of microcapsule blocks. A second counter 111b counts the number of DNA microcapsules. A third counter 111c counts the number of empty microcapsules. When there are four colors, 2-bit address data is obtained from a set of empty microcapsules. 16-bit address data is obtained from 8 empty microcapsules. When two bits out of the 16 bits are used as check bits, it is possible to precisely check if the order, arrangement, or number of microcapsules is incorrect. Therefore, incorrect attachment can be advantageously prevented. Even when microcapsules are not colored, 2 bits can be obtained by ejecting 1, 2, 3, or 4 microcapsules consecutively. When 8 sets are used, 16 bits can be obtained, i.e., the same size of address data as above can be obtained. The address information of a microcapsule obtained by the photodetector 31 is sent via an address output section 31p to the master control section. DNA number can be identified based on address information. For example, as shown in step 68m in a flowchart of FIG. 15, if a microcapsule makes the number of DNA capsules having DNA number n greater by one, a removal section described below removes the microcapsule.

Figure 10:
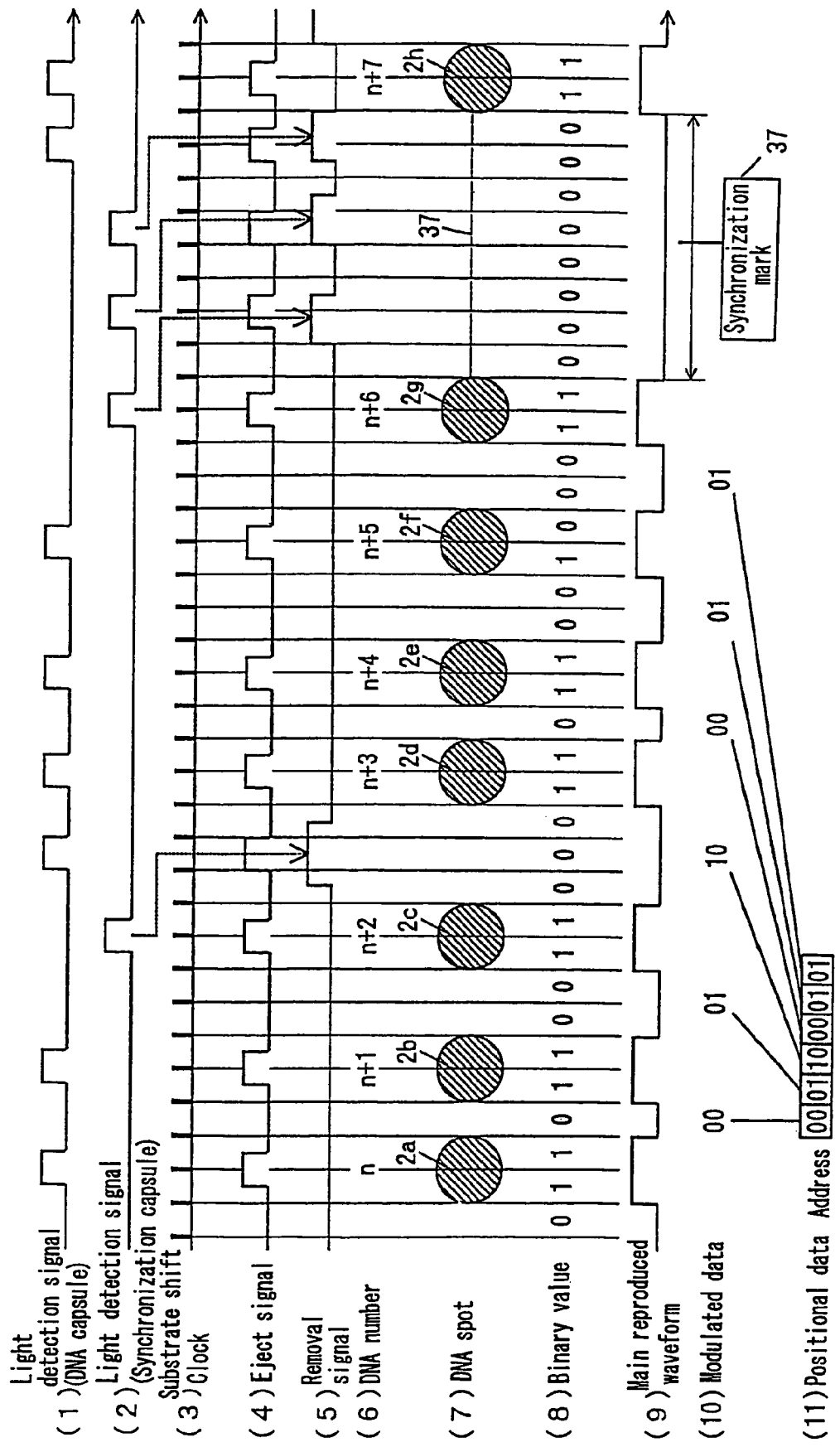

On the other hand, the substrate 1 is moved by a predetermined amount by a shift section 37 controlled by a shift amount control circuit 36 based on a signal from a shift amount detector 35, so that DNA spots 2a to 2h are attached onto the substrate 1 as shown in FIG. 10(4).

Figure 15:
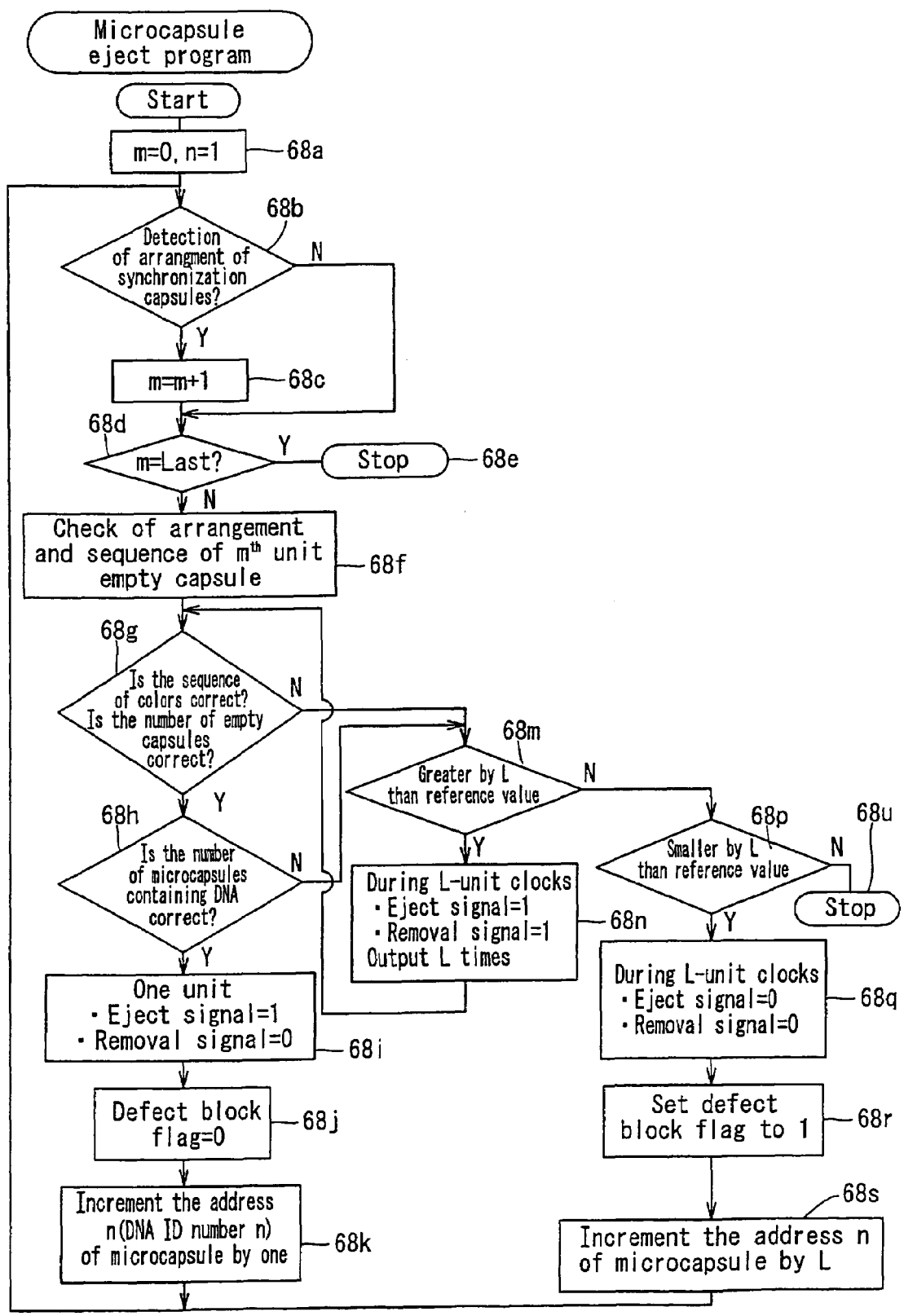

Next, the flowchart of FIG. 15 will be described. Initially, step 68a sets m=0, n=1. If a synchronization capsule sequence is detected at step 68b, a capsule block number m of the first counter 111a is increased by one in step 68c. Whether or not m is the last number is checked in step 68d. The arrangement and order of empty microcapsules in $m^{th}$ block are checked in step 68f. If a result of step 68g is incorrect, the process goes to step 68m. If the number of microcapsules is greater by L than a reference number, an eject signal (=1) is output in step 68n for L capsules. A removal signal (=1) is output so as to remove a capsule. This operation is carried out L times to cause the arrangement to be normal and the process then returns to step 68g. If a result of step 68m is NO, the process goes to step 68p. If the number of microcapsules is smaller by L than the reference value, ejection is stopped for clocks corresponding to L microcapsules in step 68q. During this time, DNA spot 2 is missing. Therefore, a defect block flag is set to be 1, which is recorded in the data region 18 on the DNA substrate 2, indicating the presence of the defect. The address of a microcapsule in an address counter 112 or an address block counter 113 is corrected by increasing the address by L.

Now, the process returns to step 68g. The number of DNA microcapsules is checked in step 68h. If the result is OK, the eject signal is set to be ON and the removal signal is set to be OFF for one unit in step 68i. In this case, microcapsules are ejected so that one DNA spot is formed. In this case, it is judged that there is no defect, and the address for a DNA microcapsule is increased by one (step 68k). The process then returns to step 68b. Thus, DNA spots 2, which contain corresponding DNA, can be formed.

Now, an ejection procedure using ink jet will be described with reference to FIG. 11. In (1), (2), the microcapsule 9a containing $n^{th}$ DNA reaches the tip of the nozzle 24. When a voltage is applied to the eject section 26 in (2), a bubble is generated so that the microcapsule 9a is ejected in (3) and is attached to the substrate 1 in (4). This method is called Bubble Jet®. A piezoelectric device may be provided instead of the eject section 26 to obtain the same effect. In this case, by applying an eject voltage to the piezoelectric device, a microcapsule is ejected in a piezoelectric ink jet method. Meanwhile, the microcapsule 9b containing $(n+1)^{th}$ DNA reaches the tip portion. When an eject voltage is applied in (5), the microcapsule 9b is ejected toward the substrate 1. In (6), $(n+2)^{th}$ microcapsule 9c is transported to the tip portion. In this case, the empty microcapsules 23d, 23e among the three consecutive empty microcapsules 23c, 23d, 23e indicating a synchronization mark are present on the photo detectors 31a, 31b. These empty microcapsules have a high level of transmittance, both of which are detected by the photodetector 31. The capsules are detected as synchronization marks. Therefore, the microcapsule 9d following these capsules is recognized as containing $(n+3)^{th}$ DNA from a correspondence table. Therefore, it is possible to prevent ejection of DNA having an erroneous number due to displacement of a microcapsule. A synchronization mark is composed of 2, 3, or 4 empty capsules. One set can contain 2-bit data. A synchronization capsule is used to match DNA itself to its DNA number, so that the matched DNA can be ejected. If DNA having a specific number is not ejected as in step 68p of FIG. 15, lack information is recorded in the data region of FIG. 5. As shown in FIG. 12, for example, a plurality of $(n+1)^{th}$ DNA spots are formed as DNA spots 3a, 3b, 3c. Therefore, a lack of DNA spot does not cause a problem. In (7), the synchronization capsules 23d, 23e reach the tip portion. These capsules do not contain DNA and are unnecessary. Therefore, a removal signal is applied in (8), the capsules are deviated and removed by the unnecessary liquid removing section 32 so that the capsules do not reach the substrate 1. The removal circuit can prevent unnecessary substances from being attached to the substrate 1.

A light detection signal, an eject signal, a removal signal and an arrangement of DNA spots will be described with reference to FIG. 10. Initially, a system is operated in accordance with a shift clock in FIG. 10(3). Initially, since a DNA capsule has a low level of light transmittance as shown in FIG. (1), the DNA capsule is detected in synchronization with an eject signal in (4). Synchronization capsules are detected as shown in (2) since the two photodetectors 31a, 31b are both turned ON. As shown in (4), an eject signal is generated both for a microcapsule containing DNA and a synchronization capsule containing no DNA. However, a removal signal of (5) is generated in synchronization with an eject signal following a detection signal of (2) so that all synchronization capsules are removed. In the present invention, in order to specify the DNA number of each DNA spot 2, positional data, such as address or the like, is buried as the intervals between DNA spots as shown in (11). When positional data is 12 bits in length, the positional data is divided into 00, 01, 10, 00, and 01 as shown in (10), where 00 corresponds to a mark interval of 3 clocks and 01, 10 and 11 corresponds to 4t, 5t and 6t, respectively. Thus, interval modulation is performed. Further, there is a synchronization mark 37 having an interval of 10t. With this method, positional information can be buried when DNA spots are formed. Since the address of each DNA spot is obtained, the DNA number of a first DNA spot for a synchronization mark is obtained from DNA number positional information 20 shown in FIG. 6. In the present invention, therefore, the DNA numbers of all DNA spots 2 can be identified. The sequence information of all DNA spots can be obtained by using sequence information 21 for DNA numbers recorded in the substrate 1 of FIG. 6. Since the address is obtained, absolute precision is not required when the position of a DNA spot is read out. Therefore, a high-precision XY scanner is not required and it is possible to prepare and read a DNA spot with a low-precision apparatus, thereby making it possible to supply an inexpensive DNA testing apparatus. In the prior art, ultrahigh-precision fabrication and readout apparatuses are required in order to increase the density of DNA spots. In the present invention, high density can be achieved by a low-precision fabrication and readout apparatuses. Further, since the attribute data of DNA spots are recorded on the same substrate 1 as shown in FIG. 6, the possibility of incorrectly reading out a DNA attribute is advantageously eliminated.

Figure 30:
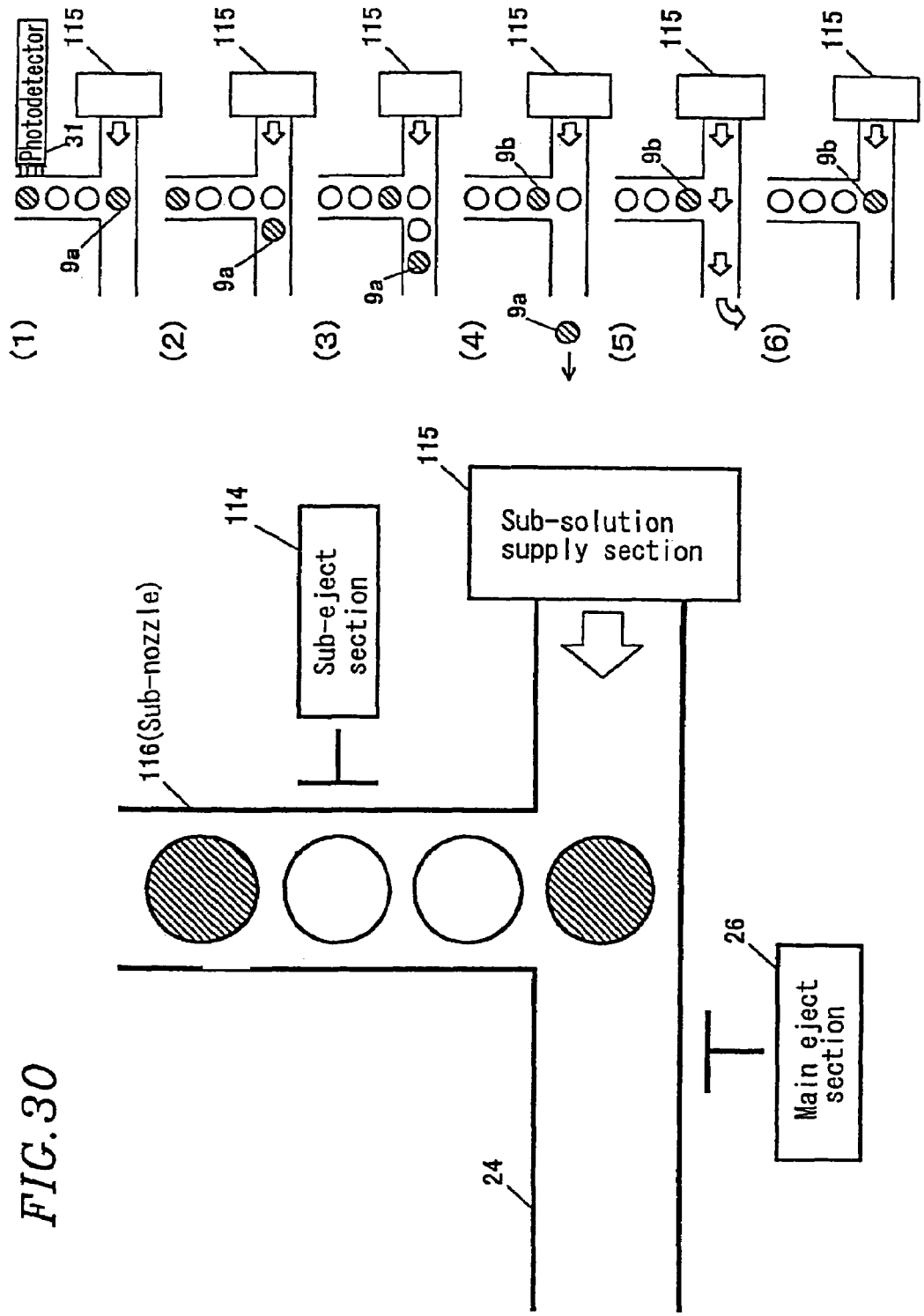

FIG. 30 shows a sub-nozzle 116, a sub-eject section 114, and a sub-solution supply section 115 in addition to the system of FIG. 9. The sub-nozzle 116 is supplied with microcapsules, and a sub-solution from the sub-solution supply section 115.

Operations will be described from (1) to (6) in sequence. In (1), (2) and (3), a DNA capsule 9a is transported, and in (4), is ejected. In (5), a large volume of sub-solution is released from the sub-solution supply section 115 and then removed by the removal section 32. In (6), a DNA microcapsule 9b is transported. In this method, the inside of the nozzle is washed with the sub-solution, whereby the mixing of DNA can be prevented.

Bead Method

Figure 49:
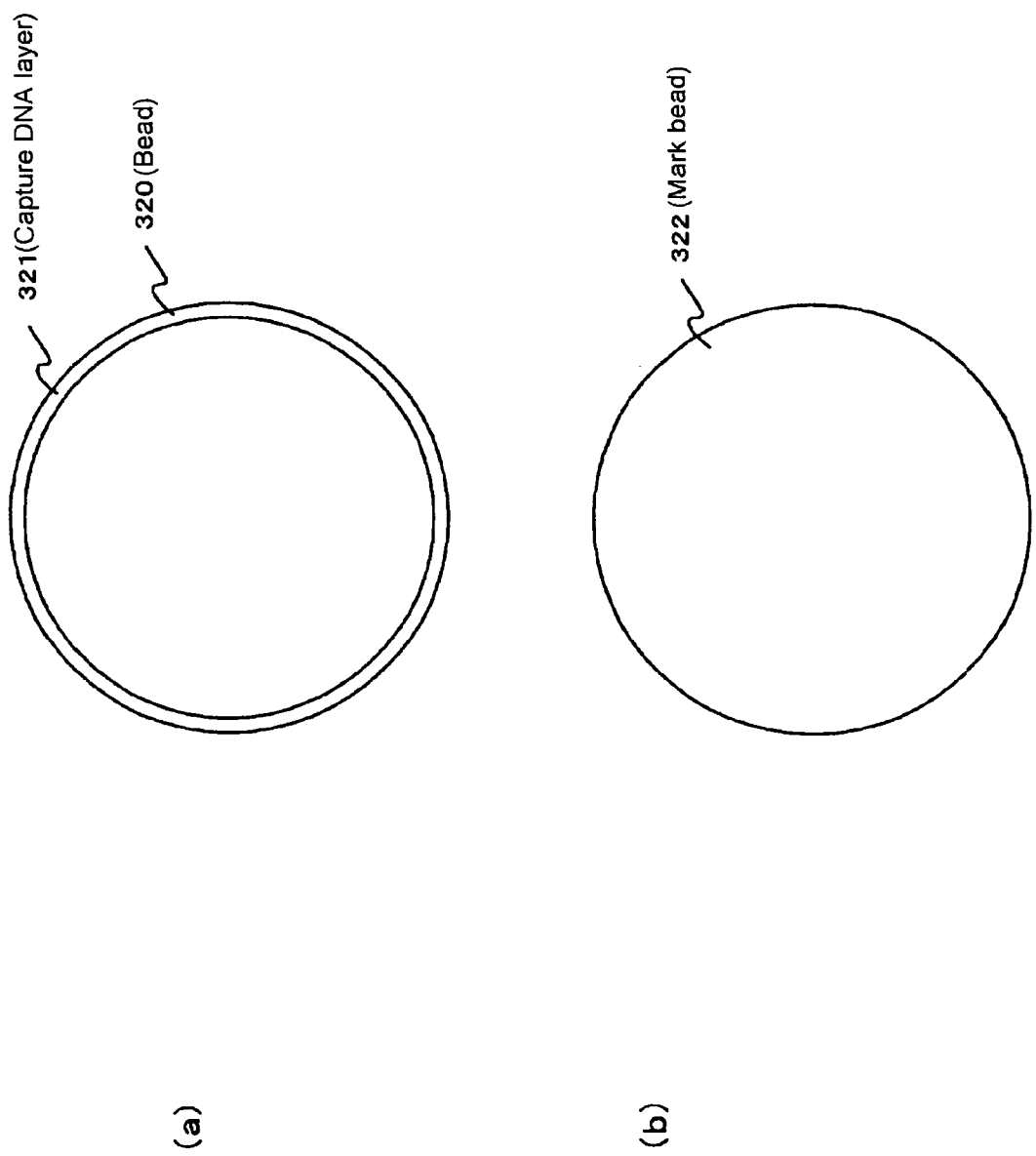

Hereinafter, a bead method, which is derived from the Ink Jet Method, is described. FIG. 49(a) is a cross-sectional view of a DNA bead 320 which consists of a light-transmissive spherical bead made of glass or plastics and having a diameter from several tens to several hundreds of micrometers in a core; and a DNA layer 321 surrounding the spherical bead in which probe DNA or capture DNA is immobilized. FIG. 49(b) is a cross-sectional view of a mark bead 322 for marking, which consists of a spherical bead made of glass or plastics absorbing a light of a specific wavelength.

Figure 50:
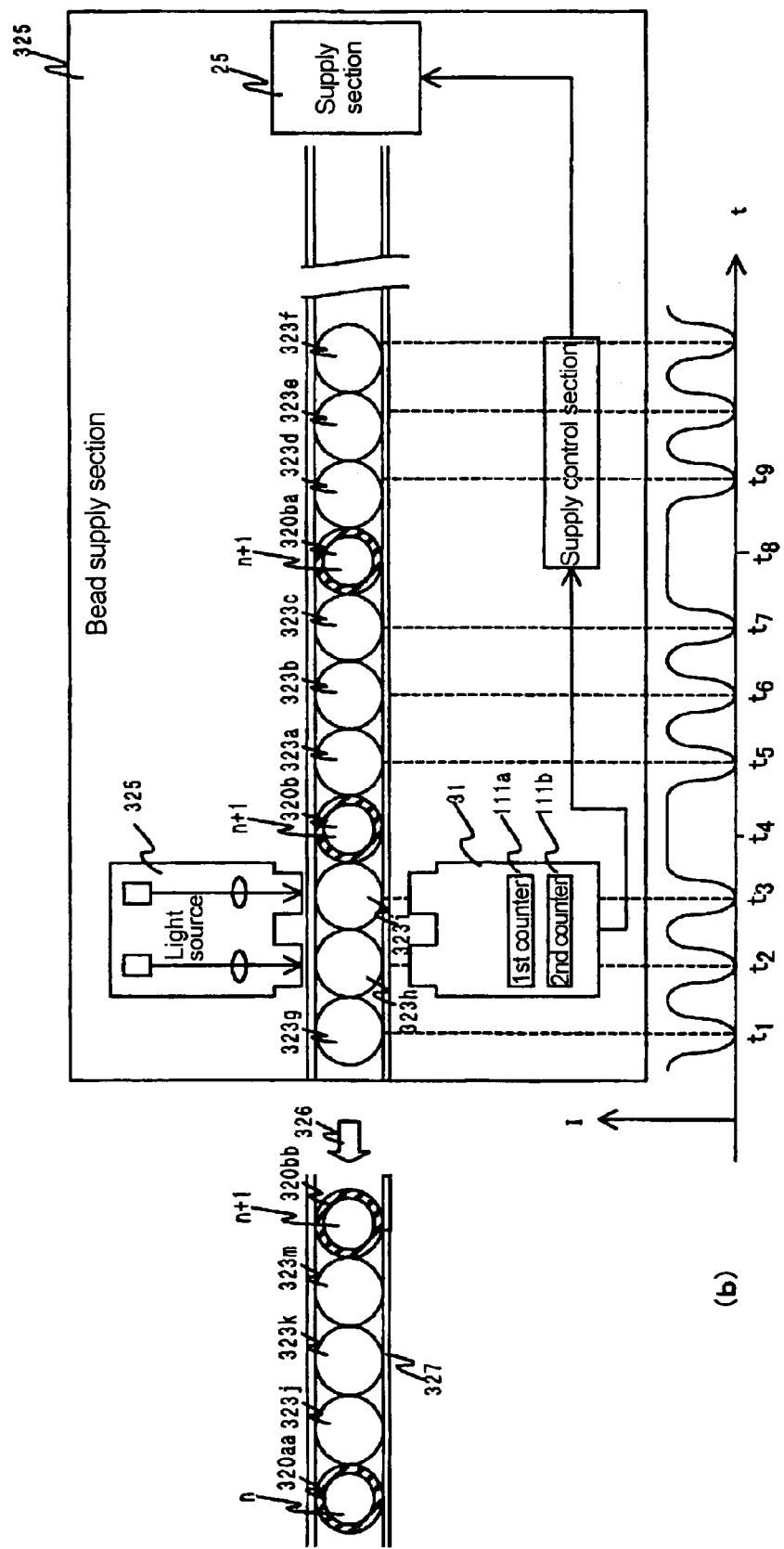

FIG. 50(a) is a diagram showing a principle of a $(n+1)^{th}$ bead supplying section which supplies a $(n+1)^{th}$ bead at a $(n+1)^{th}$ step. The description of an ejection operation of the bead 320 is omitted because of substantially the same operation as in FIG. 9.

A DNA bead 320b having a $(n+1)^{th}$ capture DNA, space beads 323a, 323b and 323c absorbing a light of a specific wavelength, a DNA bead 320ba, and space beads 323d, 323e and 323f are ejected from the bead supplying section 25 in sequence. As shown in a graph in FIG. 50(b) which indicates a light intensity I, a partially attenuated signal is detected by a photodetector 31 due to light attenuation caused when the light from the light source 325 passes through the space beads 323. Thereby, a number of space beads 323 passing by in front of the photodetector 31 may be counted by a first counter 111a. The existence of DNA beads 320 can be detected because the DNA beads 320 do not attenuate the transmitted light and a light intensity is not attenuated at $t=t_4$ and $t=t_8$ in the light intensity signal in FIG. 50(b). Thereby, a number of the DNA beads 320 passing by may be counted by a second counter 111b.

Beads proceeds towards the direction indicated by an arrow 326 by ejecting the beads, one $(n+1)^{th}$ DNA bead 320bb and a plurality of space beads 323m are conveyed into a glass tube 327 to form a DNA array. In the previous $n^{th}$ step, one DNA bead 320a having a $n^{th}$ capture DNA sequence has been already conveyed into the glass tube 327 by a bead supplying section 335a. Therefore, the DNA bead 320a already exists in the left section of the glass tube 327.

After the $(n+1)^{th}$ DNA bead 320bb has been supplied in the $(n+1)^{th}$ step, a DNA bead 320 having a $(n+2)^{th}$ capture DNA supplied by the $(n+2)^{th}$ bead supplying section 335b supplying a $(n+2)^{th}$ DNA bead in the $(n+2)^{th}$ step, is conveyed into the glass tube 327 by another supplying section. Upon repeating the above steps, several hundred types of DNA beads 320 may be conveyed into the glass tube 327.

Figure 51:
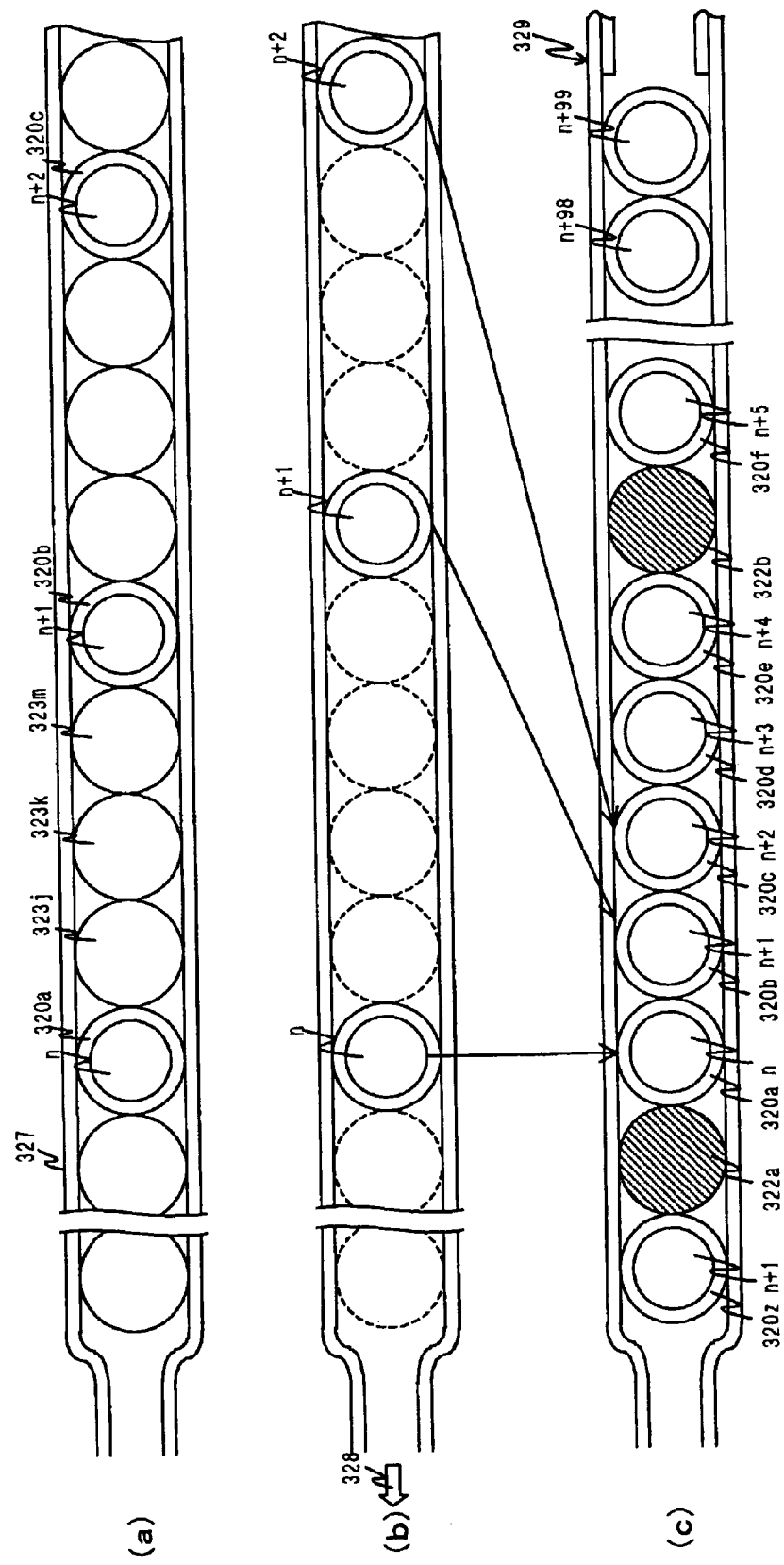
Figure 52:
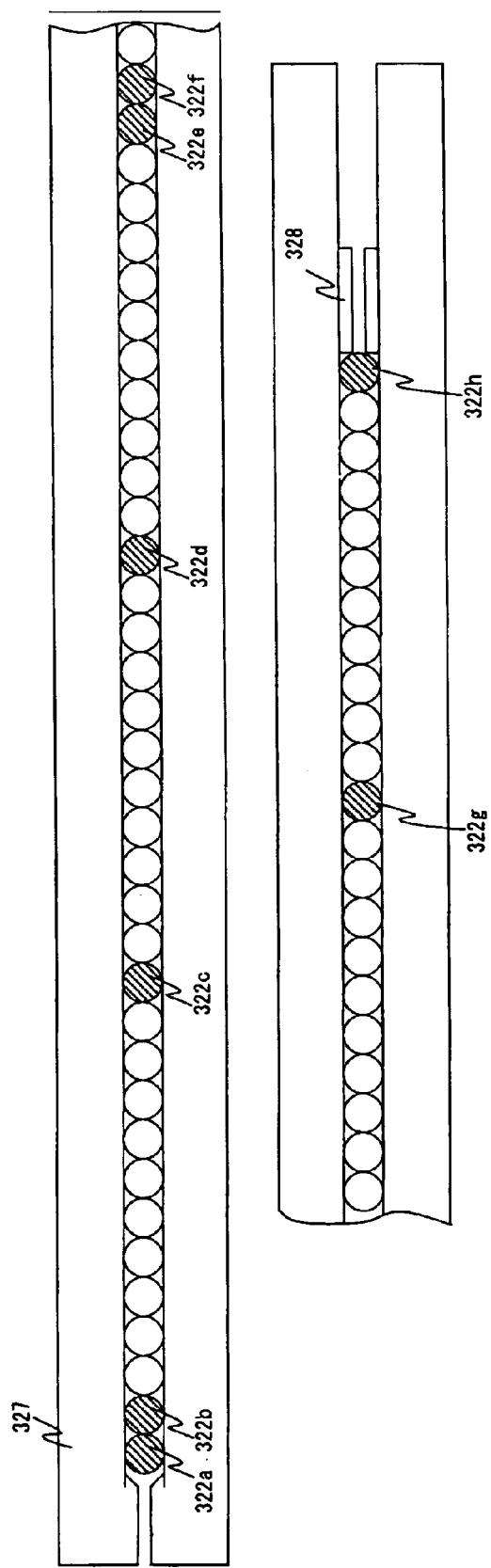

Thus, as shown in FIG. 51(a), the $n^{th}$ DNA bead 320a, the $(n+1)^{th}$ DNA bead 320b and the $(n+2)^{th}$ DNA bead 320c are arranged in sequence in the glass tube 327, and those DNA beads 320 are spaced by space beads 323. Finally, several hundred types of DNA beads may be arranged. Next, a step for melting space beads is performed. Temperature of the whole glass tube 327 is increased to or higher than $T_0$. By setting the $T_0$ to a temperature, for example, 10° C. higher than the melting point of the material of space beads 323, space beads 323 melt and flow out towards the direction indicated by an arrow 328 and, then, space beads disappear from the glass tube 327. Thus, as shown in FIG. 51(c), DNA beads 320z, 320a, 320b, 320c, 320d, 320e, 320f are arranged in the vicinity each other. Actually, mark beads 322a, 322b absorbing a light having a specific wavelength are arranged in predetermined intervals in order to identify addresses. Thus, a bead type DNA array 329 is completed. FIG. 52 is a schematic illustration showing a normalized DNA array 329 in whole. In the tip of this DNA array 329, two mark beads 322a, 322b for identifying addresses are adjacently arranged. Next to them, 10 consecutive DNA beads 320, one mark bead 322c, and one mark bead 322d are arranged and, then, two mark beads 322e, 322f are adjacently arranged. When the address for the two adjacent mark beads is defined as "11", addresses can be identified by mark beads. Therefore, more DNA beads are arranged, addresses can be identified more precisely, resulting in reduction of miss detections. Subsequently, one mark bead 322g and one mark bead 322h are arranged separately. At the end of the array, there is a cap 328 to prevent the DNA beads 320 from flowing out.

It is very difficult to insert minute beads having a diameter from several tens μm to several hundreds μm and having different DNA sequences one by one into a glass tube. In the present method described in FIGS. 50 and 51, a set of one DNA bead and a plurality of space beads in front and in rear of the DNA beads are treated as one group. Since beads are conveyed in one group, and a number of beads in the group is counted by checking its tail, absolutely one DNA bead can be ejected. Even when a number of space beads to be ejected fluctuates by one or two, only one DNA beads is ejected because the number of the DNA beads is controlled. Even when space beads in front and in rear of the DNA beads in one group are ejected one or two more or less than prescribed, since these space beads will be disappeared in the following heating step. Thus, the arrangement of the DNA array is entirely unaffected. Consequently, this method has an effect to eject a prescribed number (e.g., one) of DNA bead(s) can be ejected.

Figure 53:
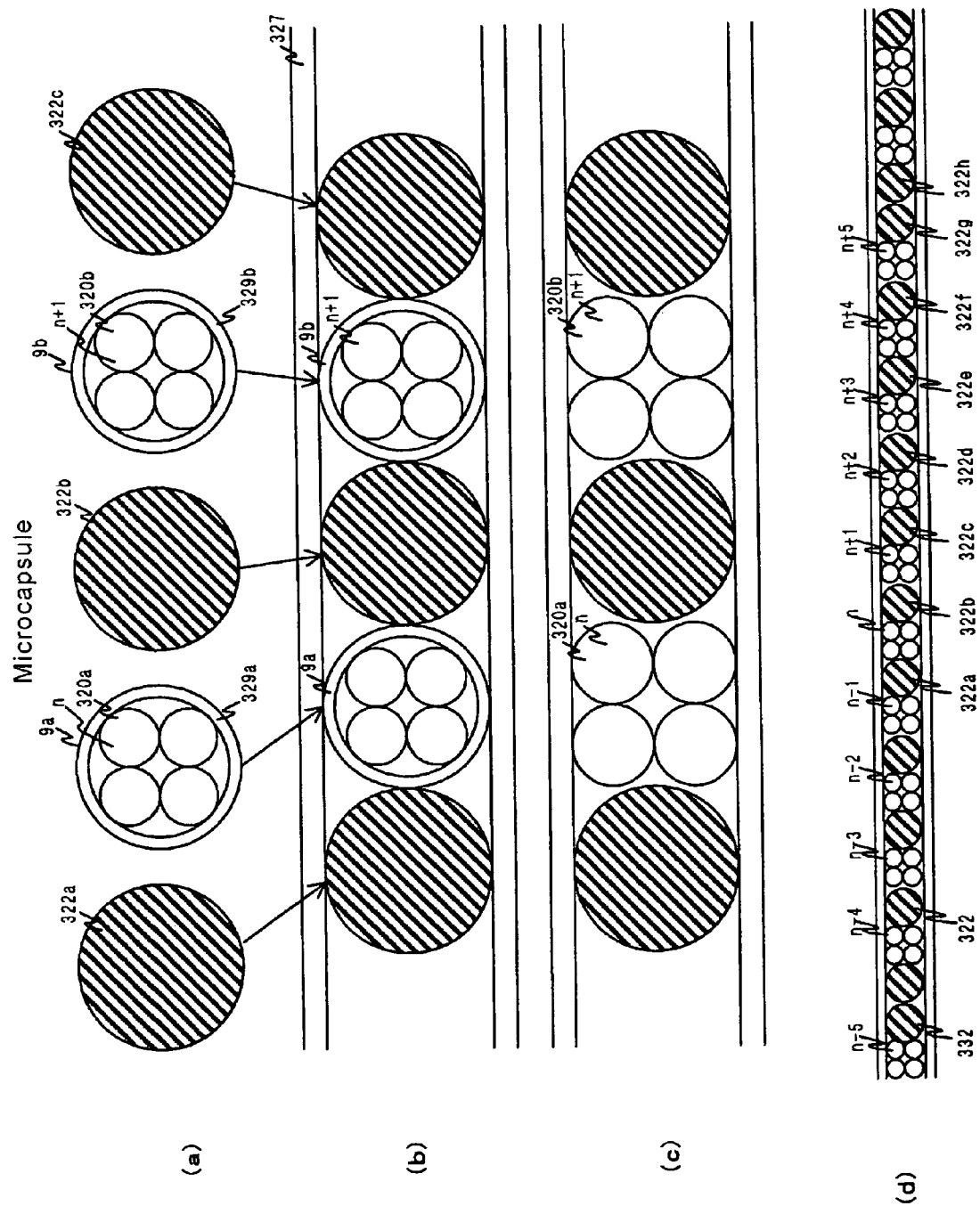

A method for forming a microcapsule containing a plurality of DNA beads will described with reference to FIG. 53. As shown in FIG. 53b, a microcapsule 9a which consists of a microcapsule 9 containing a plurality of DNA beads 320a (smaller than the microcapsule 9) having a $n^{th}$ capture DNA, a microcapsule 9b which consists of a microcapsule 9 containing a plurality of DNA beads 320b having a $(n+1)^{th}$ capture DNA are arranged in the glass tube 327 by using procedures described in FIG. 50 and the like, and those microcapsules 9a and 9b are spaced by mark beads 322a, 322b and 322c. Then, temperature of the glass tube 327 is increased by $T_0$ with respect to the reference circumstance temperature 0° C. (i.e., 10° C.) so that the envelopes 329 of the microcapsules 9 melt. Consequently, the envelopes 329 become liquid to flow out, and the plurality of DNA beads 320a, 320b are arranged between mark beads 322a, 322b and 322c as shown in FIG. 53c. When diameter of beads becomes small, sensitivity is increased because the total surface area of the beads becomes large. By arranging consecutively two or three mark beads,. e.g., mark beads 322g and 322h as shown in FIG. 53d, address information containing more information may be buried.

Method for Reproducing Biomolecule Beads

A method for reading out the information from the glass tube 327 containing biomolecule beads shown in FIG. 54a and the like will be described.

Biomolecules immobilized in the biomolecule layer on the surface of DNA beads are hybridized with biomolecules such as DNA and the like in a sample labeled with a fulorophore by passing through the sample in to the glass tube 327. Then, the sample is washed out to complete a glass tube containing specific DNA beads 320 labeled with a fluorophore.

Figure 14:
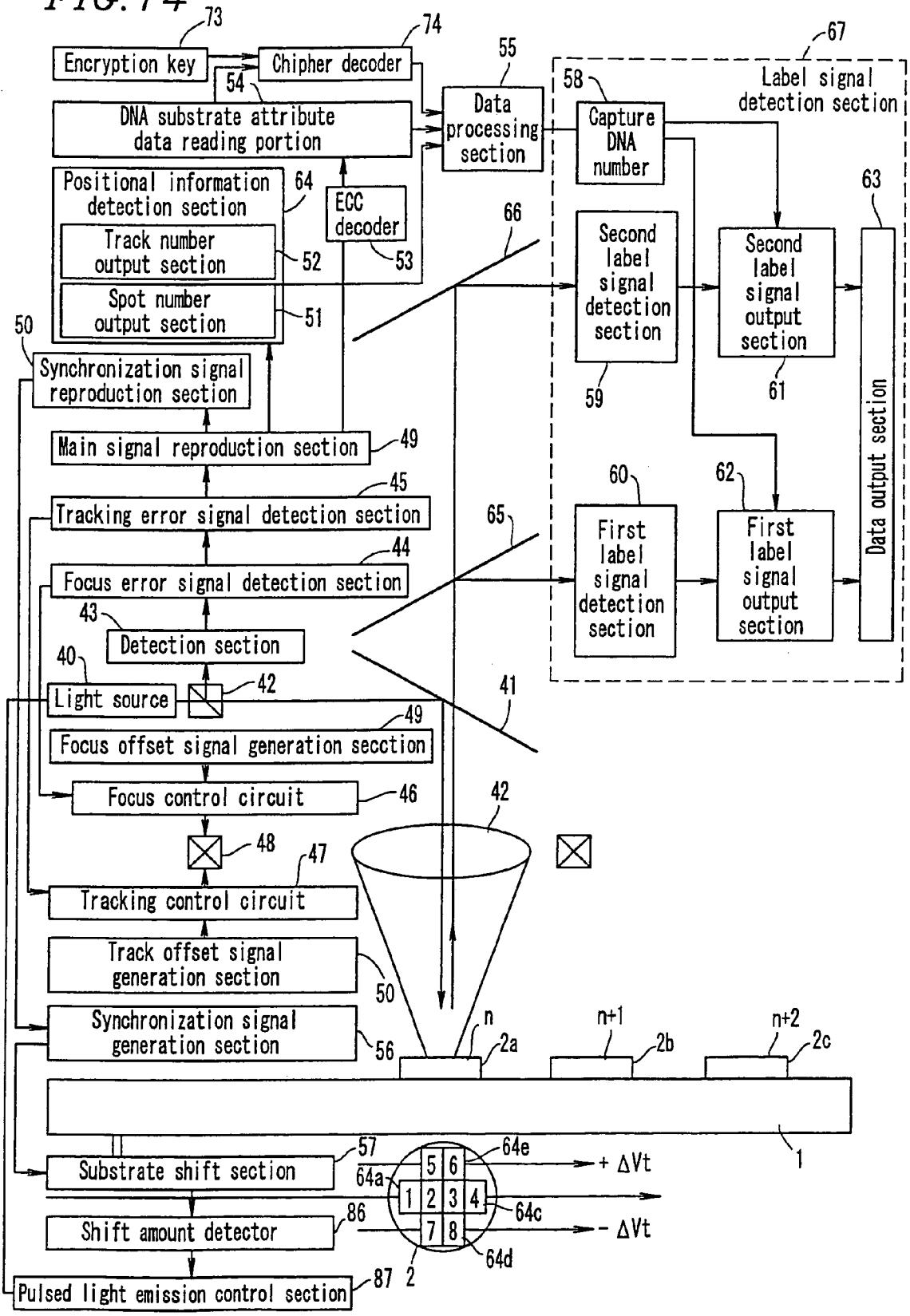
Figure 54:
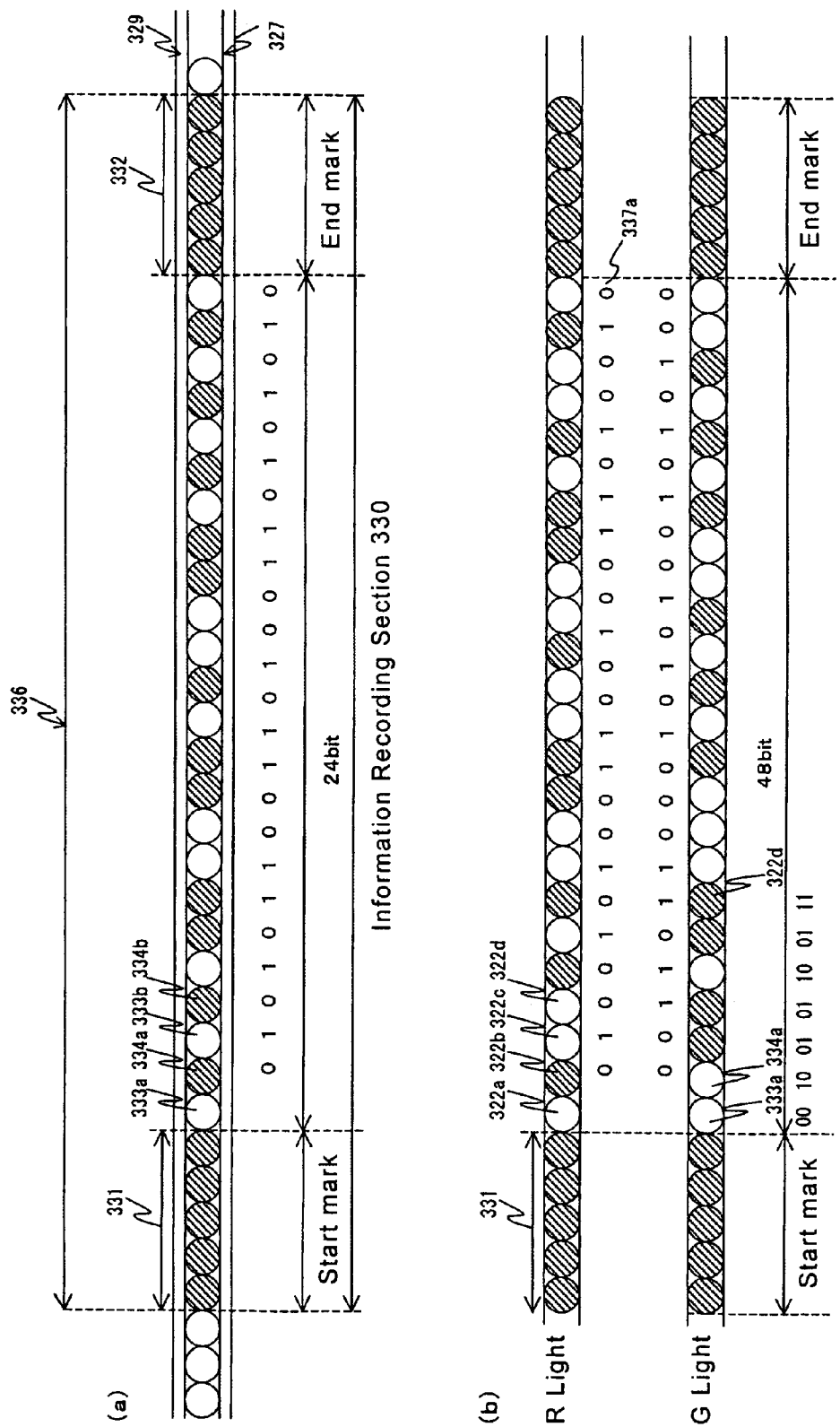

In order to read out information on beads in this glass tube, a test apparatus shown in FIG. 14 is used in which a substrate 1 is substituted with a glass tube 327 as shown in FIGS. 51c, 52 or 54a. A structure of a biomolecule is analyzed by irradiating a light onto beads with shifting the glass tube 327 toward the direction indicated by arrows using the substrate shift section 57, by observing reflecting light, transmitted light, fluorescence and the like therefrom to recognize the hybridization state. Firstly, light emitted from an excitation light source 40, such as laser or the like, which has been converged, is irradiated on beads in the glass tube 327. A reflector 343 is arranged in the opposite side of the light source 40 with respect to the glass tube 327. When the light is converged on DNA beads, the light transmitted the DNA beads because the DNA beads are light-transmissive. The transmitted light is reflected by the reflector 343 to re-transmit the DNA beads 320 and the like, and travel through lens 42 and to mirror 41. Then, the light which transmitted the DNA beads is detected by a detection section 43 as an electric signal. On the other hand, when the light is converged on mark beads, the light attenuates because the mark beads absorb the light. Therefore, the light reflected by the reflector 343 also attenuates, and the light further attenuates after passing by the mark beads. Consequently, the electric signal generated at the detection section 343 becomes small. Thereby, a modulation signal intermittently cut-off according to a sequence of the mark beads with shifting the glass tube 327 toward the direction indicated by arrows using the substrate shift section 57, which generates at the detection section 43, is reproduced by a main signal reproduction section 69. In the case where beads are arranged in the glass tube 327 as shown in FIG. 52, a difference in a number of beads between a part of two serial mark beads 322a, 322b and a part of a single mark bead 322c in a first region where in a number of mark beads is less is used as a synchronization signal to demodulate address information. Then, as shown in FIG. 54a, by interpreting a light-transmissive mark bead 333 as "1", and a light-absorbing mark bead 334 as "0", a data row "0101011 . . . " is reproduced. This data row contains identification information identifying glass tubes 327. Therefore, glass tubes can be identified from each other.

A main test system 174 comprises a test section 175, and the detection section of FIG. 14 is contained in this test section 175. The identification information of the glass tube 327 is transmitted via a communication section 176 and a communication path 177 such as the Internet and the like to a sub test system 178. A data base 184 contains chip IDs, which are data indicating a sequence status of DNA beads in glass tubes. These data are transmitted to a diagnosis system 187 of the main test system 174 via the communication path 177. Thereby, a DNA sequence of a biomolecule immobilized on a DNA beads 320 labeled with a fluorophore can be recognized and, then, structures of DNA, RNA or a protein from a specimen can be presumed. Based on the structure, a diagnosis section 188 diagnoses a disease of the organ from which the specimen was sampled. As discussed above, according to the present invention, since identification information can be obtained by the identical test system, the possibility of incorrectly reading out a DNA attribute is advantageously eliminated, leading to a more reliable test or diagnosis.

Method for Burying Data

A method for storing attribution information of DNA array 329 such as a manufacturer's name, an unique number such as an ID number, a sequence pattern number of a capture DNA (a probe) and the like according to a sequence status of mark beads 322 is described in FIGS. 54a and 54b. As shown in FIG. 54a, an information storage region 330 is provided in a terminal section such as a start section or an end section for reading-out beads in the DNA array 329. This array comprises a region expressing information, which contains light-transmissive mark beads transmitting a light having a specific wavelength and light-absorbing mark beads attenuating the light having a specific wavelength between a start mark 331 consisting of five mark beads 322a, 322b, 322c, 322d and 322e, and an end mark 322 consisting of five mark beads 322f, 322g, 322h, 322i and 322j. In the case of FIG. 54a, by interpreting a mark bead 333a transmitting a light having a specific wavelength, for example, 600 nm for red, as "0", and a mark bead 334a attenuating the light as "1", a 24-bit datum "010101100110100110101010" can be read out by using the light having a specific wavelength.

Next, in FIG. 54b, when reading-out with a red light (R light), the mark bead 333a transmits the Red light, and when reading-out with a blue light (B light), the bead also transmits the B light. Thus, the mark bead 333a is considered as being light-transmissive and a symbol "00" is assigned. The mark bead 333b is considered a being blue and a symbol "10" is assigned because it transmits the R light and not the B light. The mark bead 333c is considered a being red and a symbol "01" is assigned because it transmits the B light and not the R light. For the mark bead 333d, a symbol "11" is assigned because it transmits neither the R light nor the B light.

Method for Arranging Enlarged Beads

Figure 55:
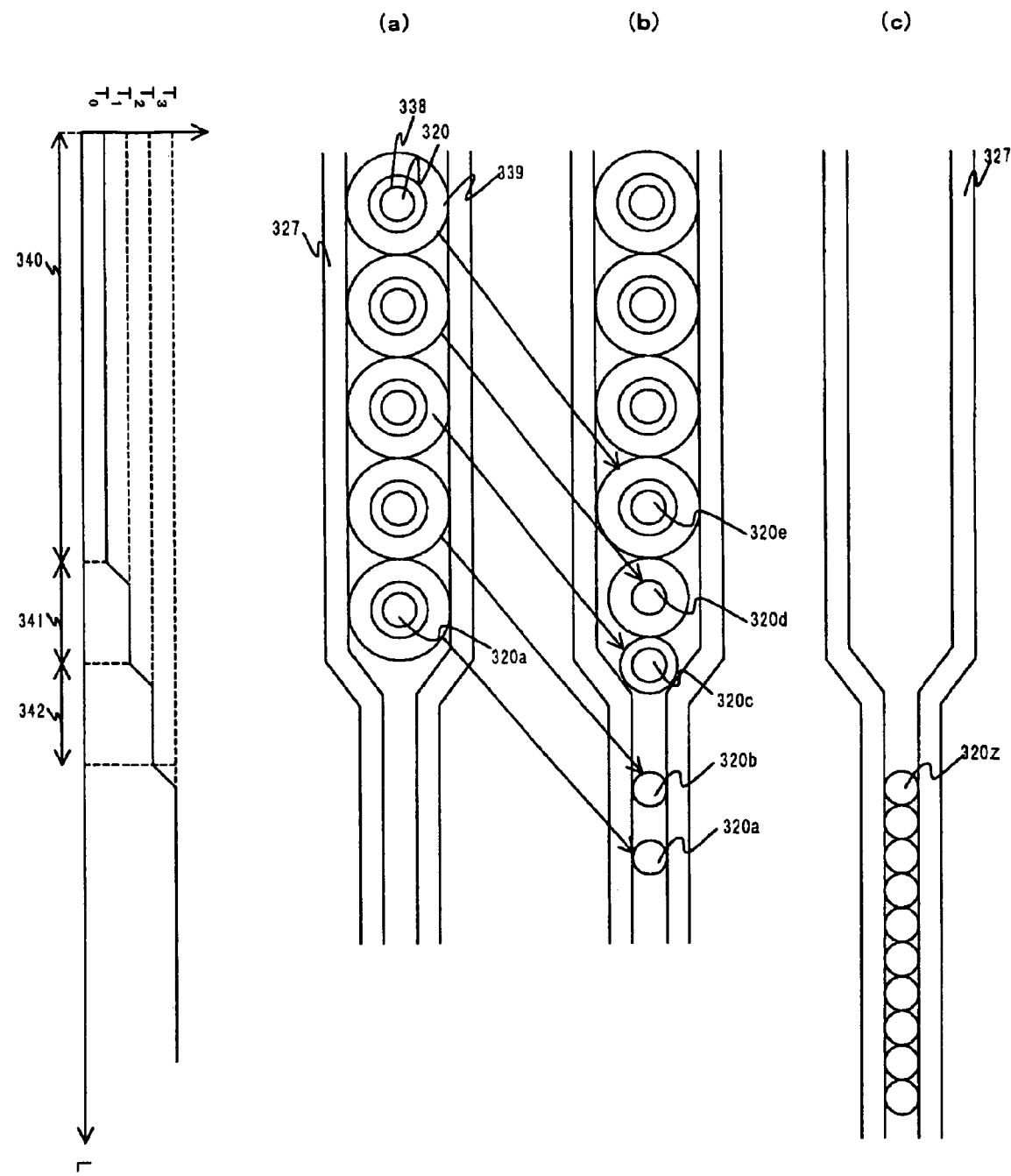

FIG. 55a shows a glass tube 327 incorporating DNA beads 320 immobilizing various DNA sequences therein, wherein the DNA beads 320 are covered with a two-layer coating consisting of a first shell 338 having a melting point of $T_1$ and a second shell 339 having a melting point of $T_2$ thereon. Then, the glass tube 327 is heated to make a temperature profile consisting of a first region 340 at a temperature $T=T_0$, a second region 341 at a raised temperature $T_1>T_0$, and a third region 342 at a further raised temperature $T_2>T_1$. Consequently, as shown in FIG. 55b, the DNA beads become small like a DNA bead 320d in the second region 341 due to melting of the second shell 339. In the third region 342, the DNA beads 320c become further small like a DNA bead 320b due to melting of the first shell 338. By repeating this procedure, shell-free DNA beads 320z and the like are arranged in the glass tube 327. In this method, since the beads are arranged in the enlarged state, it becomes easy to handle the beads. In addition, since the DNA beads are protected with the first and second shells, the possibility of peeling off probes in the process. Further, a dry method can be used.

Example 3

Fabrication Example of Biomolecule Chip (3): Tube Method

Next, a specific method for fabricating a biomolecule chip according to the present invention and a configuration thereof will be described where a fiber convergence system is described as an example. Note that although in Example 3 a fiber convergence type fabrication method is used as an example, a method for burying data (e.g., address, chip ID, and the like) by arrangement of biomolecule spots, which is a feature of the present invention, can be applied to other methods, such as a PIN method, an ink jet method, a semiconductor masking method, and the like.

In this method, initially, a probe 131 corresponding to a specific DNA, RNA and protein is injected together with a gel solution into a hollow thread tube 130 from a container 132 containing the probe 131 in the gel form. Different probes 131a, 131b, 131c, 131d, etc. are injected into respective tubes 130a, 130b, 130c, 131c, 130d, etc., which are then bundled in an X direction, i.e., horizontally, to form a sheet 133 as shown in FIG. 33(b). Further, the bundled sheets 133a, 133b are piled so that the tubes 130 are arranged in a matrix to form a block 137 as shown in FIG. 33(c). The tubes may be arranged in a circle to form a column-like block.

In one embodiment of the present invention, a mark tube 134 for a mark indicating an address or data is placed in the block. Note that in a second method, a mark tube 136 is placed in the block, which comprises a probe solution 135 or a tube 130 in which a material for reflecting, absorbing, or emitting fluorescence having a specific wavelength is contained. The mark tube 136 will be described in detail below. Although FIG. 33(c) shows a 10×10 matrix, the actual matrix has a side of several hundreds to several thousands of tubes.

The block 137 is sliced in a Z direction, so that a chip 138 is completed. The chip 138 is fixed on a fix plate 139. The fix plate 139 is used to fix a chip and may comprise a container for holding a specimen, and is shipped in this form. The fix plate 139 is used without modification to perform testing. On the fix plate, a fix plate ID 140, which varies depending on corresponding attributes of probes, is recorded in the form of a bar code, characters, or a bit pattern. A chip ID for managing a process control or the attribute data of a chip is recorded in the first sheet 133a by a method for burying data according to the present invention. This attribute data can be used to identify chips having different probe sequences. Therefore, by checking, it is possible to detect when an incorrect fix plate ID 140 is provided to a chip 138.

Method for Burying Data

Figure 35:
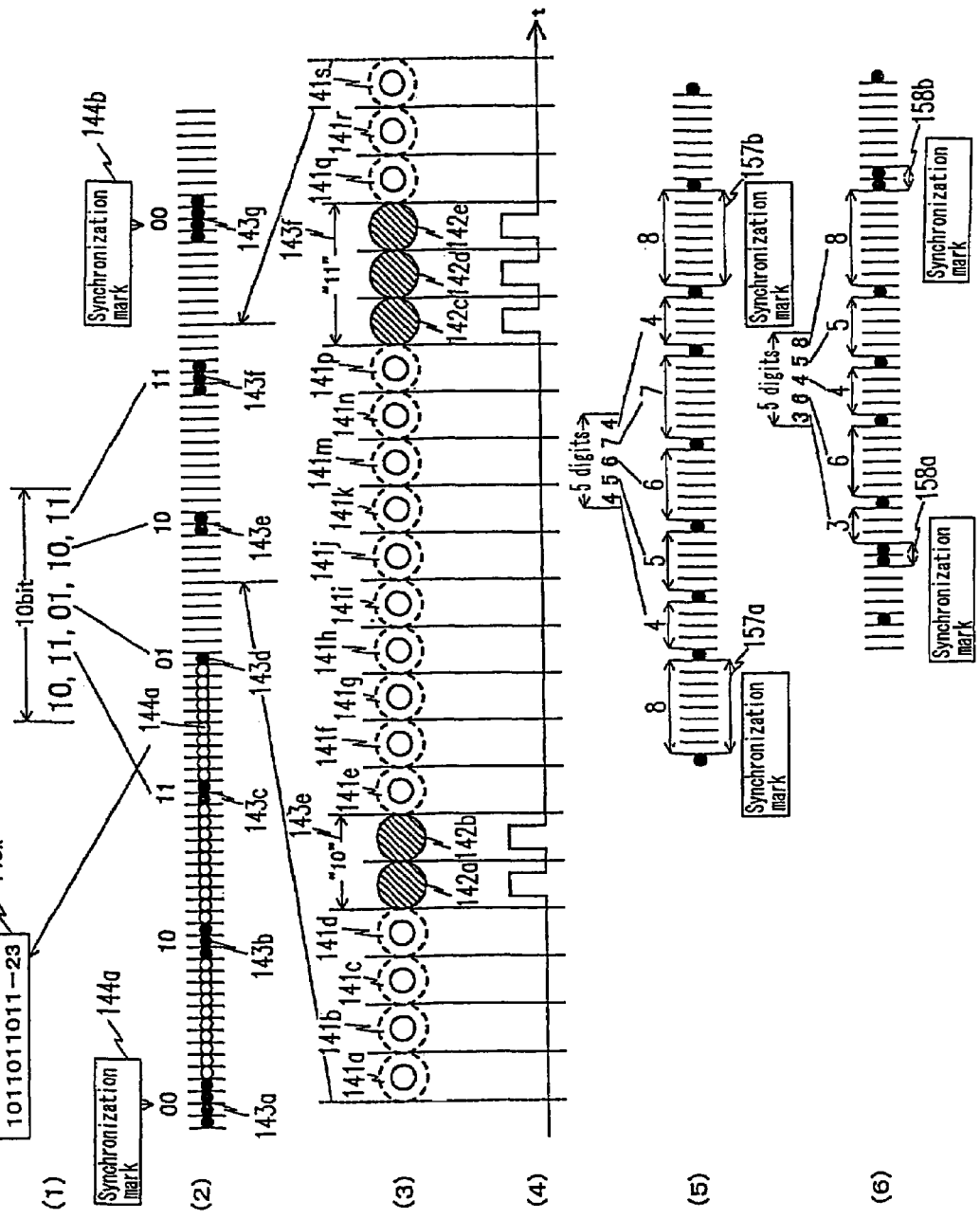

A spot of each probe is placed on the chip 138. Data is buried in an arrangement of spots. A spot containing the probe 131 for detecting DNA or protein is herein referred to as a DNA spot 2. Such a spot may also be called biomolecule spot. Now, a method for burying data will be described. Specifically, as shown in FIG. 35(3), for example, 10 biomolecule spots 141e to 141p are aligned in an x direction. Two mark spots 142a, 142b are placed at the left end and three markspots 142c, 142d, 142e are placed at the right end. Firstly, the case where the mark spots include no biomolecule will be described. The case where the mark spots include a biomolecule(s) will be described later.

A mark spot has an optical property different from a biomolecule spot 141 in terms of specific wavelength. Specifically, a mark spot has a reflectance or absorbance with respect to a specific wavelength, or the presence or absence of fluorescence or the intensity of fluorescence with respect to a specific wavelength, different from a biomolecule spot. Therefore, a mark spot can be clearly distinguished from the biomolecule spot 141. For example, when there is a difference in reflection or absorption with respect to excited light or irradiation, the mark spot can be optically clearly distinguished from the biomolecule spot as indicated by hatched lines in FIG. 35(3). The same effect can also be obtained when the wavelength of fluorescence of the mark spot 142 with respect to excited light is different from the wavelength of fluorescence of the biomolecule spot 141. The intensity of reflected light or fluorescence obtained by irradiating the mark spot with light having a specific wavelength is illustrated in FIG. 35(4). A group of the mark spots 142 in (3) are collectively called identification mark 143. 2-bit codes, "10", "11", and the like are assigned to respective identification marks 143e, 143f. FIG. 35(2) shows a general view including the identification marks 143e, 143f where part of biomolecule spots 141 between identification marks are omitted. This figure shows 7 identification marks 143a to 143g, to which codes 00, 10, 11, 01, 10, 11, and 00 are assigned, respectively. When the identification marks 143a, 143g containing 4 consecutive mark spots 142 are used as synchronization marks 144a, 144b, the five identification marks 143 between the synchronization marks 144 can be used to bury 10-bit data, i.e., 10, 11, 01, 10, and 11.

By reading these marks with a scanning beam or a CCD in a test apparatus, the 10-bit data is read from this region. If these 10 bits are used as, for example, address data, the address of this region, "1011011011", can be obtained only by reading the 10 bits. Thus, a third biomolecule spot 141x to the right of the identification mark 143c is $23^{rd}$ biomolecule spot in address "1011011011". Therefore, the identification number 145 of a biomolecule spot can be identified as "101101011-23". Therefore, all biomolecule spots 141 on a chip can be individually identified without counting spots from an end of a matrix. Thus, a conventional method for identifying a spot by counting spots from an end of a matrix to the x, y coordinates of the matrix corresponding to that spot, is made unnecessary.

By reading out the attribute information of a biomolecule spot 141 corresponding to the identification number 145 from an attribute table 146 in FIG. 40, various tests and diagnoses can be made possible. The attribute information contained in the attribute table 146 of FIG. 40 includes the sequence or genetic information, or marker information of a specific disease, of a biomolecule having this identification number, or DNA, RNA, or other substances hybridizable to this biomolecule probe, and the like.

In an actual fabrication method, for example, a tube piling method, errors in piling are accumulated, so that it is less likely that the x and y coordinate axes of a matrix can be precisely formed. In this case, therefore, the identification number of each biomolecule spot identified from such x and y coordinates is highly likely to match the correct identification number. An incorrect identification number leads to an incorrect test result. In the case of a DNA test or the like, when an incorrect test result is used for diagnosis of a patient, false diagnosis occurs frequently, potentially causing a serious problem.

In contrast, the present invention has an advantageous effect that the identification number of a biomolecule 141 can be precisely identified by reading locally the vicinity of the biomolecule 141 even if biomolecule spots are not arranged in a precise matrix. Biomolecule chip fabrication methods other than a semiconductor process can be used to fabricate a large number of chips containing biomolecule spots. Even in the case of a perfect matrix arrangement obtained by a semiconductor process, as the number of spots is increased, error occurs in counting spots on a test apparatus, potentially resulting in an incorrect identification number. In the present invention, it is not necessary to count spots with respect to x and y from an end of a biomolecule chip, and therefore, counting error does not occur. Moreover, the identification number of each biomolecule spot can be obtained by reading only the vicinity of the biomolecule spot, whereby the identification number of a desired biomolecule spot can be identified in a short time.

Specific procedures are as follows. For example, it is assumed that DNA, RNA, or the like with a label emitting fluorescence with a wavelength of $\lambda_2$ has been hybridized to a biomolecule spot 141x. When the biomolecule spot 141x is irradiated with excited light having a wavelength of $\lambda_1$, the biomolecule spot 141x emitting fluorescence with a wavelength of $\lambda_2$ can be observed. According to the data burying method of the present invention, the identification number of the biomolecule spot 141x is obtained and the sequence of the DNA or the like can be obtained from an attribute table, thereby making it possible to analyze or test specimens.

Example 4

Test using Biomolecule Chip

Test Procedures

Figure 33:
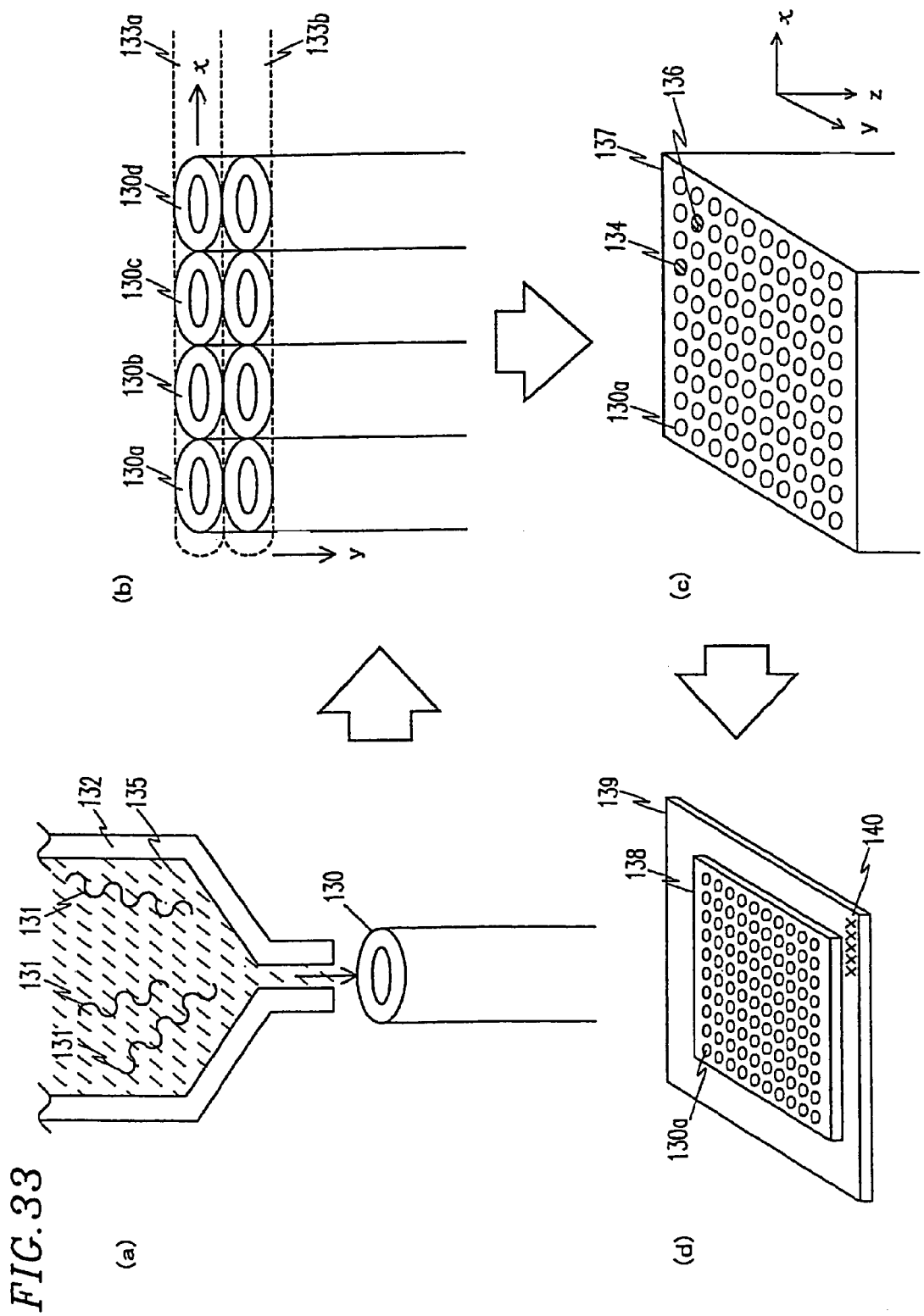
Figure 41:
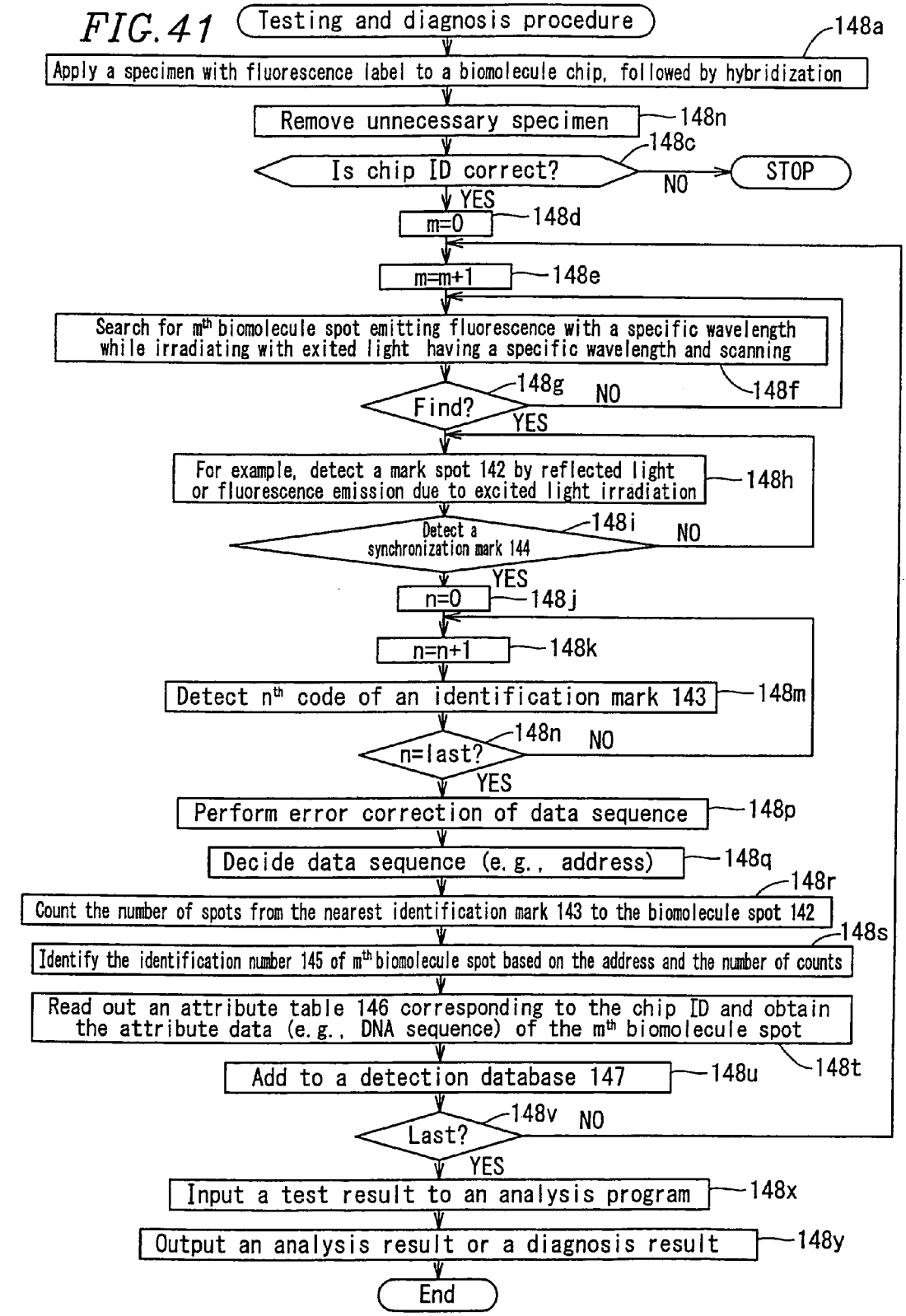

Procedures for test or diagnosis will be described with reference to a flowchart shown in FIG. 41. Initially, in step 148a, a specimen with a fluorescent label is provided and hybridized to a surface of a biomolecule chip 138 fabricated by a chip fabrication process, such as a tube method, a semiconductor process method, an ink jet method, a PIN method, or the like. Unhybridized specimens, which are unnecessary, are removed in step 148b. This chip is loaded into a laser scanning type test apparatus or a CCD readout type test apparatus shown in FIG. 14 described later. In step 148c, chip ID written in the first line of the chip 138 or/and a fix plate ID 140 on the fix plate 139 of FIG. 33 is read out by a light beam, CCD, or the like, so as to check the chip ID or the fix plate ID against a predetermined one. Next, these IDs are checked against a predetermined ID list. If a result of the above-described check is incorrect, the process is stopped. If the result of the check is correct, an attribute table 146 (see FIG. 40) corresponding to the chip ID is obtained via a network 150, such as the Internet, LAN, or the like, and is temporarily stored in a memory 151 of a test apparatus 149.

The process goes to a test mode. In step 148d, m is set to be 0. In step 148e, m is increased by one. In step 148f, a surface of the chip is irradiated with excited light having a first wavelength of $\lambda_1$. While scanning the chip using a laser or a CCD, a wavelength separation filter, such as mirrors 65, 66 in FIG. 14, is used to search for $m^{th}$ biomolecule spot emitting fluorescence with a specific wavelength. The search is continued until the spot is found in step 148g. When the $m^{th}$ biomolecule spot is found, the chip is irradiated with excited light or reference light in step 148h. An optical property of a mark spot 142, such as reflectance or the like, with respect to the wavelength of excited light is set to be different from that of a biomolecule spot 141. Therefore, as shown in FIG. 35(2), the mark spot can be optically distinguished from the biomolecule spot using excited light or reference light. In this case, the same effect is obtained even when the mark spot 142 emits fluorescence having a wavelength different from that of the biomolecule spot 141. Therefore, the mark spot 142 can be detected. In step 148j, n is set to be 0. In step 148k, n is incremented by 1, the code of $n^{th}$ identification mark 143 is identified. When the process is repeated until n reaches the last n in step 148n, one data row is obtained. This data row contains an error correction code 152 in order to improve the reliability of the data row. Therefore, the data row is subjected to error correction in step 148p, and the data row having no error is obtained in step 148q. In step 148r, by counting the number of spots from an identification mark 143 closest to a subject biomolecule spot, the total number of biomolecule spots from a synchronization mark to the subject biomolecule spot 141 (e.g., 141x) as shown in FIG. 35(2) can be obtained. In step 148s, the identification number 145 of the $m^{th}$ biomolecule spot is identified based on the address and the number of counters. In this case, the wavelength of fluorescence can be specified from a filter setting, and therefore, the label number of the fluorescence is identified.

In step 148t, the attribute table 146 corresponding to chip ID is read out from the memory 151, and the sequence data of DNA or the like having a specific identification number is retrieved as shown in FIG. 40. Therefore, the type of DNA, RNA, or a protein contained in a specimen can be obtained. In step 148u, this information and the identification number are registered into a test database 147 of the memory 151. In step 148v, it is checked whether any other biomolecule spots emitting fluorescence remain unread. If there is an unread spot, the process returns to step 148e and the biomolecule spot emitting fluorescence is located. If there is no unread spot, data of test database 147 is sent to an analysis program 155 instep 148x. In step 148y, an analyzed test or diagnosis result is output. Thus, the operation is completed.

As described above, according to the present invention, data, such as addresses, chip ID, or the like, is buried in the arrangement of biomolecule spots. Therefore, the identification number of a biomolecule spot of interest can be obtained from the arrangement of biomolecule spots or mark spots around the identification number of interest. This data can contain chip ID and chip attribute data as well as addresses. In this case, all data required for testing or analysis is obtained from a chip itself. If chip ID obtained from a chip is compared with the fix plate ID 140 of the above-described fix plate, incorrect fix plate ID can be checked in testing, thereby reducing the occurrence of erroneous detection due to incorrect fix plate ID caused by a mistake in a manufacturing process. Further, it is possible to distribute a biomolecule chip alone without a fix plate 139, whereby chip cost can be reduced.

Figure 34:
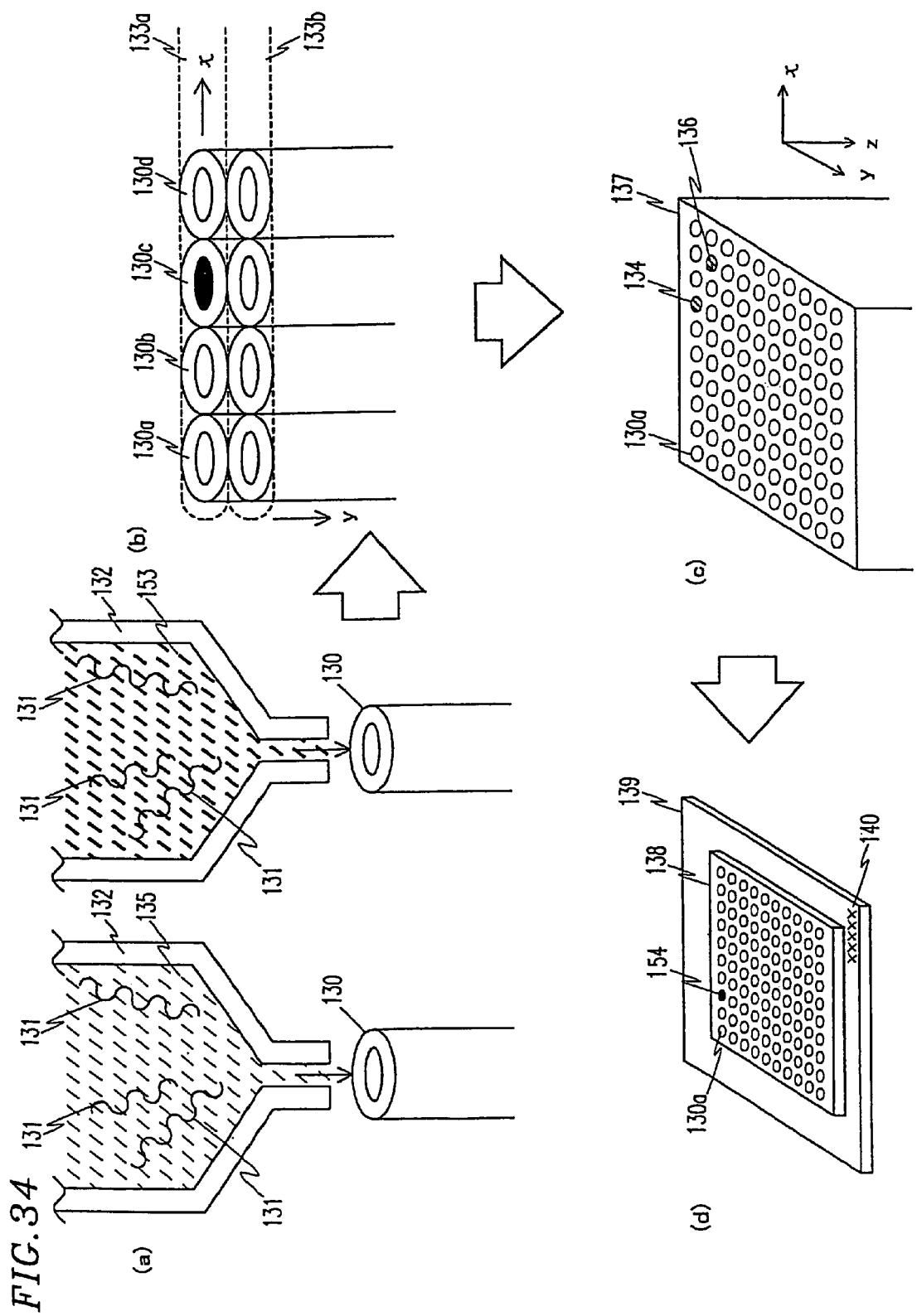

Note that, for the sake of simplicity, as shown in FIG. 35, the example in which the biomolecule spot 141 containing biomolecules and the mark spot 142' without a biomolecule, i.e., two types of spots, are used to bury data, such as addresses, has been first described. In this method, a mark spot is only added, and therefore, it is easy to manage fabrication. On the other hand, the density of biomolecule spots is disadvantageously reduced. For applications requiring a higher biomolecule spot density, as shown in FIG. 34(a'), a mark solution 153 having optical properties, such as a reflectance, absorbance, and refractive index with respect to a specific wavelength, fluorescence, and the like, different from the solution 135 in (a) is introduced into a tube. This tube is disposed as is a tube 130c in (b). As shown in (d), a mark biomolecule spot 154 is formed on a chip. When it is not efficient to prepare two biomolecule solutions, i.e., one with a mark and one without a mark, a mark may be attached to a tube 130 as represented by mark tubes 134, 136. In this case, although the sensitivity of such a mark is reduced, substantially the same effect as that of a mark biomolecule spot 154 described in FIG. 36 is obtained.

Figure 38:
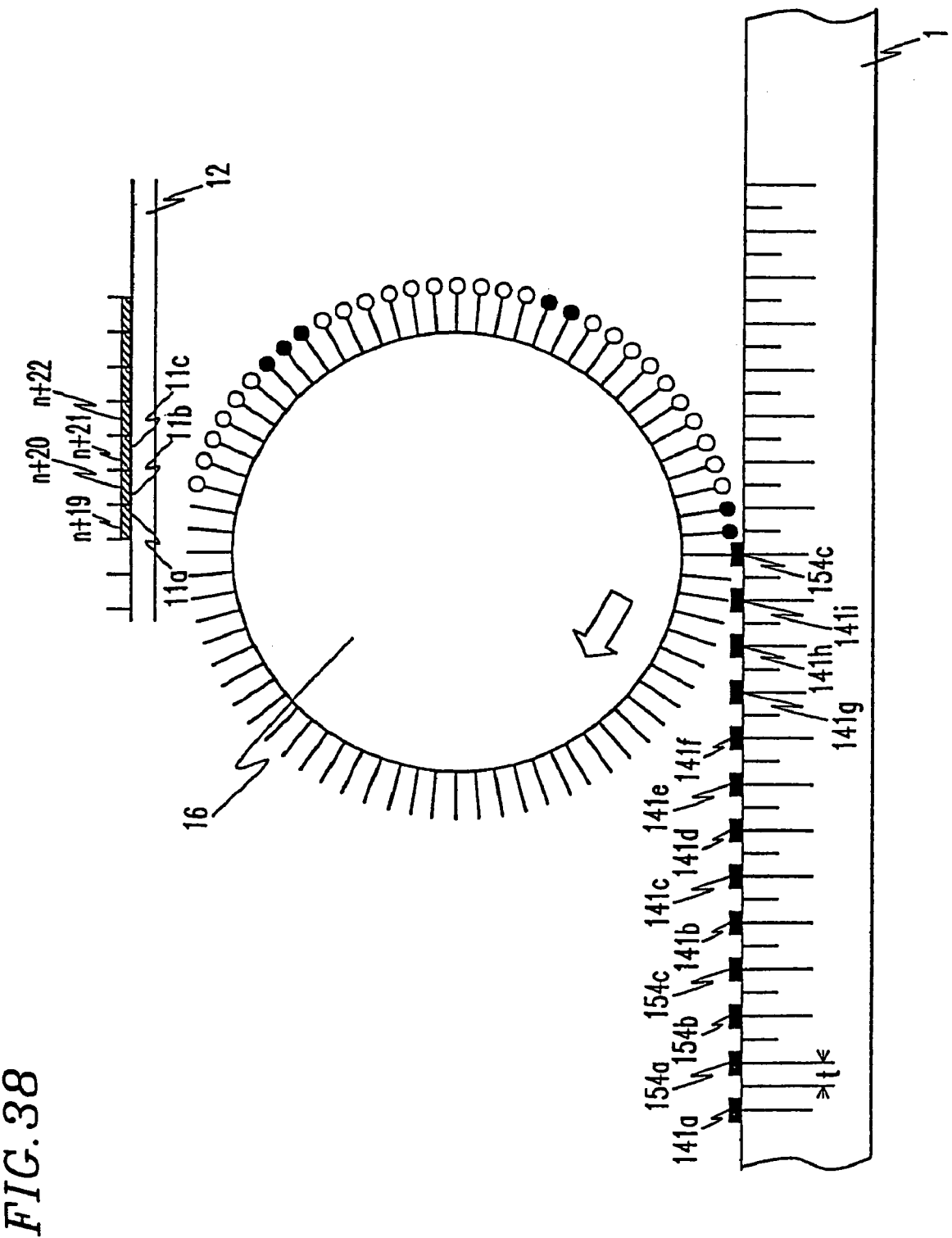

This fabrication method can be applied to other applications. In the case of a PIN method, a mark material is added to a main solution 4 or a sub-solution 8 as shown in FIG. 2 to prepare a mark solution 153. As shown in FIG. 38, biomolecules in a normal solution indicated by an unfilled circle and in a mark solution indicated by a filled circle are fixed to the substrate 1. Therefore, biomolecule spots 141a to 141i and the mark biomolecule spot 154 containing the mark solution 153 can be formed on the substrate 1 as shown in FIG. 38. The description of FIG. 38 is omitted because of substantially the same operation as in FIG. 3.

Figure 11:
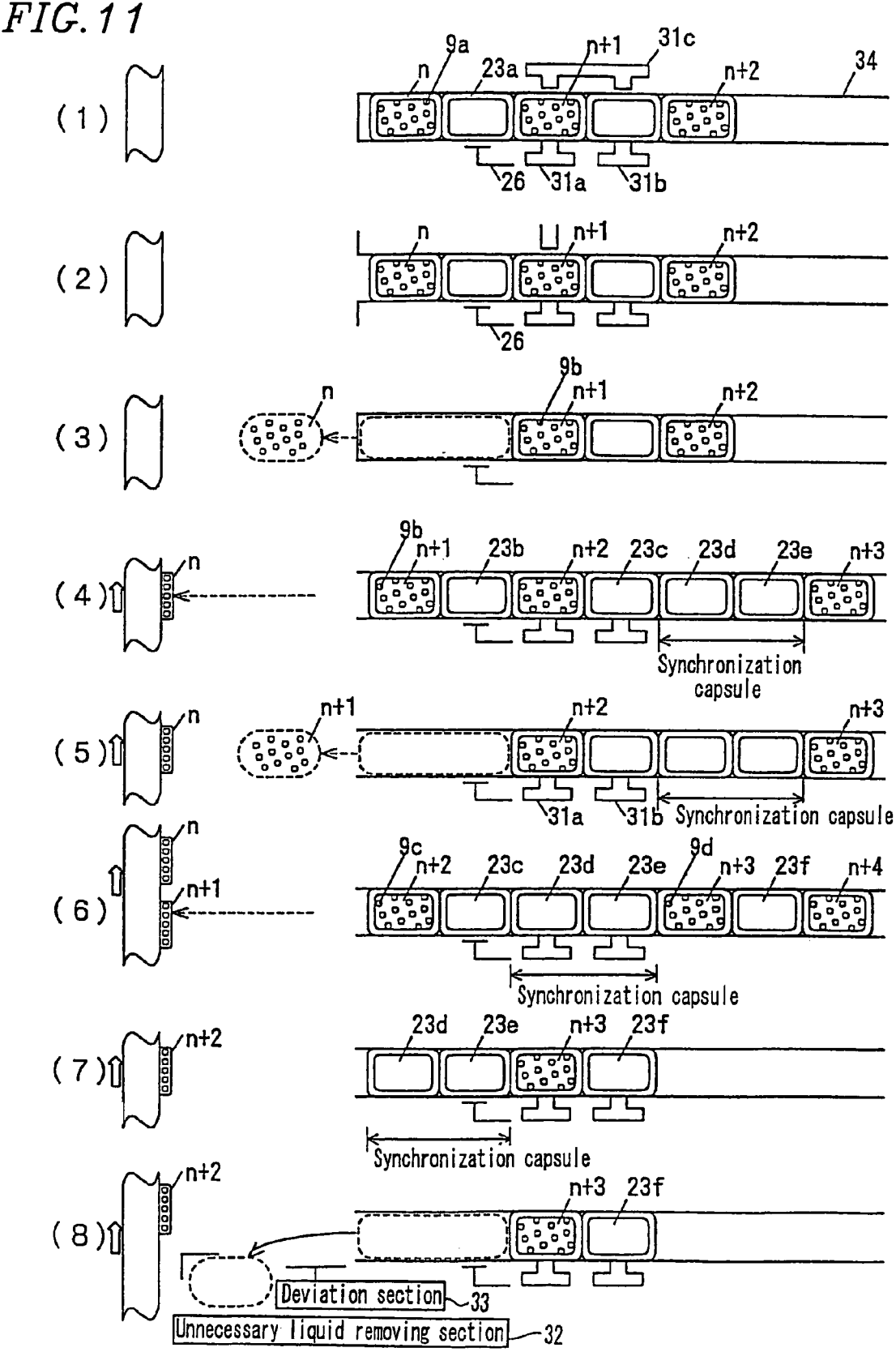
Figure 39:
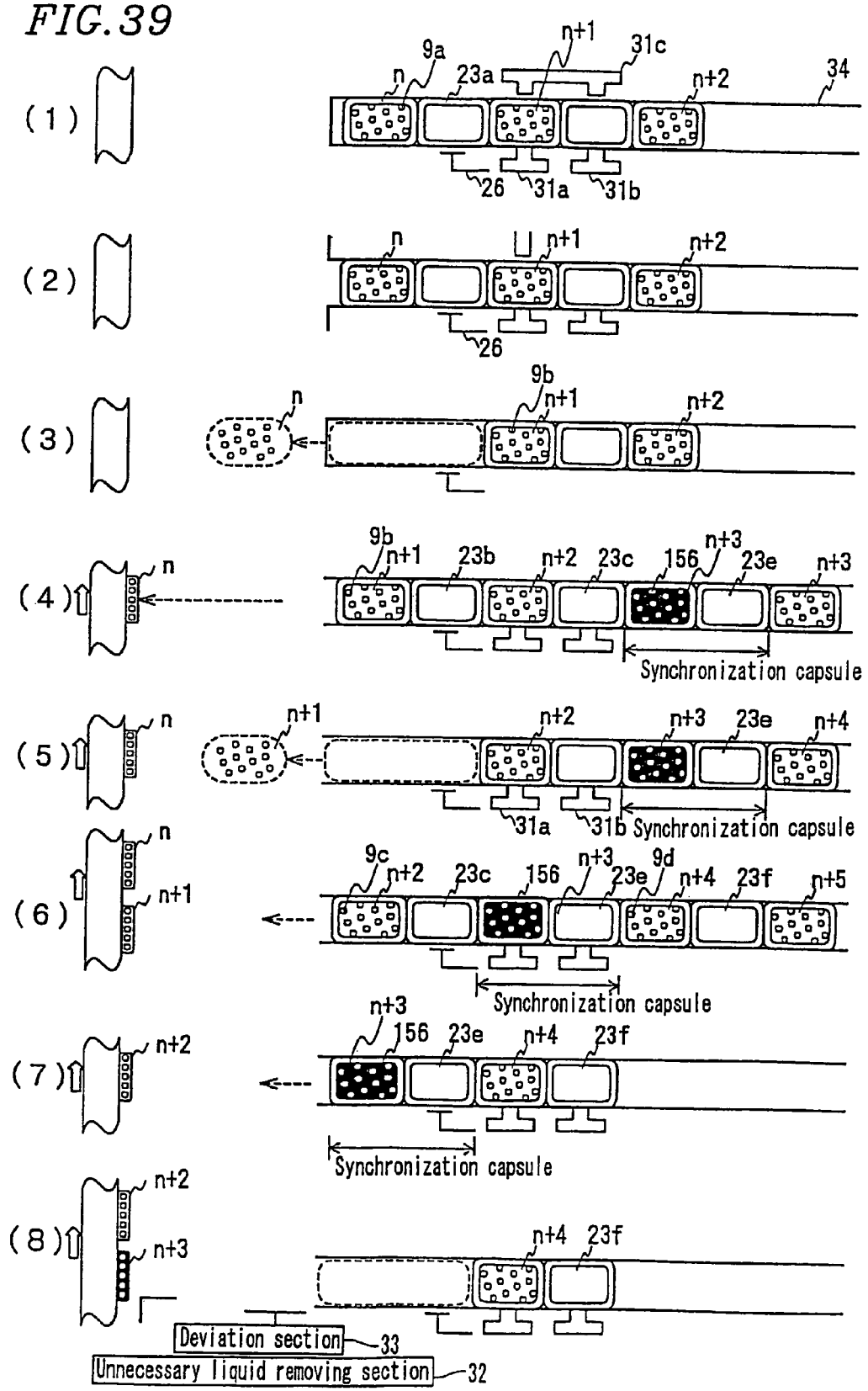

In the case of an ink jet method, a mark microcapsule 156 containing biomolecules and a mark solution is loaded instead of the synchronization capsules 23d, 23e shown in FIG. 11 so as to attach the capsule 156 onto the substrate 1 as shown in FIG. 39(4), (5), (6), and (7). Thereby, the same arrangement of the biomolecule spot 141 and the mark biomolecule spot 154 as in FIG. 38 can be obtained. Moreover, when a semiconductor mask is used, the same effect is obtained by piling a material for a mark on a mark biomolecule spot.

Figure 36:
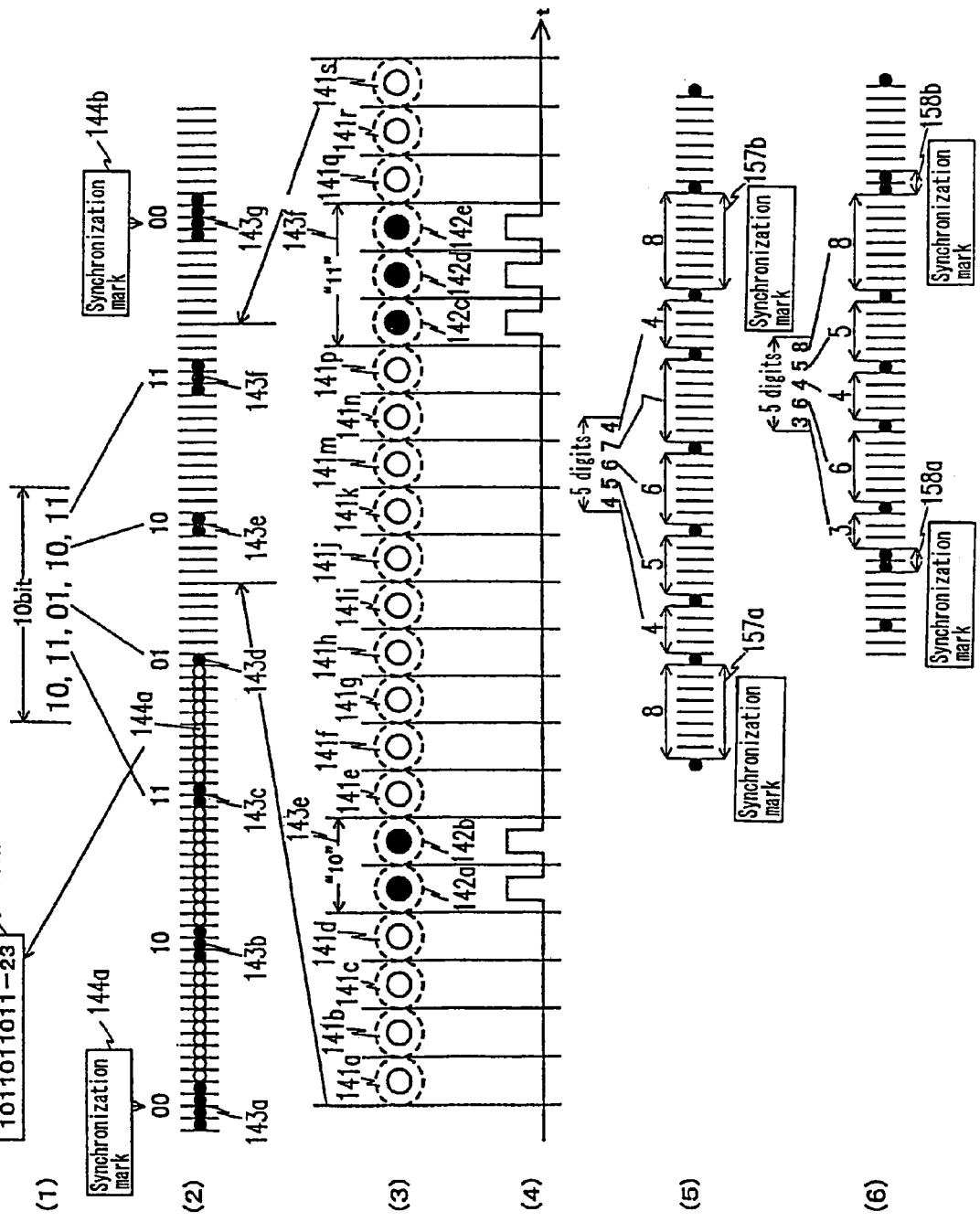

In the above-described three fabrication methods, the arrangement of the biomolecule spots 141 and the mark biomolecule spots 154 on the chip substrate is the same as in FIG. 36. The same effect as in the tube method can be obtained when the mark spot 142 is used instead of the mark biomolecule spot 154 as shown in FIG. 35. In this case, a solution or material is containing only a mark solution without a biomolecule is immobilized on a chip substrate in the three fabrication methods. The four exemplary fabrication methods have been described. The present invention can be applied to various biomolecule chip fabrication methods other than the four examples.

Returning to FIG. 35, another data burying method will be described. FIGS. 35(2) and (3) show that the mark spots 142 are arranged so that data, such as addresses or the like, is buried, where the number of consecutive mark spots is in the range of 1 to n. Hereinafter, a description in parentheses corresponds to FIG. 41. FIG. 36(5) shows that data is buried by changing the interval between the mark spot 142 (mark biomolecule spot 154) depending on the data. Specifically, two mark spots having an interval corresponding to 8 biomolecule spots is defined as a synchronization mark 157. The intervals between mark spots 142 (mark biomolecule spots 154) from the synchronization mark 157a to 157b are 4, 5, 6, 7 and 4. Therefore, data corresponding to 5 digits in the septinary number system, i.e., 7 to the power of 5 pieces of data, can be buried. This data can contain address data, error correction code, and chip attribute data. In this case, the mark spot can be easily detected since the mark spot has the longest interval.

FIG. 35 (FIG. 36) (6) shows a method in which two consecutive mark spots 142 (mark biomolecule spots 154) are arranged as a synchronization mark 158. In this case, the intervals between mark spots 142 (mark biomolecule spots 154) from a synchronization mark 158a to 158b are 3, 6, 4, 5, and 8. Therefore, 7 to the power of 5 pieces of data can be buried.

Figure 37:
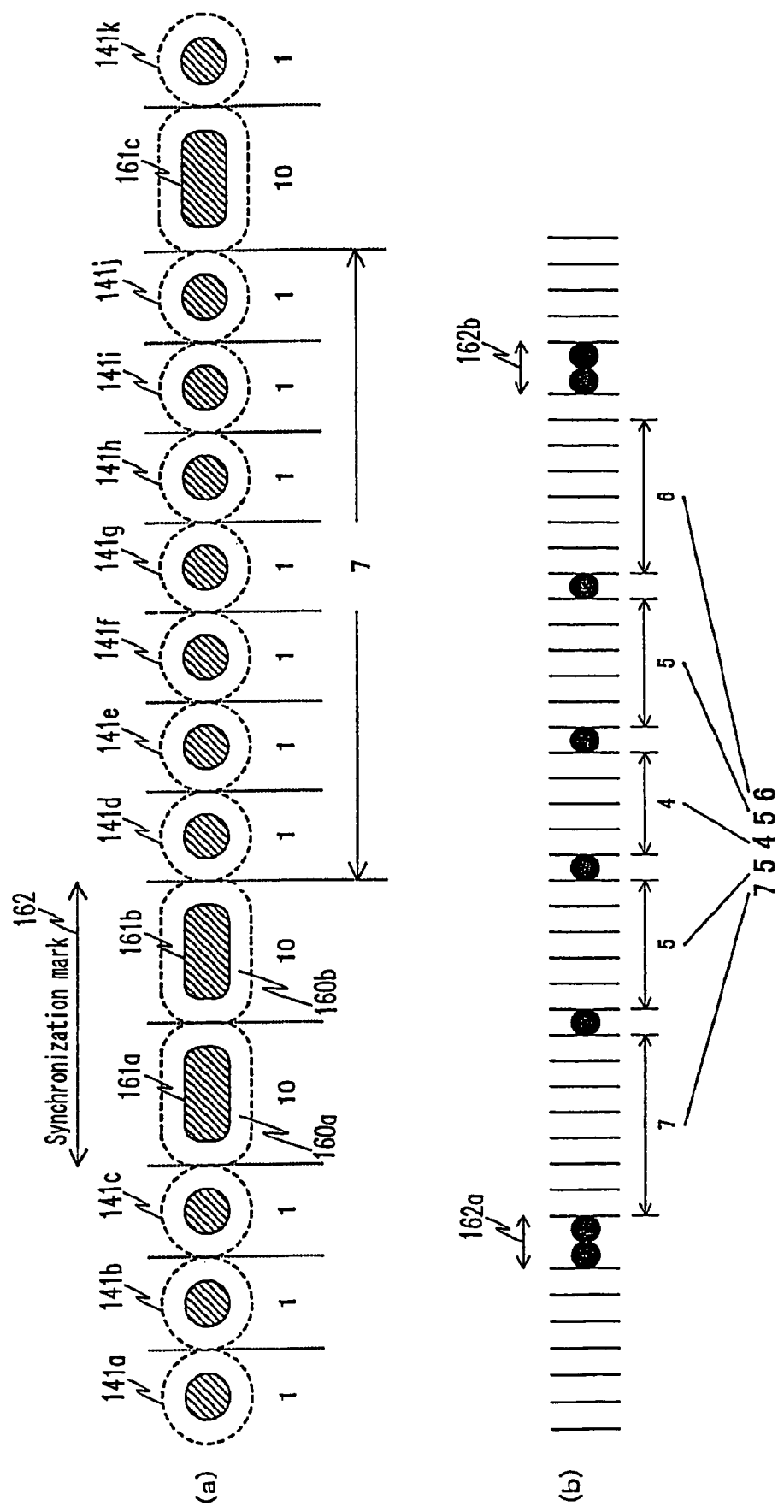

FIG. 37(a) shows an arrangement of long biomolecule spots 161a, 161b and 161c, and biomolecule spots 141a to 141k, which is obtained by a tube method using a flat tube 160. When the elongated biomolecule spot 161a is regarded as one mark spot, two contiguous elongated biomolecule spots 16a, 161b can be defined as a synchronization mark 162. Similar to the synchronization mark 158 in FIG. 35(6), 7 data is read from an arrangement of 7 biomolecule spots 141k, 141j in FIG. 37. Thus, as shown in FIG. 37(b), "75456", i.e., 5-digit data in the octanary number system can be buried between the elongated biomolecule spot 161b and the subsequent elongated biomolecule spot 161 (not shown).

Figure 42:
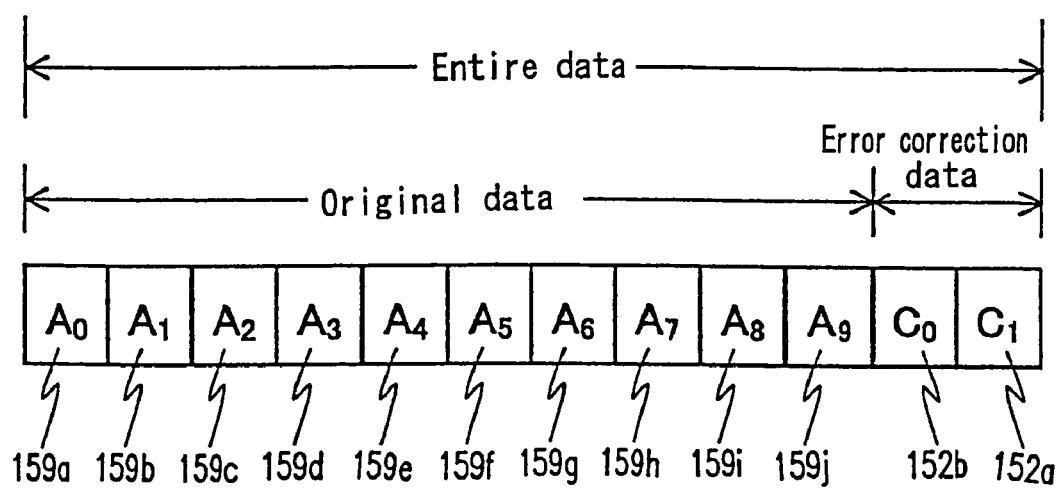

In the present invention, a method for correcting an error in data using error correction codes is adopted. In the case of 10 bits, as indicated in a data structure diagram in FIG. 42, 10-bit original data 159 ($A_0$ to $A_9$) is provided with 2-bit error correction codes 152 ($C_0$, $C_1$) produced from the original data 159 using Reed Solomon coding or turbo coding, thereby correcting an error. Therefore, the reliability of buried data is increased, so that an error is unlikely to occur in important data, such as addresses. In FIG. 42, an error correction code is used only in the horizontal direction. When a product code method in which an error correction code is additionally used in the vertical direction, it takes a longer time to perform operations and obtain original data. However, in this case, the reliability of buried data is improved.

Example 4

Detection Apparatus for Biomolecule Chip

In the above-described manner, a DNA chip or a DNA substrate, on which capture DNA is arranged, can be fabricated. This DNA substrate can be used to test DNA or a protein.

Figure 13:
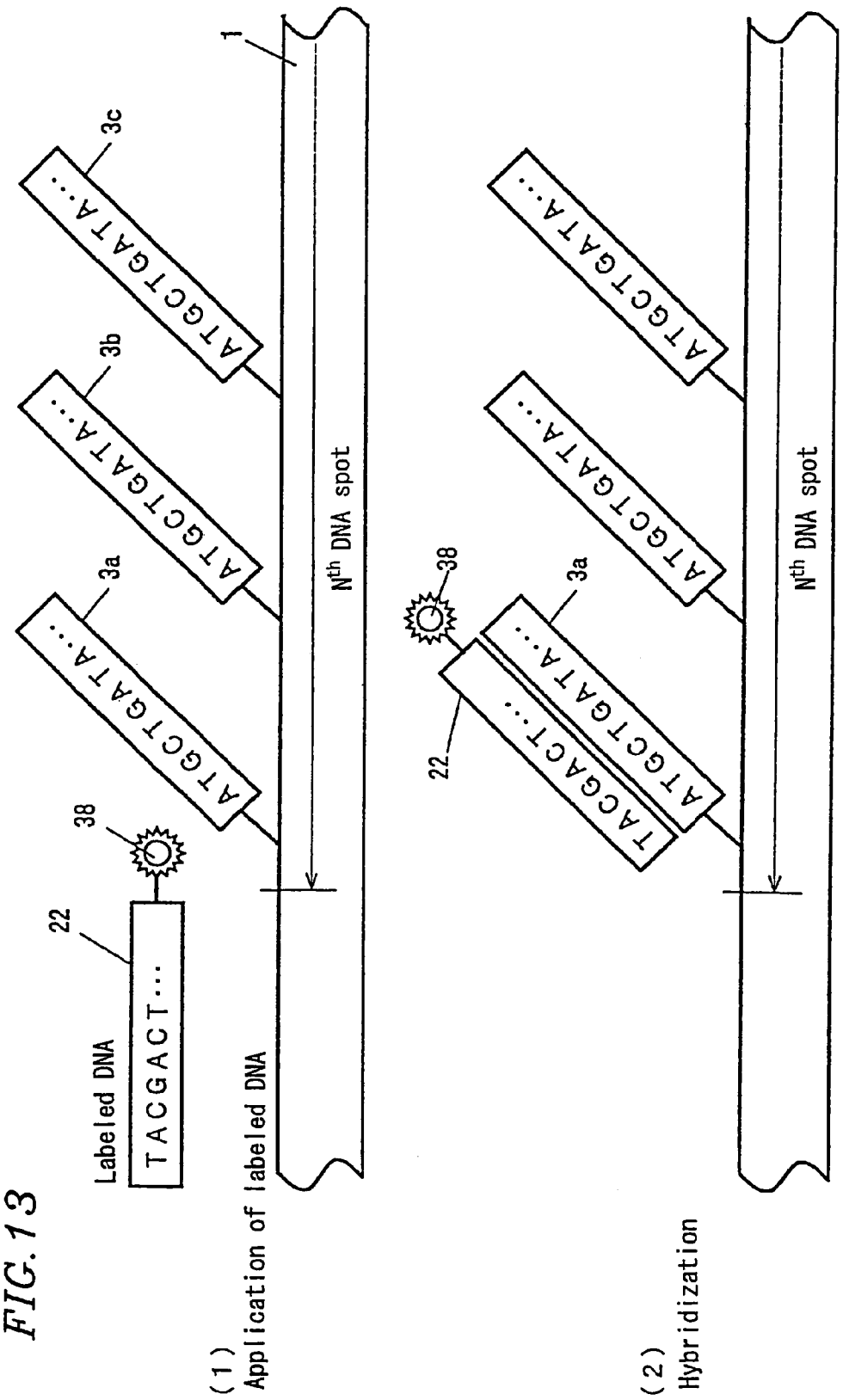

DNA, such as cDNA or the like, is extracted from a DNA specimen, and is labeled with a fluorescence material 38 to prepare labeled DNA 22. As shown in FIG. 13(1), the labeled DNA 22 is applied to a DNA substrate of the present invention. The DNA substrate is placed under specific conditions, such as heating at several degrees Celsius and the like, to carry out hybridization. As shown in FIG. 13(2), the labeled DNA 22 is coupled with capture DNA 3a in the $n^{th}$ DNA spot.

Now, a method for detecting this labeled DNA or a labeled protein using a DNA substrate of the present invention will be described. FIG. 14 is a block diagram showing a detection apparatus 39 for detection. Firstly, the left half of the block diagram will be described. Light emitted from an excitation light source 40, such as laser or the like, is converged by a mirror 41 having wavelength selectivity and a lens 42, and is focused on a substrate 1. Reflected light from the substrate 1 reaches a detection section 43 via the mirror 41 and a polarizing mirror 42. A focus error signal detection section 45 sends a focus error and a tracking error to a focus control circuit 46 and a tracking control circuit 47, respectively. An actuator 48 drives and controls the lens 42 in such a manner as to match the focus with tracking. A focus offset signal generation section 49 and a track offset signal generation section 50 apply an offset to the focus and the tracking in order to optimize a label detection signal. In the present invention, the arrangement of DNA spots 2 is intentionally modulated to include positional information. A procedure for reproducing this data will be described below.

A main signal is reproduced by a main signal reproduction section 69. A positional information detection section 64 detects positional information. A track number output section 52 and a DNA spot number output section 51 send a currently scanned DNA spot number and track number to a data processing section 55. Thereby, a DNA spot is identified.

A signal from a data region 18 shown in FIG. 5 is reproduced to data by a demodulation section, such as EFM, PM, or the like, in the main signal reproduction section. The data is subjected to error correction in an ECC decoder 53. DNA substrate attribute data shown in FIG. 6 is reproduced by a DNA substrate attribute data reading section 54, and is sent to the data processing section 55. In the data processing section 55, the capture DNA identification number 58 of a currently scanned DNA spot 2a is identified. A mirror 65 is used to send fluorescence corresponding to the capture DNA identification number 58 to a first label signal detection section 60. Therefore, the label intensity data (fluorescence level, etc.) of a first identified DNA having a specific identification number corresponding to the capture DNA 3 is output from the label signal output section.

A fluorescence dye 38 of the first labeled DNA 22 linked to the DNA spot 2a is irradiated with excited light from a light source 40 having a first wavelength $\lambda_0$. After the emission of fluorescence is started and continued for the half life, the fluorescence comes to a half level. The half life is in the range of several nanoseconds to several tens of microseconds.

Figure 17:
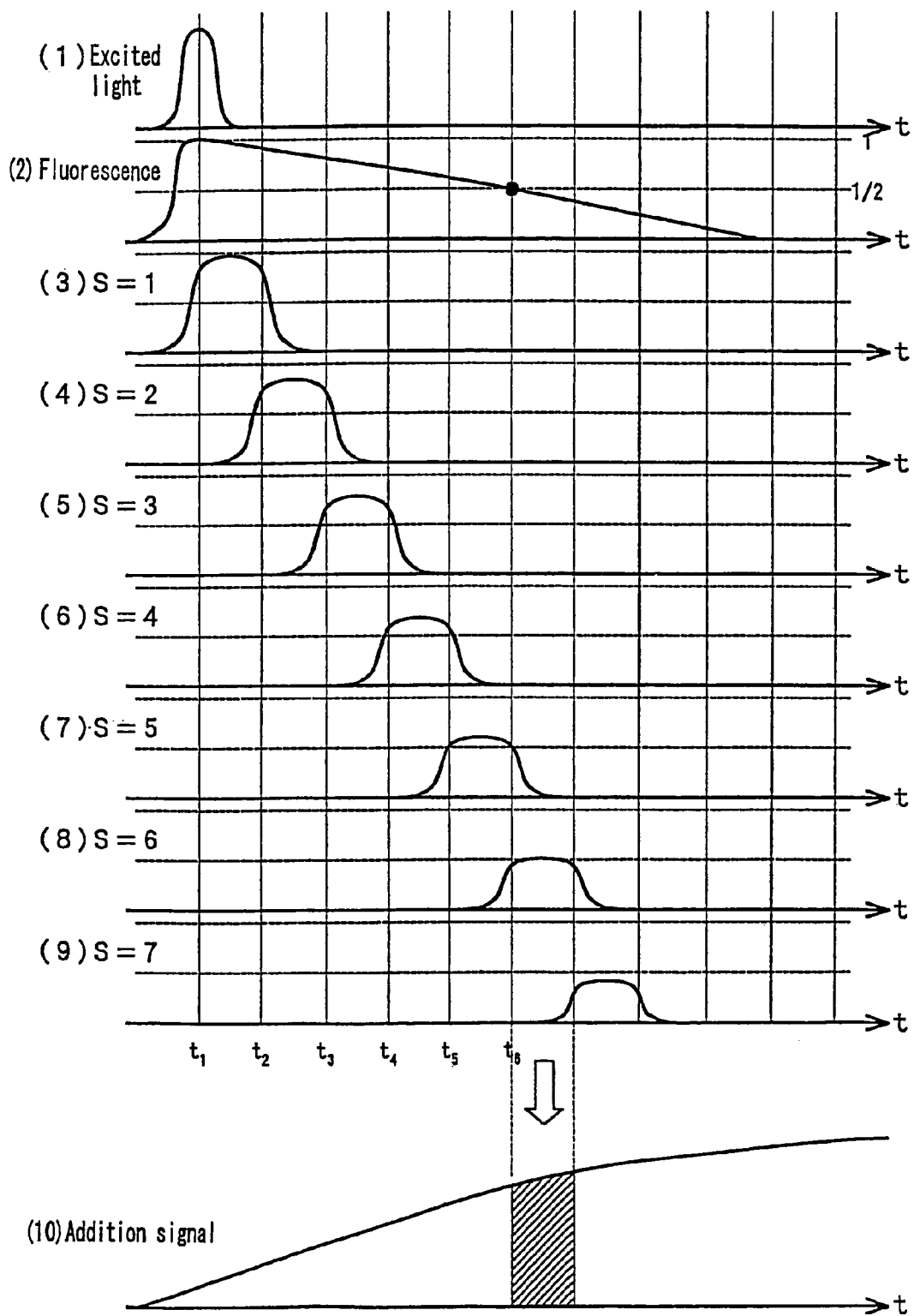

FIG. 17(1) shows the output power of excited light. FIG. 17(2). shows the intensity of fluorescence emitted from a fluorescent material or a fluorescence dye by excited light. FIG. 17(2) shows that the fluorescence intensity comes to the half life at $t=t_6$.

Figure 16:
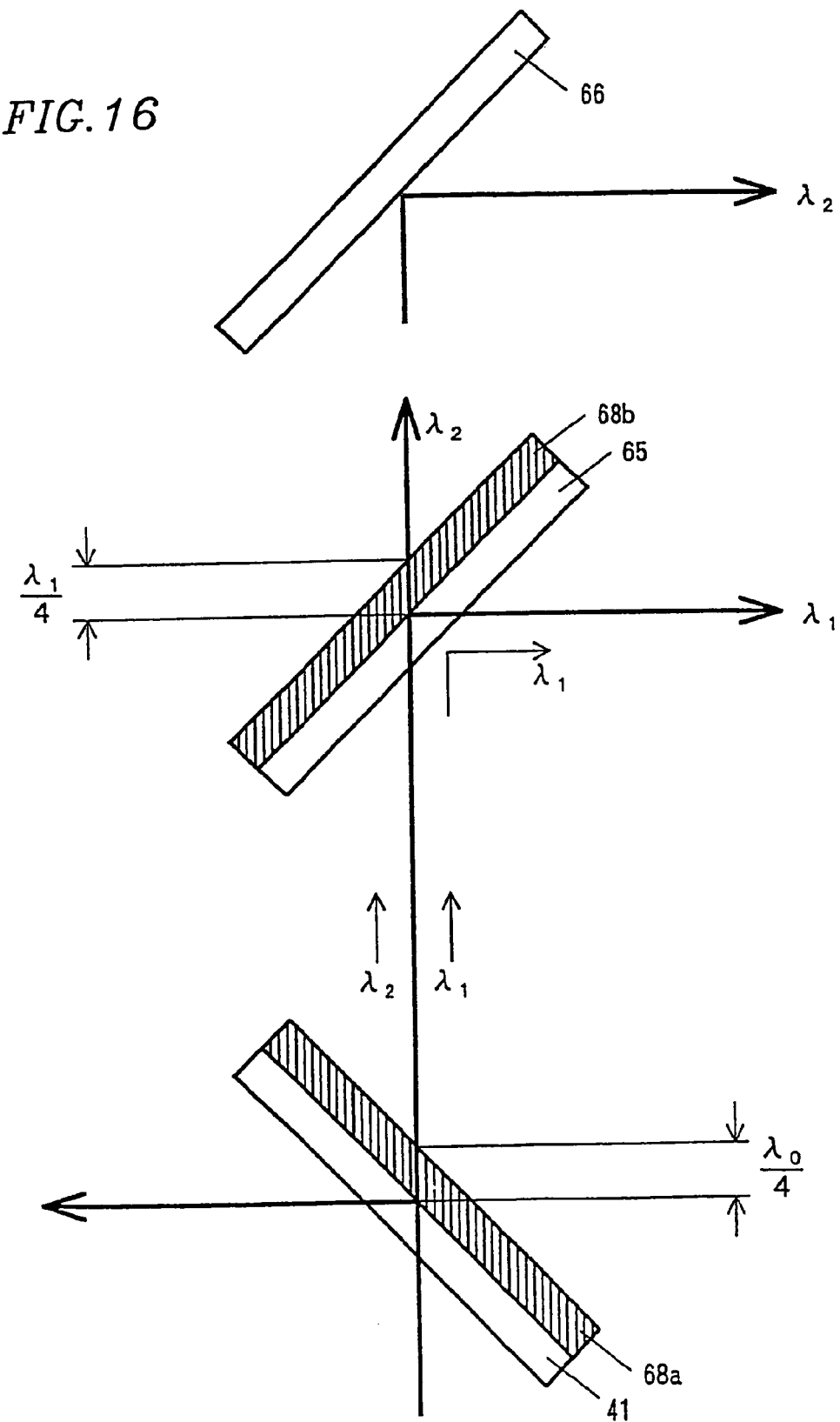
Figure 18:
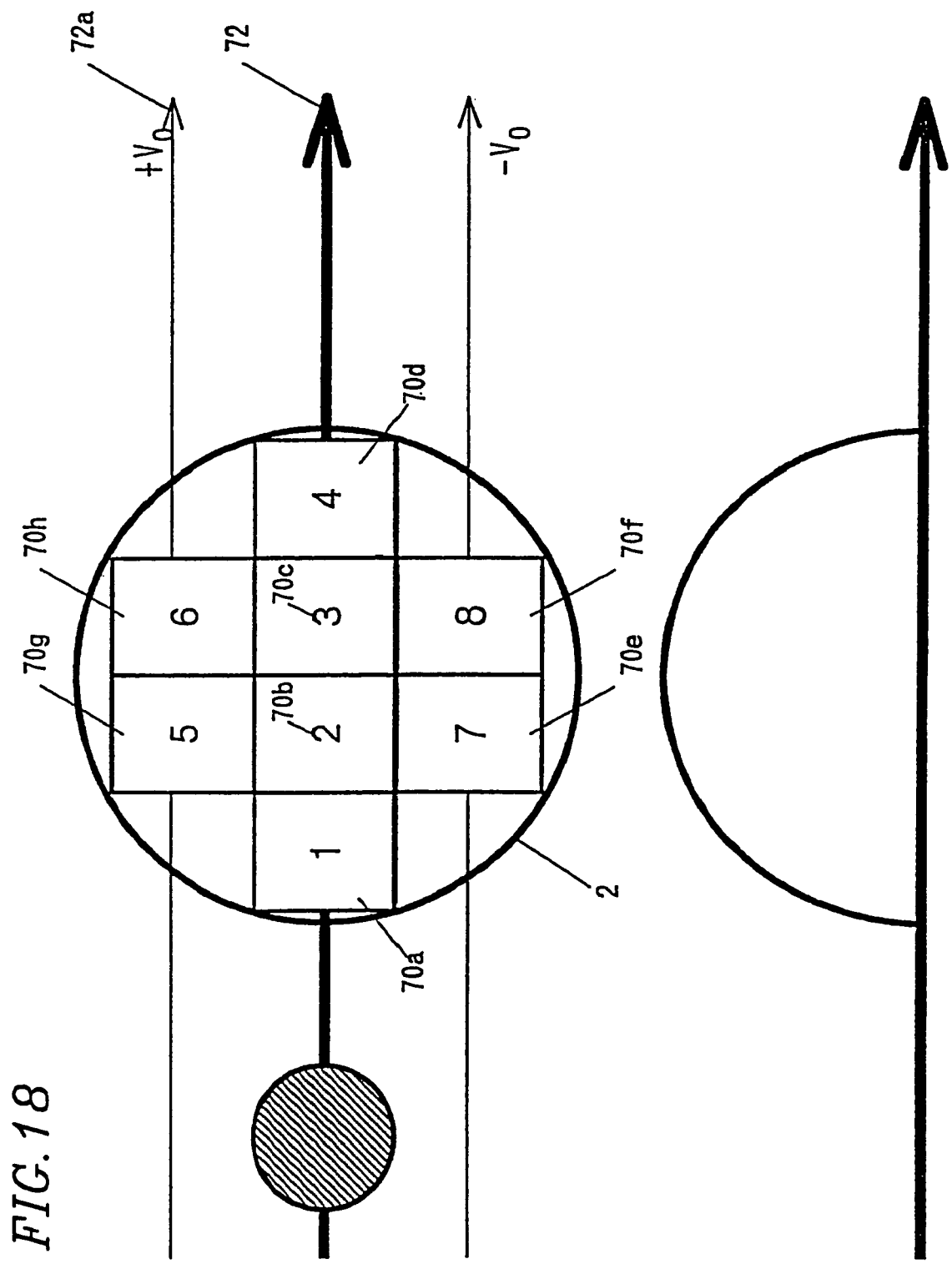

Now, a method for separating wavelengths will be described in detail with reference to FIG. 16. Of a plurality of incident light beams $\lambda_0$, $\lambda_1$ and $\lambda_2$, the excited light with wavelength $\lambda_0$ having the highest intensity is reflected by the mirror 41 having an optical film 68a with a film thickness of $\lambda_0/4$. Fluorescence with wavelength $\lambda_1$ from a first label is reflected by the mirror 65 having an optical film 68b with a thickness of $\lambda_1/4$, while fluorescence with wavelength $\lambda_2$ transmits the mirror 65. Thus, the three wavelengths are separated. The transmittance of the separated wavelength is less than or equal to $1/1000$, and therefore, the crosstalk between each wavelength is suppressed. Therefore, a weak fluorescence label level can be detected. A $\lambda/4$ filter for $\lambda_0$ can be added to further improve the degree of separation, thereby making it possible to suppress the components of the excited light source 40, and therefore, increasing the S/N ratio. As shown in FIG. 18, an excited light beam 71 is made smaller than the DNA spot 2. For example, the size of the excited light beam 71 is as small as several micrometers. In this case, the DNA spot 2 can be divided in a scanning direction, i.e., a direction of a scanning track 72. The resultant portions are called cells 70a, 70b, 70c, 70d. Four pieces of data are obtained in the scanning direction, thereby making it possible to measure the distribution of the amount of fluorescence with higher precision. Cells 70g, 70h are measured as follows: a track error signal, which is $V_0$ in the track offset signal generation section 50, is intentionally generated; the track error signal is input to the tracking control circuit 47; an offset is generated in a track direction; and as indicated by a scanning track 72a in FIG. 18, a track is shifted so that the cells 70g, 70h are scanned while applying excited light to the cells 70g, 70h. When an inverse track error signal is input, cells 70e, 70f can be scanned. Thus, in the case of FIG. 18, the DNA spot 2 is divided into 8 cells which can be scanned and irradiated with excited light.

Figure 20:
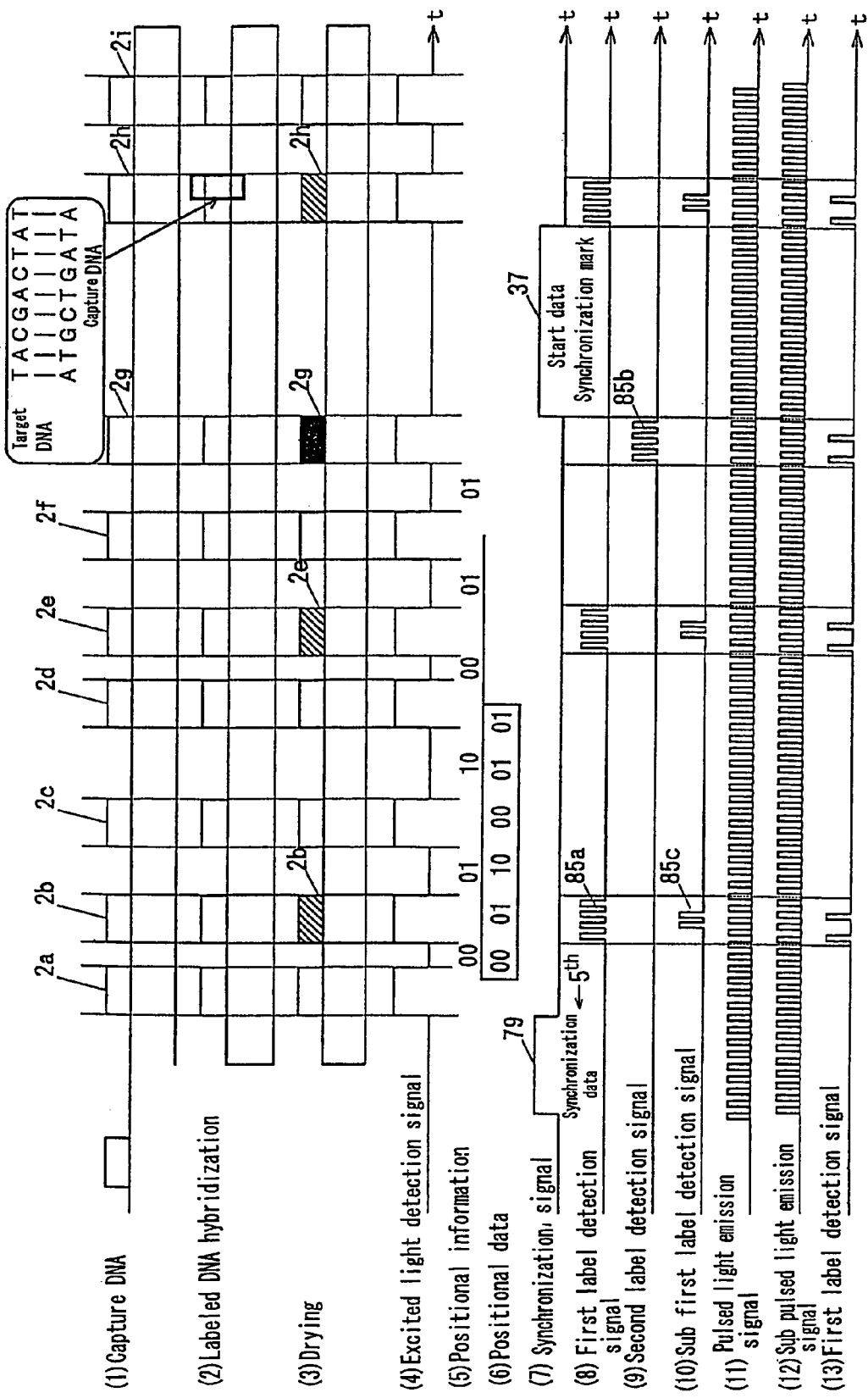

Next, a detection procedure will be described with reference to FIG. 20. FIG. 20(1) shows that DNA spots 2a to 2i are arranged on a DNA substrate 1. In (2), first labeled DNA 22a having a label with a first fluorescence wavelength $\lambda_1$ and second labeled DNA 22b having a label with a second fluorescence wavelength $\lambda_2$ are introduced onto a substrate to carry out hybridization. The first labeled DNA 22a is complementarily coupled with DNA contained in DNA spots 2b, 2e, 2h. The second labeled DNA 22b is coupled with a DNA spot 2h. In (3), drying is performed, and scanning is started using an excited light source 40 with a wavelength $\lambda_0$. (4) shows an excited light detection signal for reflected light of the excited light. Fluorescence generated by the excited light with the wavelength $\lambda_0$ does not contain a wavelength component of $\lambda_0$, so that only a detection signal with $\lambda_0$ is obtained. The surface of the substrate 1, such as glass or the like, has a certain reflectance. Nevertheless, a reflection layer may be further formed on the surface of the substrate of FIG. 1 in order to increase the signal level of the excited light detection signal. A detection signal as shown in (4) is obtained due to the difference in reflectance between the reflectance of a DNA spot 2 with respect to $\lambda_0$ and the surface of the substrate 1. As described concerning the procedure for DNA spot formation with reference to FIG. 10, positional data or the like is buried by changing the pattern or arrangement of DNA on the substrate 1 of the present invention depending on specific data. As shown in (4), the interval between detection signals varies. As a result, signals 00, 01, 10, 00, 01, 01 can be reproduced as shown in (5). Based on these signals, positional data, i.e., address information as shown in (6) can be reproduced. Therefore, for example, it can be found that a DNA mark 2a is located in $260^{th}$ track and at $1128^{th}$ address. A detection apparatus obtains DNA substrate attribute data from the data region 18 of the substrate 1 as described with reference to FIG. 6. Specifically, for example, the start number of DNA identification number in $260^{th}$ track in DNA number positional information 20 is 243142. Therefore, DNA having identification number 244270 can be identified. Further, when the user can obtain an encryption key 73, encrypted DNA sequence information for DNA number (=244270) in sequence information 21 by DNA number is decoded by a cipher decoder 74. Thereby, the DNA spot 2 can be identified to the extent that the DNA spot 2 has a DNA sequence ATCTAGTA . . . . Note that when the user does not have the encryption key 73, DNA sequence is not decoded. In this case, even if the fluorescence data of a DNA spot is obtained, the privacy of personal DNA information is protected. In a postscript data region 76 of FIG. 6, first label attribute data 77 and second label attributed at a 78 of hybridized labeled DNA is additionally recorded, such as the excited light wavelengths 410 nm, 410 nm of labels, fluorescence wavelengths 700 nm, 600 nm, half lives 100 ns, 100 ns, or the like. Therefore, the operations of the detection apparatus can be checked or set using this postscript data.

Returning to FIG. 20, a procedure for measuring the fluorescence of a label generated by excited light will be described. Initially, as described in FIG. 18, in the case of the scanning track 72, cells 70a, 70b, 70c, 70d are scanned with excited beam 71. In the case of a DNA spot 2b, fluorescence with a wavelength $\lambda_1$ is generated, and is detected by the first label signal detection section (FIG. 14). As a result, a first label detection signal 85a corresponding to the four cells are detected as shown in (8). When a DNA spot 2g is scanned, fluorescence with a wavelength 2 is generated, and a second label detection signal 85b is generated as shown in (9). When an offset is applied in FIG. 18, i.e., in the case of the scanning track 72a, a label detection signal 85c resulting from detection of fluorescence only from two cells is obtained as shown in (10).

In the present invention, when a higher detection sensitivity of labeled DNA is required, the excited light source 40 is caused to emit intermittently. A shift amount in a linear direction or a rotational direction of the substrate is detected by a shift amount detector 86. A pulsed light emission signal 88 or a sub-pulsed light emission signal 87 having reversed phase is generated by the pulsed light emission control section 87 depending on the shift amount. In first scanning, as shown in (11), when the pulsed light emission signal 88 is applied to the light source 40, pulsed light emission is performed. As a result, first and third cells, i.e., cells 70a, 70c, generate fluorescence. In this method, fluorescence is detected when the light source 40 is in the OFF state. Therefore, a considerably high S/N is obtained. For example, a label detection signal 85d is obtained as shown in (13). In this case, a light receiving portion of the first label detection section is slightly shifted, so that light receiving efficiency is improved. In second, i.e., even numbered, scanning, a sub-pulsed light emission signal having reversed phase as shown in (12) is input to the light source 40, and the same track 72 is scanned. Due to the reversed phase with respect to the first scanning, second and fourth cells, i.e., cells 70b and 70d (two clocks after) (FIG. 18) are irradiated with excited light. During the subsequent on clock, excited light is OFF. Therefore, fluorescence from the cell 70b or 70d can be detected without interference by excited light. Thus, by scanning two times, the fluorescence levels of all cells can be advantageously detected with high sensitivity. A description will be given with reference to a flowchart of FIG. 31. In step 118a, scanning is performed once so that the arrangement information of all DNA spots on the track is stored into a memory (steps 118b, 118c). In this case, in step 118d, if scanning is performed at a constant speed in the second time or thereafter, the positions of the DNA spots can be reproduced by reading out from the memory (step 118f).

Figure 31:
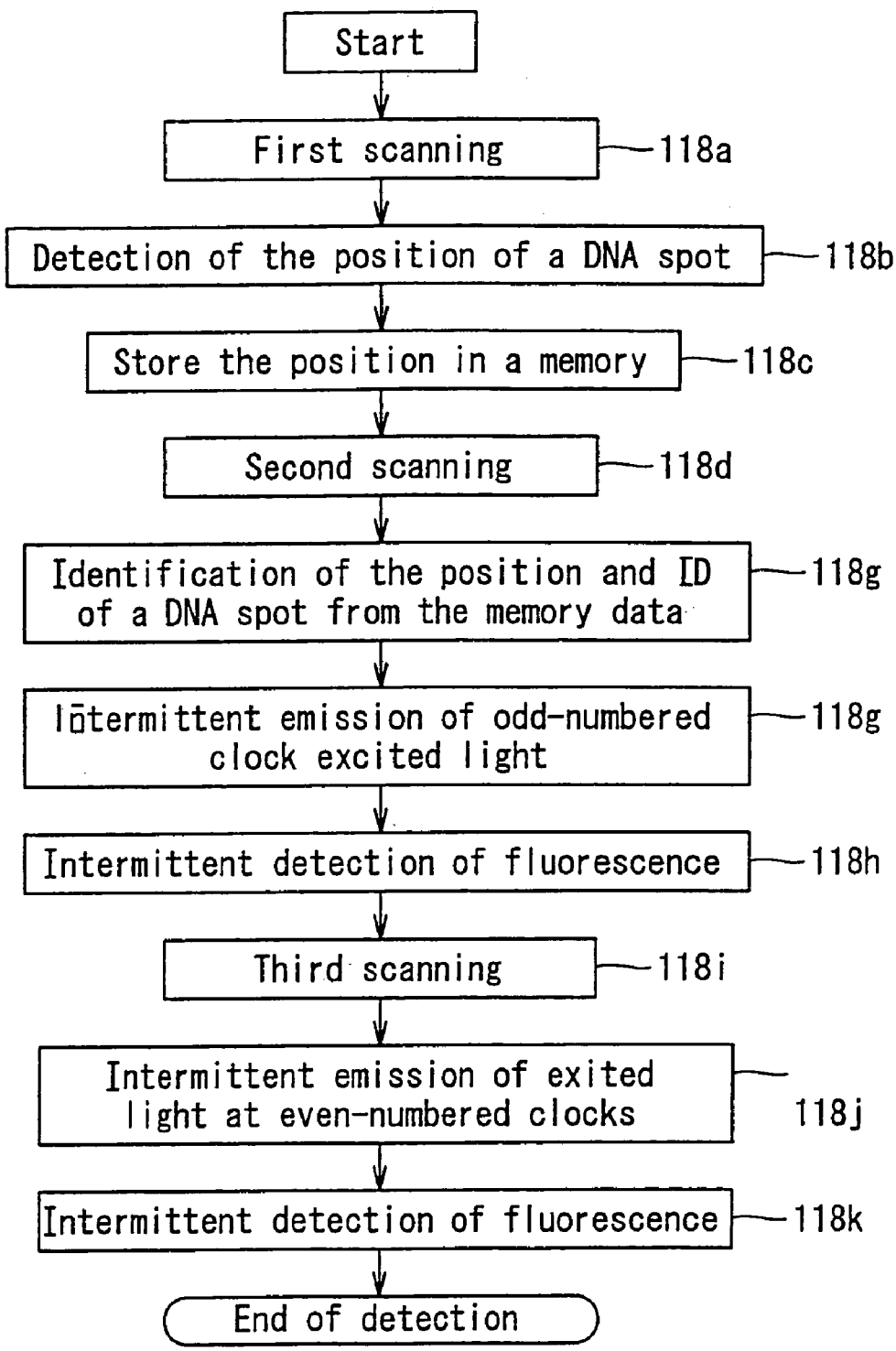

A description will be given with reference to FIGS. 31 and 32. In step 118g, excited light is intermittently emitted at odd numbered clock times (FIG. 32(2)). Fluorescence is generated (FIG. 32(4)). In step 118h, fluorescence is detected based on a detection permitting signal of FIG. 32(3) (FIG. 32(5)).

Figure 32:
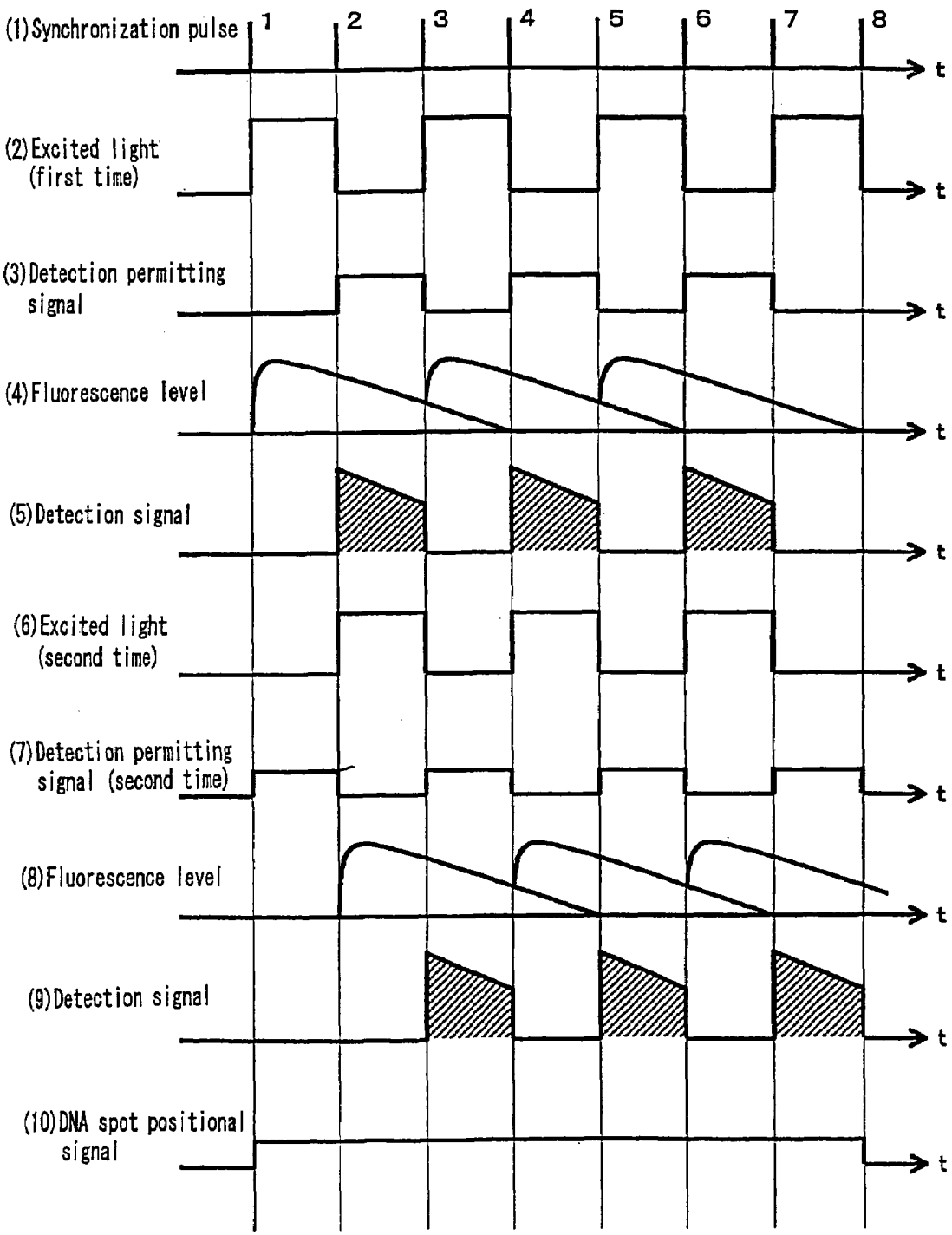

In third scanning, excited light is intermittently emitted at even numbered clock times in step 18j (FIG. 32(6)). In step 118k, fluorescence is intermittently detected (FIG. 32(9)). Therefore, the influence of excited light is eliminated, whereby SN is improved.

Accordingly, in the present invention, high precision in the linear direction is obtained even by pulsed light emission. No problem arises in precision in the track direction.

Figure 19:
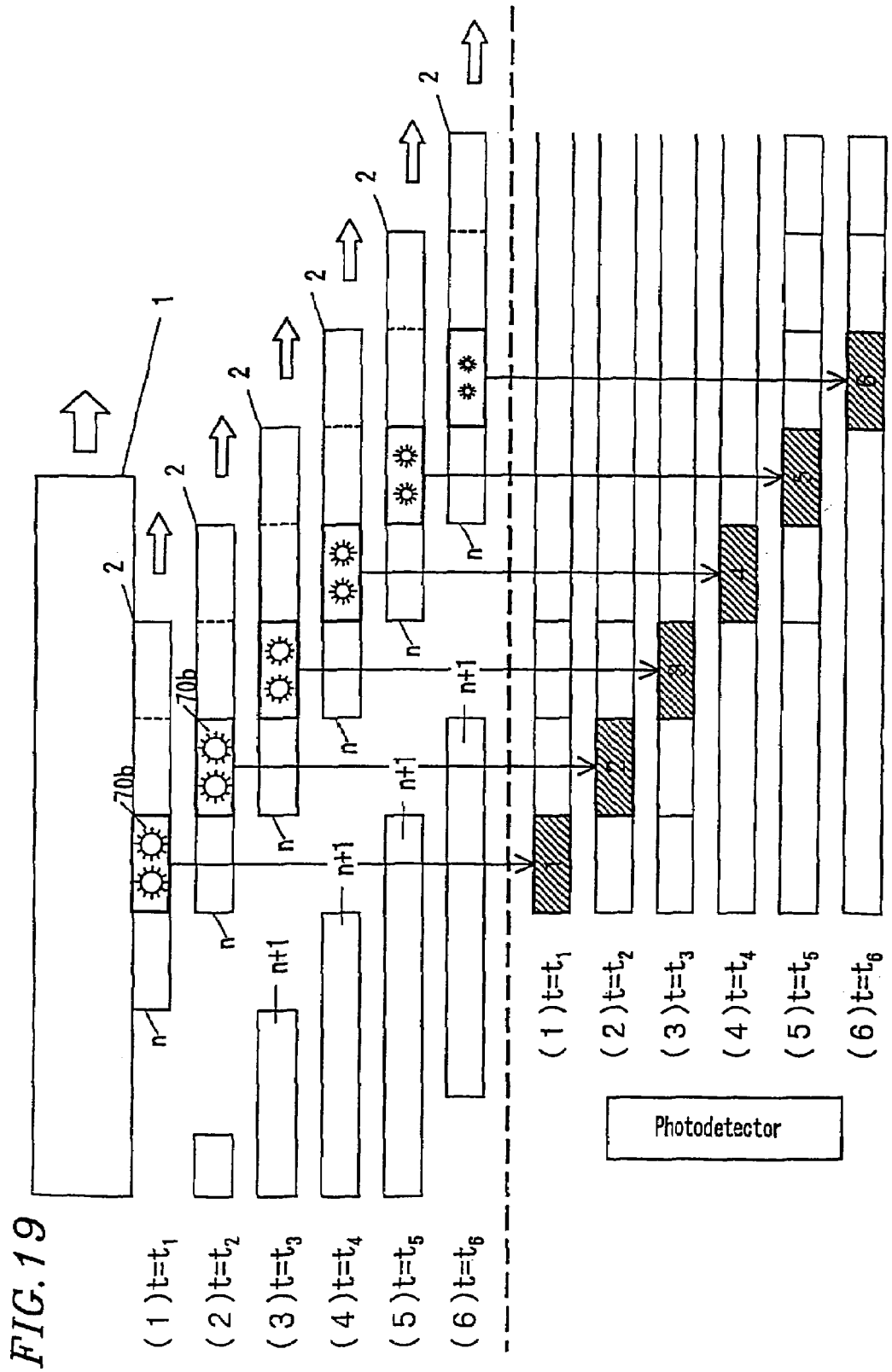
Figure 21:
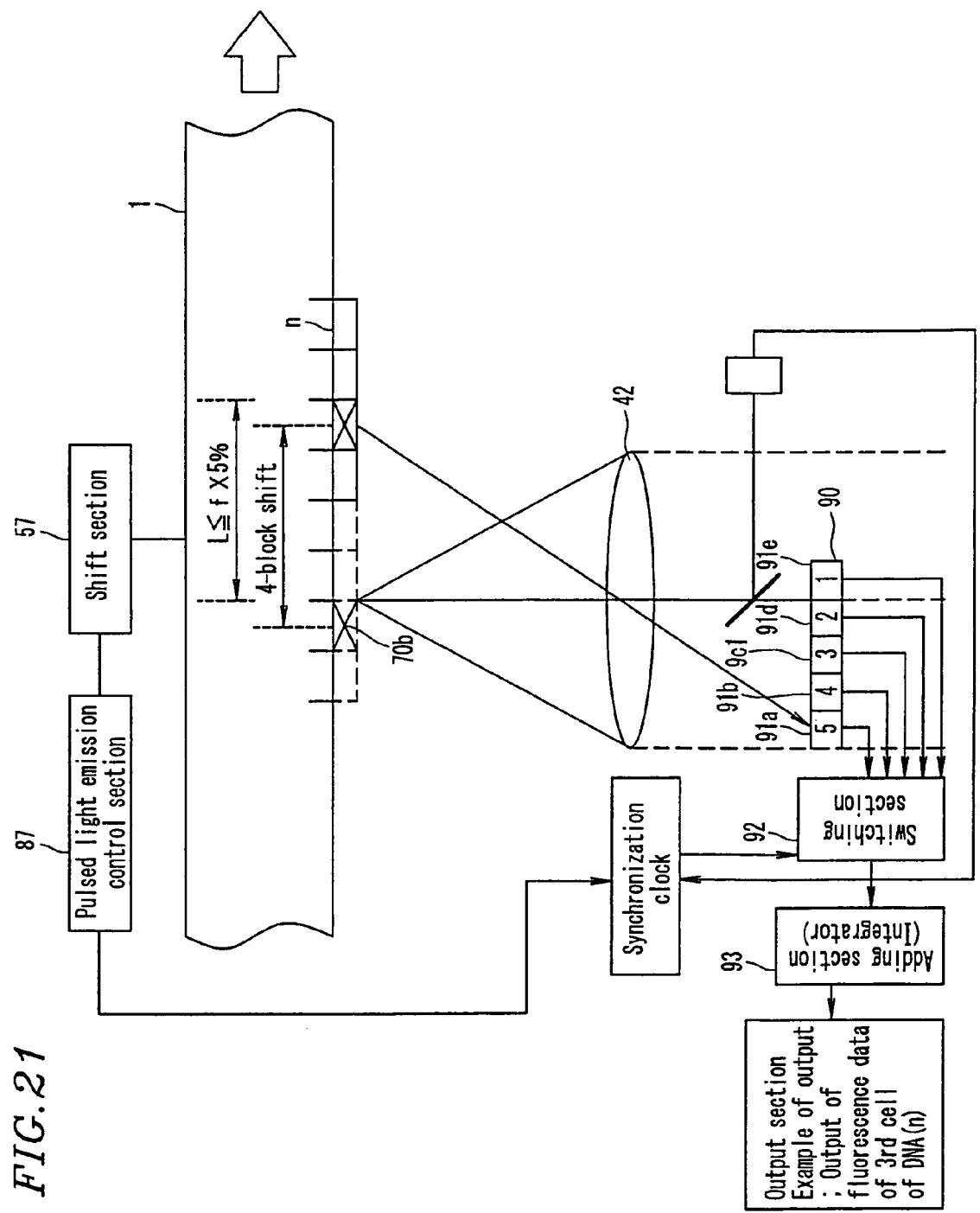

Next, a method for improving sensitivity while enhancing positional resolution will be described. Referring to FIG. 19, the substrate 1 is moved so that the cell 70b is moved in the order of (1), (2), (3), (4), (5), and (6). In order to measure the amount of fluorescence from the substrate 1, a light detection section 90 has an array structure 91 and perform switching in the order of (1'), (2'), (3'), (4'), (5'), and (6'), depending on the shift amount. Thereby, a high level of sensitivity is obtained while keeping a resolution. FIG. 21 is a block diagram showing that switching is performed on the array by a switching section 92 based on a signal from the shift amount detector 87 and a synchronization signal from the DNA spot 2; the fluorescence of the cell 70b is tracked, and fluorescence data is accumulated and output by an addition section 93. In this case, if the amount of shift from the center of a cell is within f×0.05 where f represents the focal distance of the lens 42, the cell can be detected by the array 91.

A label detection signal list 94 in the detection apparatus has data as shown in FIG. 22. This data is recorded into the data region 18 of FIG. 5 with excited light. In this case, all data can be integrated with a single substrate. Therefore, the possibility of obtaining incorrect data is eliminated, thereby avoiding accidents, such as false diagnosis and the like.

Figure 23:
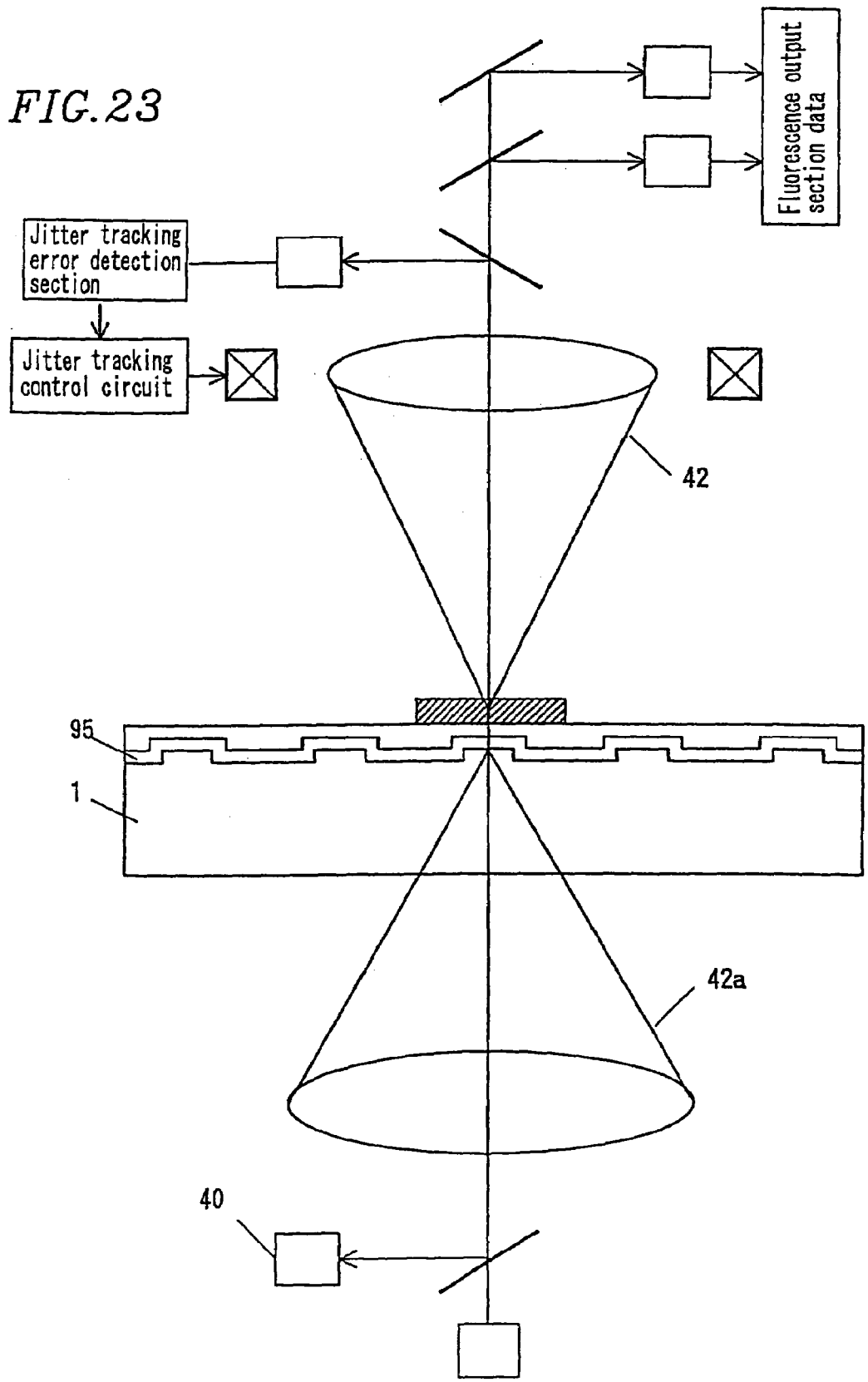
Figure 24:
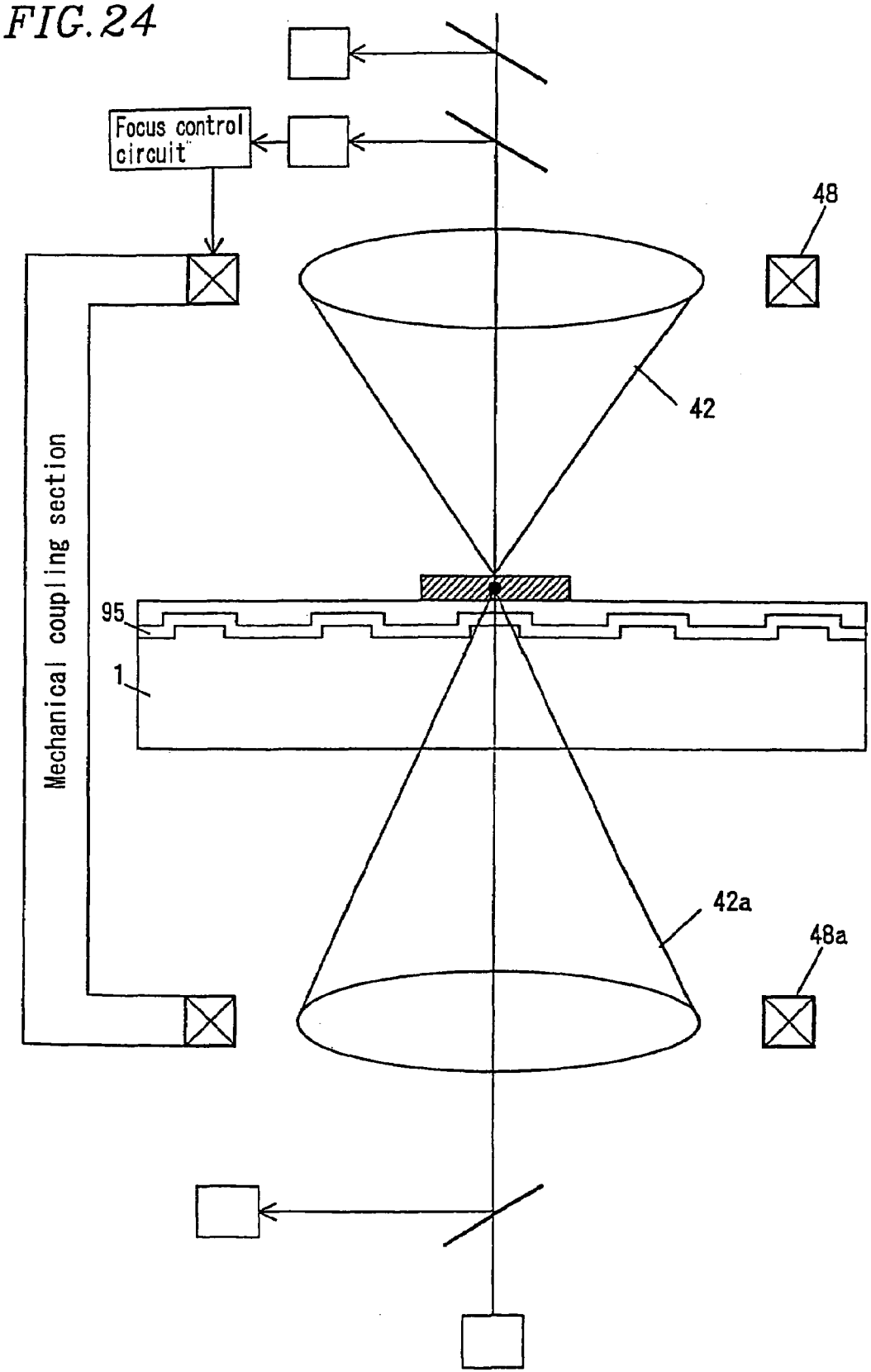
Figure 25:
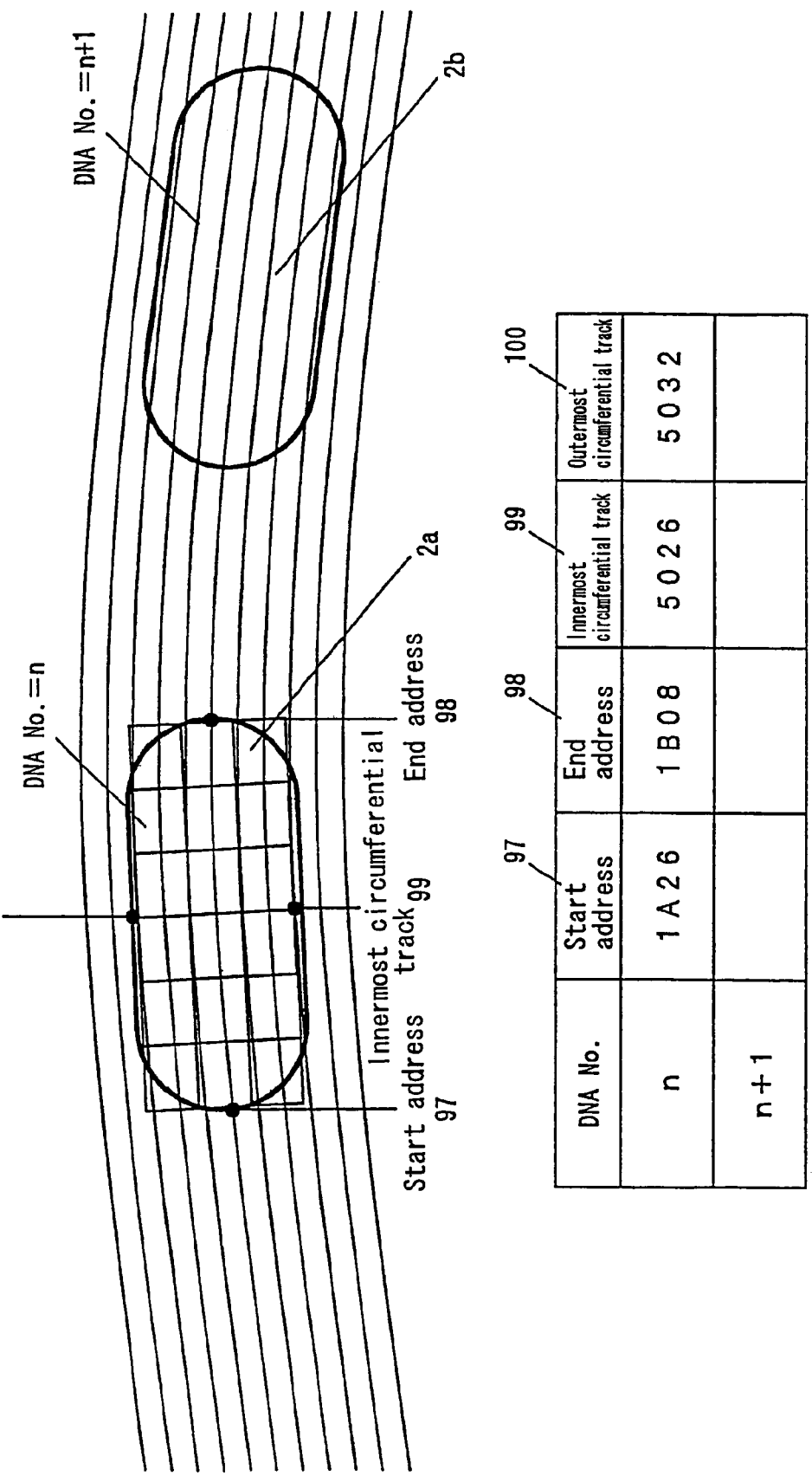
Figure 26:
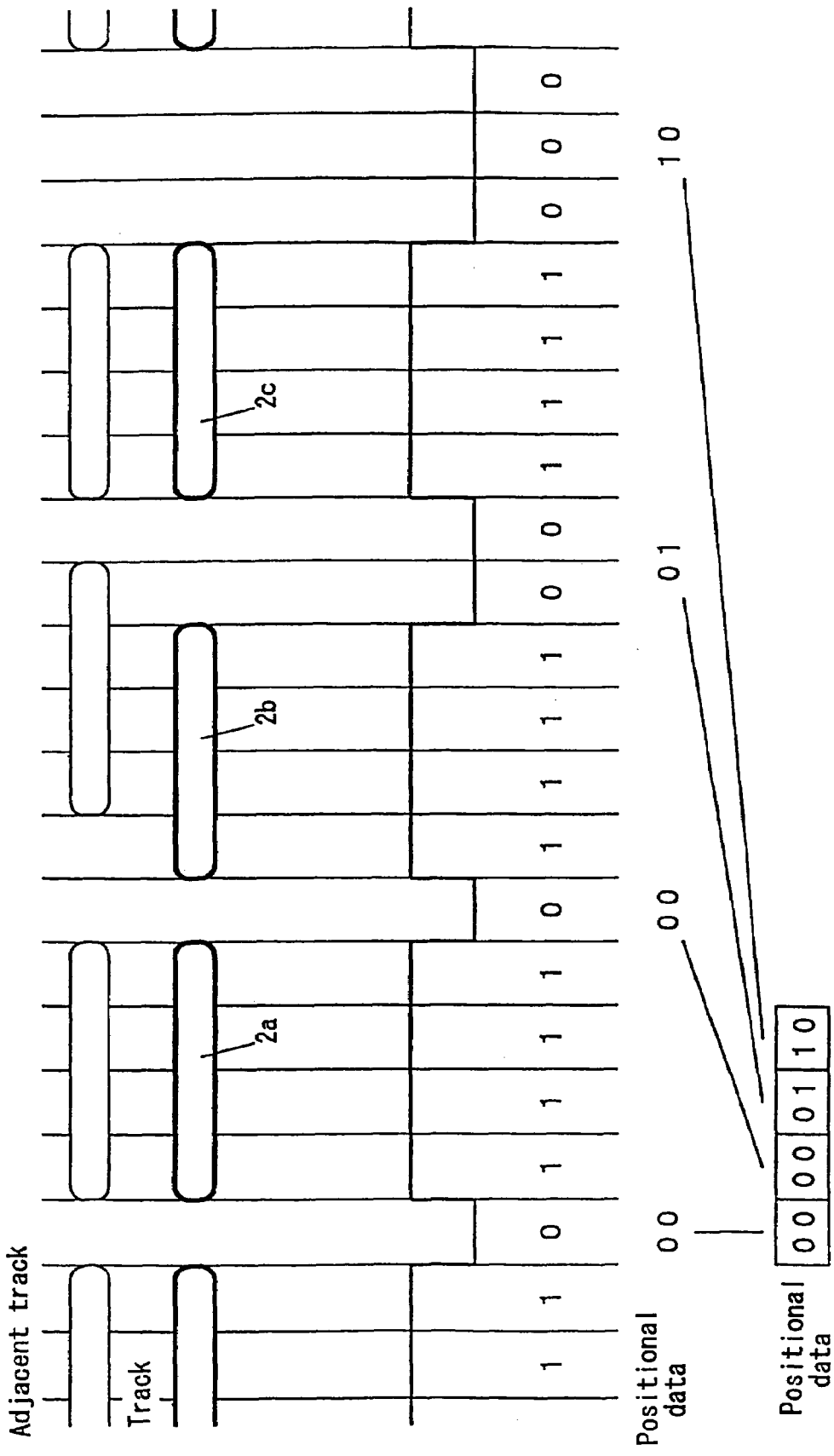
Figure 27:
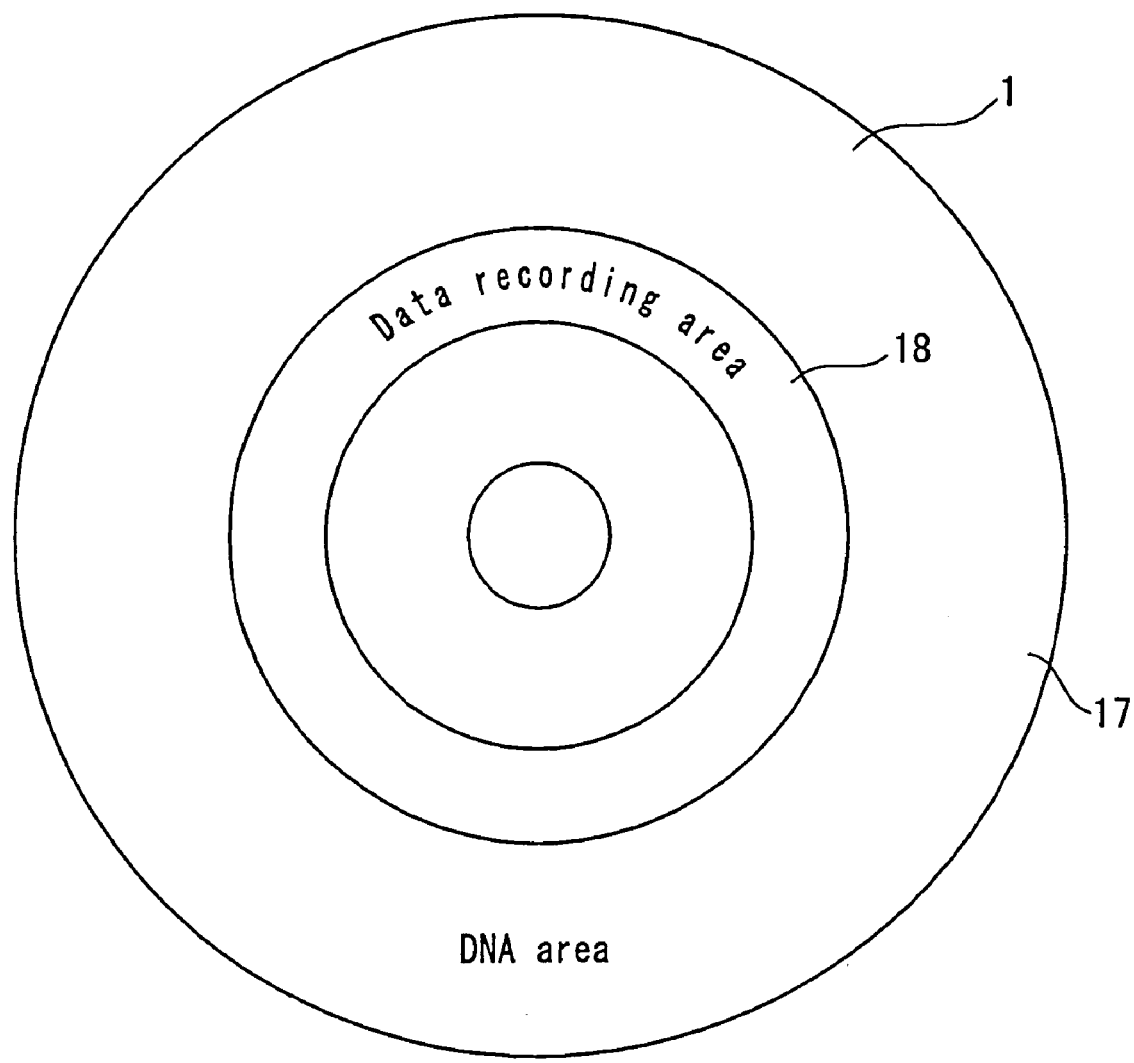

FIG. 23 shows that a recording layer 95 is added to a substrate 1 and a light source 40 and a lens 42a are provided on the opposite side of the substrate to the recording layer 95. Since data can be recorded in the recording layer 95, a large volume of data can be recorded. FIG. 24 shows that two upper and two lower actuators 48, 48a are mechanically coupled together. In this case, as shown in FIG. 25, since the position of each DNA spot 2a can be defined with an address 96 in the recording layer 95, the outer shape of the DNA spot 2a can be specified with a start address 97, an end address 98, innermost circumferential track number 99, and an outermost circumferential track number 100, thereby making it possible to access a DNA spot at high speed. This correspondence list can be recorded in the recording layer 95. Referring to FIG. 26, DNA spots 2a, 2b, 2c are in the shape of a rectangle, thereby making it possible to perform scanning tracking with higher accuracy. FIGS. 27 and 28 show DNA chips as shown in FIG. 5 but in the shape of a circle. In particular, the entire rear surface of the DNA chip of FIG. 28 can be used. Therefore, the DNA chip of FIG. 28 has a large recording capacity and can store the entirety of a DNA sequence. The term DNA is herein used. Any biomolecule as defined herein (e.g., a protein) may be used as a subject substance to be labeled. RNA may be used instead of DNA. Cells or a part of tissue may be used as long as they can be arranged on a substrate.

In the embodiments, as a method for fabricating a DNA substrate, a PIN method and an ink jet method are employed to describe the examples of the present invention. However, the present invention can also be applied to a semiconductor process method. Referring to FIG. 29, in a semiconductor process method, probe DNA is arranged on a glass substrate. Referring to FIG. 29(2), lithography is performed as follows. A mask 120 is used to perform masking. Specific probe DNA is irradiated to activate an elongation reaction. A probe DNA containing A (adenine) 123 is formed as shown in FIG. 29(3). Thereafter, C (cytosine) 124 is formed as shown in FIG. 29(4) and (5). This elongation reaction is carried out for A, C, G, and T, i.e., four times, to complete one layer. If the elongation reaction is carried out 4N times as shown in FIG. 29(6), probe DNAs having a length of N bases are formed. In the DNA chip fabrication of the semiconductor process method, the position of the opening of the masking is shifted as shown in FIG. 10(7) using the present invention. As shown in FIG. 29(1), a mask 121a is shifted with respect to the original mask 121b in correspondence with specific data. Thereby, positional data can be buried and recorded in an arrangement of DNA spots.

Example 6

Network Type Test Apparatus

Figure 43:
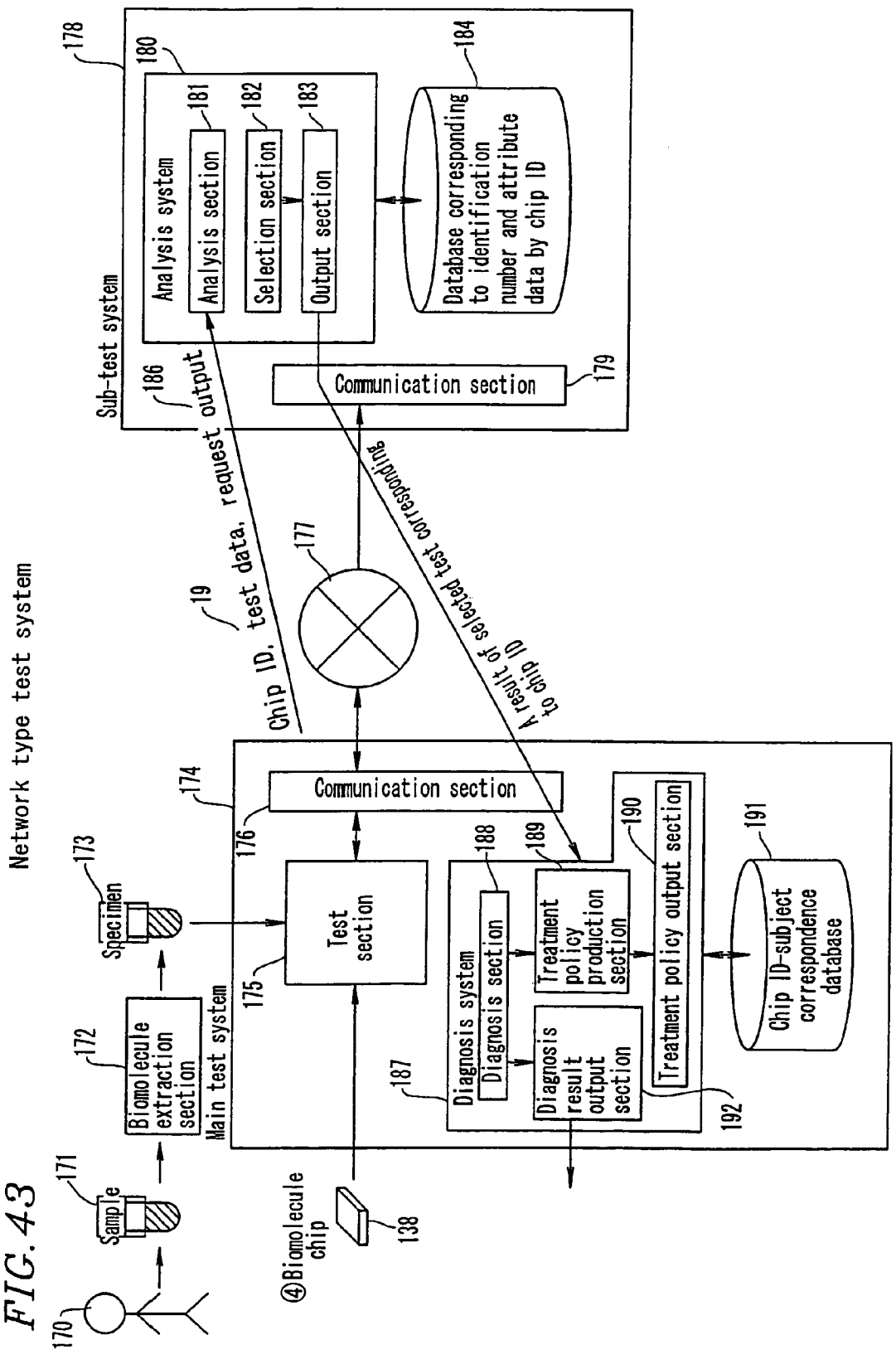

An operation of a test system using a biomolecule chip according to the present invention will be described. FIG. 43 is a flowchart showing the operation of the test system of the present invention. In a biomolecule extraction section 172, a biomolecule is extracted, purified, or grown from a sample 171 collected from a subject 170 to prepare a specimen 173. In a test section 175 of a main test system 174, this specimen 173 is loaded to a biomolecule chip 138, followed by a reaction. A portion of molecules in the specimen 173 are hybridized with probes in a specific biomolecule spot 141 as described above. This biomolecule spot exhibits label information, such as fluorescence or the like, and therefore, can be easily detected. On the other hand, a chip ID 19 can be detected from the biomolecule chip 138. These test data are encrypted together with the chip ID 19 (substrate ID 19 is also referred to as chip ID 19), and the encrypted data is sent via a communication section 176 and then through the Internet 177 or a communication circuit to a communication section 179 of a sub-test system 178, such as a test center or the like. Thereafter, the data is sent to an analysis section 181 of an analysis system 180. In the analysis section 181, the attribute data of each biomolecule spot of a corresponding chip ID can be obtained from an identification number-attribute database 184. From the obtained attribute data and label number, the state of the specimen 173, such as a gene, a protein or the like, can be identified.

An analysis result in the case of genetic information is shown in FIG. 45. Firstly, a gene number 183 corresponding to a gene sequence is shown. Gene attribute data indicating a gene attribute 184 of a gene corresponding to the number contains the sequence of the gene; a marker for a disease, a character, or the like; and the like. Since this type of test is used in a test of a specific disease or a test of a specific molecule, the main test system 174 outputs a request, such as, specifically for example, data "Please output information relating to a disease a". As shown in a selective output 185 of FIG. 45, only information relating to a request output 186 is selected by a selection section 182, and is encrypted by the output section 183 and sent via the communication section 179 and the Internet 187 to the main test system 174.

In a gene test, data which is not originally intended is obtained in the course of testing and analysis. For example, when genetic information on a specific cancer is required, if unintended genetic information, such as other diseases or characters (e.g., an intractable and unavoidable disease (juvenile Alzheimer's disease, etc.), a catastrophic character, etc.), is output, the interest of a subject is likely to be damaged. If this type of information is unintentionally leaked, a privacy problem occurs. According to the present invention, the selection section 182 filters out information unrelated to a request output or raw genetic information, thereby making it possible to prevent unnecessary information from being output.

The result of a test corresponding to a chip ID, which is requested to the main test system 174, is received by the diagnosis system 187 and processed by a diagnosis section 188. The chip ID-subject correspondence database 191 can be used to identify the subject 170 from a chip ID 19. All chips have a unique chip ID. Therefore, the subject corresponding to each chip can be identified. This data is not sent to any sub-test system. Therefore, patient data is prevented from being leaked to a test laboratory or the outside of a hospital. The test system can know the relationship between a subject and a chip ID, but does not have the attribute data of each biomolecule spot of the chip ID. Unless the attribute data is obtained from the sub-test system, whole genetic information cannot be obtained. In other words, the main test system 174 and the sub-test system 178 each have incomplete complementary information, thereby maintaining security. Thus, the security of the genetic information of a subject can be protected.

In this case, each chip ID is different from the others and is provided with a randomized number. Therefore, even if all the attribute information of a chip having a certain chip ID number (e.g., the attribute data of a biomolecule corresponding to the identification number in each biomolecule spot) is made public, the data of any other chip ID cannot be identified, since there is no correlation between the specific chip ID and the other chip IDs. The security of the whole system can be protected as long as the secrecy of the sub-test system can be maintained. When the secrecy of the main test system is maintained, no information connecting a chip to a person is obtained even if a chip and a personal ID are obtained by a third party. In this case, security is further improved.

The diagnosis section 188 outputs a result of diagnosis based on historic data of a subject (a disease, etc.) and a test result obtained from the sub-test system. A diagnosis result output section 192 externally outputs the diagnosis result. A treatment policy production section 189 produces a plurality of treatment policies based on the diagnosis result, assigns priorities to the treatment policies, and outputs the treatment policies through the output section 190.

(Utilization of genetic information other than diseases)

In the above-described examples, information relating to a specific disease is specified as request information and is sent out as a request output 186. Recently, it has been revealed that a psychological attribute, such as a character or the like, of a subject can be obtained from genetic information. For example, it is known that a person whose third exon of the dopamine D4 receptor on the $11^{th}$ chromosome is long has a character of challenge. Thus, now and thereafter, attribute information, such as a personal character, will be clarified from genetic information one after another. Considering this point, attribute data indicating a psychological feature, such as a character, of a subject is added to the disease data in the request output 186 of FIG. 43. In this case, information on the character, aptitude, or the like of a subject 170 is sent from a sub-test system to the diagnosis system 187. The priorities of the treatment policy options of the treatment policy production section 189 are changed depending on the attribute and aptitude data of the subject. For example, for a subject who prefers a high risk and a high result, the priority of a treatment option which provides a high result at a high risk is increased. For a subject who prefers a moderate result at a low risk, the priority of a therapeutic agent, which is safe but whose effect is not high, is increased. With this method, a diagnosis system for providing a treatment policy suitable for the character or aptitude of a subject can be achieved.

Example 7

Stand-alone Test Apparatus

Figure 44:
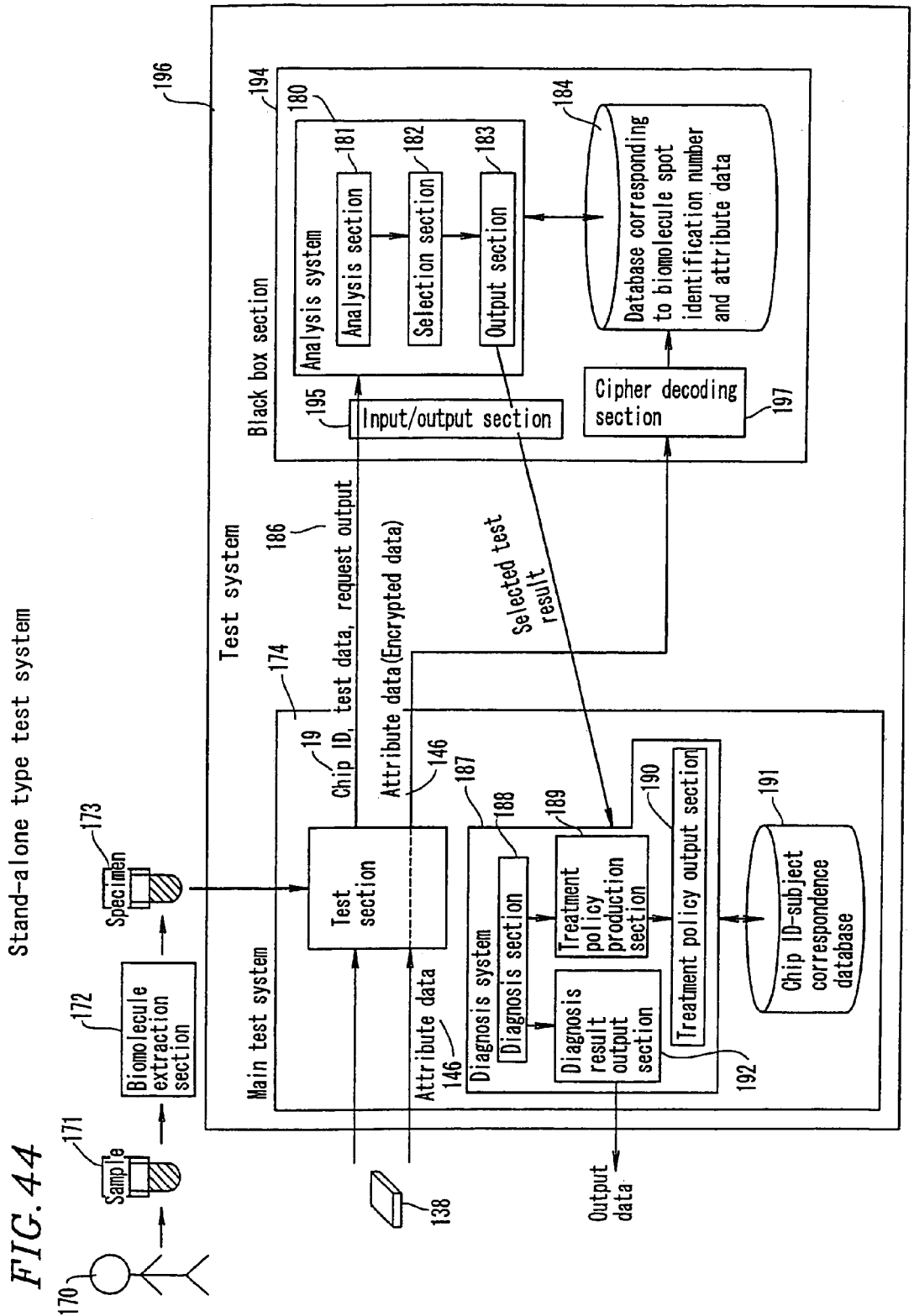

The operation (security, etc.) of the present invention has been described using the exemplary network type test apparatus of FIG. 43. The present invention can be applied to a stand-alone type test system 193 as shown in FIG. 44.

The network type test system of FIG. 43 comprises two systems, i.e., a main test system and a sub-test system. The latter is administered by a neutral entity, such as a test center, and can enhance secrecy to maintain the security of the whole system. In contrast, the stand-alone type test system of FIG. 44 includes a black box section 194 having a high level of secrecy instead of the sub-test system 178. The black box section 194 leaks no internal information other than information required to be output to the outside. Only required data is output from an input/output section 195. The security of information is maintained by the black box section 194.

Most portions of the stand-alone type test apparatus have the same operation as in FIG. 43. Only different points than those in FIG. 43 will be described below. Initially, in a test section 175, encrypted data, such as encrypted biomolecule spot-attribute data 146 encrypted using public key encryption function or the like, is reproduced by a chip 138 and is sent to a black box section 194. This encrypted data is decoded to plain text data by a cipher decoding section 197 within the black box section 194. This plain text data contains attribute information relating to each biomolecule spot on a biomolecule chip. The attribute information is added to a biomolecule spot identification number-attribute database 184.

In the case of FIG. 43, the main test system accesses via a network to the database 184 in a sub-test system, such as a test center or the like and obtains data. Therefore, such a sub-test system, such as a test center or the like, needs to obtain the latest data of all chips produced all over the world and update the data as occasion demands. The main test system cannot obtain a test result unless a network is available. However, in the method of FIG. 44, even if a chip is recently produced, the attribute data 146 is present in the biomolecule chip, and this attribute information is automatically recorded into the identification number-attribute data correspondence database 184, which is thus updated, every time a chip is loaded in a test system. Therefore, the stand-alone type test system does not have to be connected to a network. Moreover, a memory of the test system stores data corresponding to only one chip. Therefore, memory capacity can be significantly reduced. In the case of this method, a mobile type test apparatus can be used. Similar to FIG. 43, in this method, only information relating to an output requested from the main test system is selected by a selection section 182, and is sent from the black box section 194 to a diagnosis system 187 in the main test system 174.

Note that if the black box section 194 is produced in such a manner that, for example, the black box section 194 is incorporated into a chip of LSI and its external terminals are limited to the input/output section 195 and the cipher decoding section 197, no internal data can be externally read out. Therefore, security is protected. As described above, with a biomolecule chip containing encrypted data of the present invention and a stand-alone type test system of the present invention, required testing or diagnosis can be carried out without a network or externally input data while protecting the information security of a subject.

Figure 46:
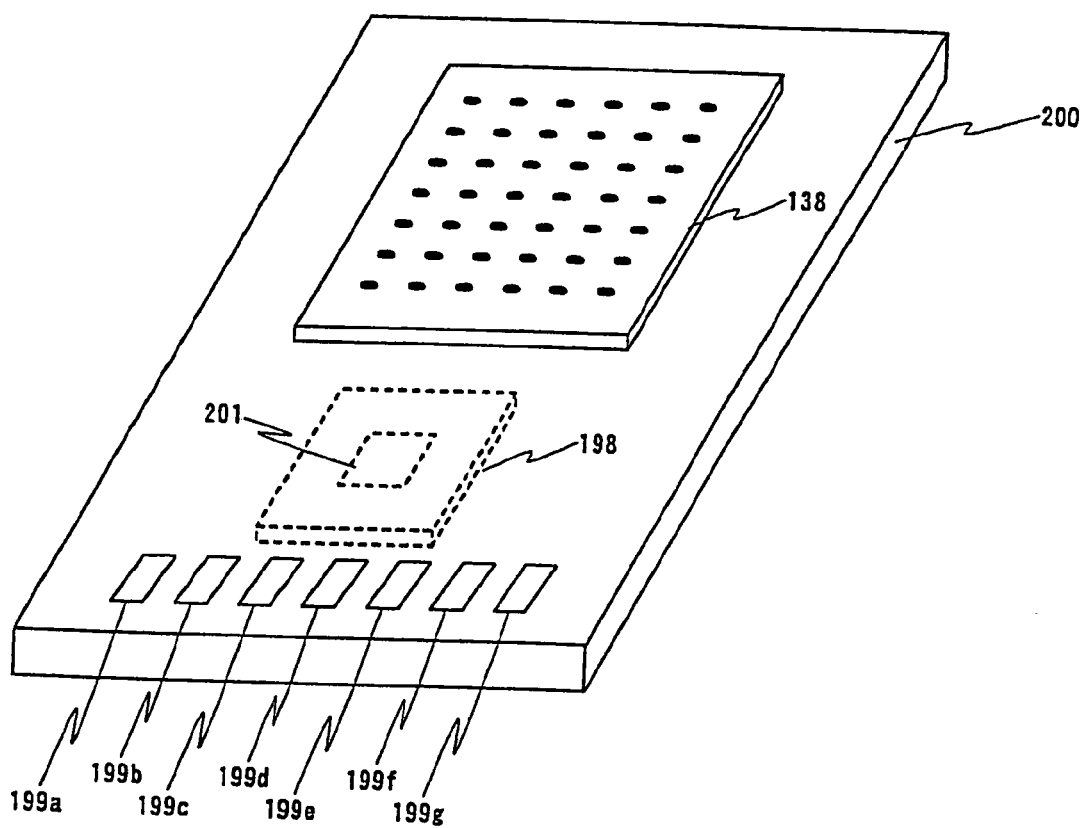

Note that although the above-described example is such that the attribute information of a biomolecule chip is buried in the arrangement data of biomolecule spots, such information may be optically recorded with pit marks or the like on a substrate integrated with a chip as shown in FIG. 5. Alternatively, as shown in FIG. 46, a biomolecule chip 138, an IC chip 198 having a non-volatile memory 201, and an electrode 199 are provided on a substrate 200, the attribute information may be recorded in the non-volatile memory 201 of the IC chip 198. The attribute information may be optically read out in the test system, or may be electrically read out from the electrode 199 or the like.

All of the publications, patents, and patent literature cited herein are each incorporated herein by specific reference. The present invention has been described with reference to various particular and preferable embodiments and techniques. However, it should be understood that various modifications and variations can be made without departing from the spirit and scope of the present invention.

Note that in the description of the embodiments, the arrangement of biomolecule spots is changed in the same direction as a single specific arrangement direction of biomolecule spots. However, other methods can be easily implemented, though their descriptions are omitted. First of all, the size of a biomolecule spot may be changed. Specifically, data "01" is assigned to a biomolecule spot having a small size; "10" is assigned to a biomolecule spot having a middle size; and "11" is assigned to a large size. Thus, three-valued data can be buried in one biomolecule spot.

Alternatively, the position of a biomolecule spot may be intentionally shifted from a reference position in a direction perpendicular to a specific arrangement direction of biomolecule spots. Specifically, data "01" is assigned to a biomolecule spot shifted by +20% with reference to the reference position; "10" is assigned to a biomolecule spot shifted by 0%, i.e., not shifted; and "11" is assigned to a biomolecule spot shifted by −20%. In this case, three-valued data can be buried in one biomolecule spot. If the number of the shift amounts or resolutions is increased, multivalued data, such as five-valued data, seven-valued data, or the like, can be buried.

Alternatively, the size of a biomolecule spot may be changed in a direction perpendicular to a specific arrangement direction without shifting the position of the biomolecule spot. For example, data "0" is assigned to an elliptic biomolecule spot having a major axis in the vertical direction, and data "1" is assigned to a circular biomolecule spot, thereby making it possible to bury two-valued data. Alternatively, the size of a biomolecule spot may be changed in the same direction as the arrangement direction.

If a plurality of methods of the above-described burying methods are simultaneously used, the amount of buried data can be further increased.

INDUSTRIAL APPLICABILITY

As described above, in the present invention, the position or pattern itself of a biomolecule (e.g., DNA, RNA, a protein, a low weight molecule, etc.) is changed to bury the positional information of the biomolecule. Therefore, no extra process is required and conventional high-precision positioning is no longer required. This method is more effective when the number of types of biomolecule is large and the density of biomolecules is required. Further, a test apparatus can read out the positional information of a DNA spot using an excited light source, and therefore, biomolecule spots may be only relatively positioned. No conventional high-precision apparatus for absolutely positioning biomolecule spots is required. Thus, a test apparatus can be obtained by only a simple configuration. Furthermore, data is recorded on a substrate, and the data is read out using excited light. Therefore, the attribute data of a biomolecule spot can be read out from the same substrate without increasing the number of components, where by data matching error is eliminated. The above-described advantageous effects accelerates widespread use of a biological test apparatus and diagnosis apparatus.

The invention claimed is:
1. A system including:
a biomolecule bead-containing tube comprising a biomolecule bead array in which biomolecule beads having a specific biomolecule immobilized thereon, and marker beads comprising first marker beads having a light absorbing optical property and second marker beads having a light transmissive optical property, are arranged in a tubular container made of a material configured to transmit light having a specific wavelength, a device for determining the arrangement of the biomolecule beads and the marker beads which are in a predetermined order within the biomolecule bead array, wherein a first arrangement of a first set of biomolecule beads and marker beads in the tube corresponds to specimen identification information which identifies a specimen in the tube, wherein a second arrangement of a second set of biomolecule beads and marker beads in the tube corresponds to tube identification information which identifies the tube, and biomolecule attribution information which identifies the biomolecule beads; and wherein said tube identification information is encoded on the marker beads using a pattern of the first and second marker beads, the light absorbing and light transmissive optical properties optically distinguishing the first and second marker beads from each other.

2. A method for analyzing a specimen comprising the steps of:

arranging in a bead-containing tube, biomolecule beads having a specific biomolecule type immobilized thereon and marker beads comprising, first marker beads having a light absorbing optical property and second marker beads having a light transmissive optical property, encoding tube identification information on the marker beads using a pattern of the first and second marker beads, the tube identification information identifying the tube containing the specimen;

storing the tube identification information in a memory; and analyzing the specimen by irradiating the pattern of the first and second marker beads with a light to read out an emitted light from the biomolecule beads and marker beads in the bead-containing tube so as to optically read out the encoded tube identification information and identify the tube containing the specimen, the light absorbing and light transmissive optical properties optically distinguishing the first and second marker beads from each other.

3. The method of claim 2, wherein the storing tube identification information in memory comprises storing a code for identification of each bead-containing tube.

4. The method of claim 2, wherein storing tube identification information in memory comprises storing data associated with information for identifying an organism or test subject.

5. The method of claim 2 further comprising the step of comparing optically read out tube identification information with a database of tube identification information to identify the specimen.

* * * * *